(12) United States Patent
Woldbye et al.

(10) Patent No.: US 10,017,554 B2
(45) Date of Patent: Jul. 10, 2018

(54) NEUROPEPTIDE Y-DERIVED PEPTIDES

(71) Applicants: University of Copenhagen, Copenhagen k (DK); Næstved Hospital, Næstved (DK)

(72) Inventors: David Paul D. Woldbye, Copenhagen Ø (DK); Casper Rene Gøtzsche, Copenhagen Ø (DK); Kristian Klemp, Charlottenlund (DK); Vladimir Berezin, Copenhagen N (DK); Elisabeth Bock, Charlottenlund (DK)

(73) Assignees: University of Copenhagen, Copenhagen K (DK); Næstved Hospital, Næstved (DK)

( * ) Notice: Subject to any disclaimer, the term of this patent is extended or adjusted under 35 U.S.C. 154(b) by 0 days.

(21) Appl. No.: 14/782,912

(22) PCT Filed: Apr. 10, 2014

(86) PCT No.: PCT/DK2014/050086
§ 371 (c)(1),
(2) Date: Oct. 7, 2015

(87) PCT Pub. No.: WO2014/166497
PCT Pub. Date: Oct. 16, 2014

(65) Prior Publication Data
US 2016/0060320 A1 Mar. 3, 2016

(30) Foreign Application Priority Data
Apr. 10, 2013 (DK) ................................. 2013 70193

(51) Int. Cl.
| | | |
|---|---|---|
| A61K 39/00 | (2006.01) | |
| A61K 31/00 | (2006.01) | |
| A61K 38/00 | (2006.01) | |
| C07K 14/575 | (2006.01) | |
| A61K 38/22 | (2006.01) | |
| A61K 45/06 | (2006.01) | |

(52) U.S. Cl.
CPC .... C07K 14/57545 (2013.01); A61K 38/2271 (2013.01); A61K 45/06 (2013.01); A61K 38/00 (2013.01)

(58) Field of Classification Search
None
See application file for complete search history.

(56) References Cited

U.S. PATENT DOCUMENTS

| | | |
|---|---|---|
| 5,026,685 A | 6/1991 | Boublik et al. |
| 5,328,899 A | 7/1994 | Boublik et al. |
| 6,426,330 B1 | 7/2002 | Nyce et al. |
| 2010/0168215 A1 | 7/2010 | During et al. |

FOREIGN PATENT DOCUMENTS

| | | |
|---|---|---|
| WO | WO-9746579 A1 | 12/1997 |
| WO | WO-03026591 A2 | 4/2003 |
| WO | WO-2004009628 A1 | 1/2004 |
| WO | WO-2004056314 A2 | 7/2004 |

OTHER PUBLICATIONS

Welsh, 1999, Current Opinion in Mol. Therapeutics, 1 (4), pp. 464-470.*
Roth et al., 1999, Ann. Rev. Biomed. Eng., 01, pp. 265-297, specifically p. 283.*
Abid et al., Kinetic study of neuropeptide Y (NPY) proteolysis in blood and identification of NPY3-35, J Biol. Chem., 284: 24715-24724, 2009.
Berglund et al., Recent developments in our understanding of the physiological role of PP-fold peptide receptor subtypes, Exp. Biol. Med., 228: 217-244, 2003.
Brothers, et al., Therapeutic potential of neuropeptide Y (NPY) receptor ligands, EMBO Mol Med, 2: 429-439, 2010.
Cremer et al., Inactivation of the N-CAM gene in mice results in size reduction of the olfactory bulb and deficits in spatial learning, Nature, 367:455-459, 1994.
Erondu et al., Neuropeptide Y5 receptor antagonism does not induce clinically meaningful weight loss in overweight and obese adults, Cell Metabolism, 4: 275-282, 2006.
Hoffmann et al., Structure-affinity studies of C-terminally modified analogs of neuropeptide Y led to a novel class of peptidic Y1 receptor antagonist, Regulatory Peptides, 65: 61-70, 1996.
Kinzeler et al., Functional Implications for Modulating Neuropeptide Y Gene Expression in the Dorsomedial Hypothalamus, The Journal of Neuroscience, 29(23):7389-7391, 2009.
Nielsen et al., Role of Glial Cell Line-Derived Neurotrophic Factor (GDNF)-Neural Cell Adhesion Molecule (NCAM) Interactions in Induction of Neurite Outgrowth and Identification of a Binding Site for NCAM in the Heel Region of GDNF, J. Neurosci., 29: 11360-11376, 2009.
Pankratova et al., Neuroprotective properties of a novel, non-haematopoietic agonist of the erythropoietin receptor, Brain, 133: 2281-2294, 2010.
Rønn et al., A simple procedure for quantification of neurite outgrowth based on stereological principles, J. Neurosci. Methods, 100: 25-32, 2000.
Sah et al., Interaction of NPY compounds with the rat glucocorticoid-induced receptor (GIR) reveals similarity to the NPY-Y2 receptor, Peptides, 28: 302-309, 2007.
Vandenberghe et al., Novel adeno-associated viral vectors for retinal gene therapy, Gene Therapy, 19: 162-168, 2012.
Sly, W. et al., Brain-directed gene therapy for lysosomal storage disease: Going well beyond the blood-brain barrier, PNAS, 99(9): 5760-5762, Apr. 30, 2002.

* cited by examiner

*Primary Examiner* — Olga N Chernyshev
(74) *Attorney, Agent, or Firm* — Dinsmore & Shohl LLP

(57) ABSTRACT

The present invention discloses peptide fragments derived from neuropeptide Y (NPY), which are capable of selective binding to the neural cell adhesion molecule (NCAM) and inducing neuroplastic and neuroprotective effects, and the use of said peptide fragments as neuritogenic agents for treatment of pathological conditions in which neuroprotection and neuroplastic changes are desired, such as brain and retina disorders.

11 Claims, 13 Drawing Sheets

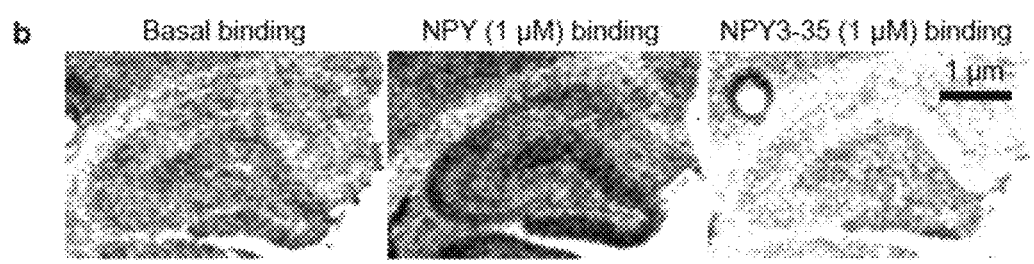
FIG. 2B
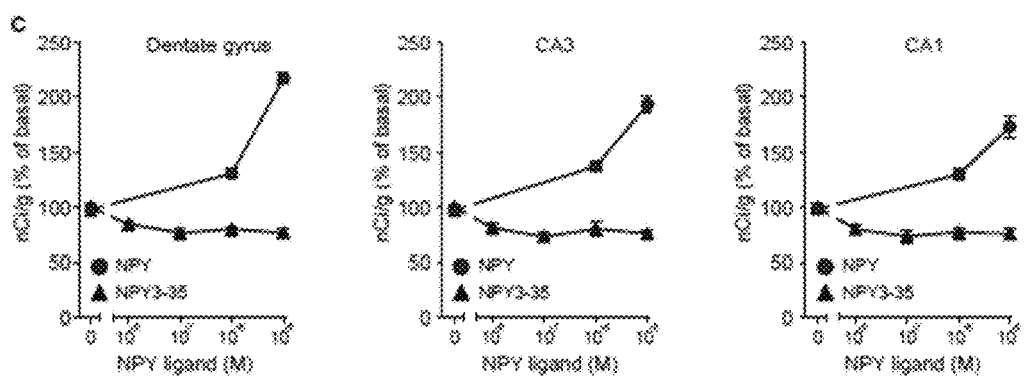
FIG. 2C
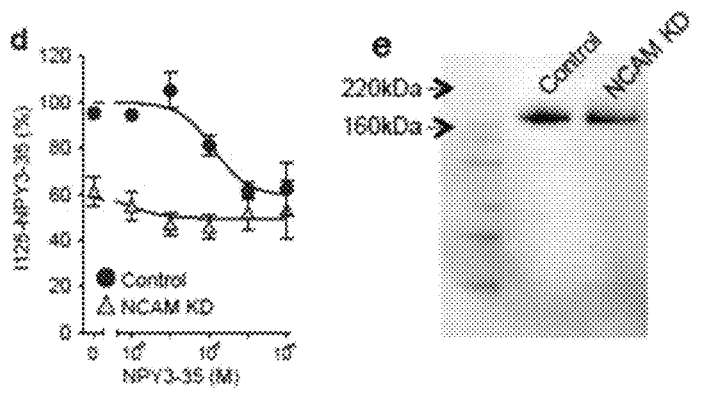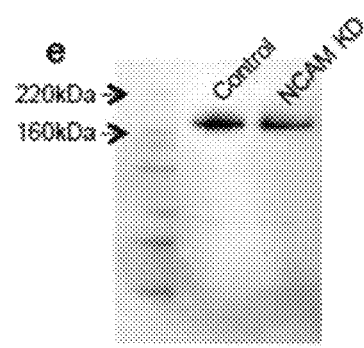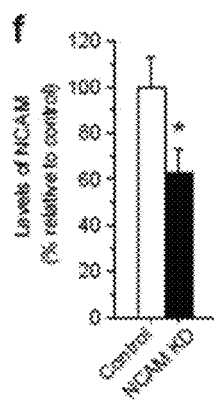
FIG. 2D  FIG. 2E  FIG. 2F

NEUROPEPTIDE Y-DERIVED PEPTIDES

FIELD OF INVENTION

The present invention provides neuropeptide Y (NPY)-derived peptide fragments and their use for treating diseases and disorders of the eye and central nervous system.

BACKGROUND OF INVENTION

Neuropeptide Y (NPY) is a 36 amino acid-long polypeptide (NPY1-36; SEQ ID NO:22) widely distributed in the central and peripheral nervous system of mammals. NPY is the most abundant neuropeptide in the brain and is known to induce vasoconstriction, to inhibit noradrenaline release at a pre-synaptic level, and to regulate diverse functions including blood pressure, stress, pain, hormone secretion, reproduction, circadian rhythm and food intake. NPY has been implicated in feeding disorders, epilepsy, hypertension, pain disorders, depression and anxiety.

NPY is known to bind and stimulate receptors belonging to the GPCR family, also known as seven-transmembrane receptors (7TM); including Y1, Y2, Y3, Y4, Y5 and Y6 (aka y6). In the central nervous system, NPY predominantly acts via Y1, Y2 and Y5. These 7TM receptors display different affinities for full-length NPY and N-terminally truncated fragments thereof such as NPY3-36; a physiological cleavage product which loses affinity for the Y1 receptor to become an Y2/Y5 receptor agonist. NPY is known to exert neuroprotective and neurogenic effects reported to occur via activation of the GPCR NPY-receptors.

Nyce et al (U.S. Pat. No. 6,426,330) discloses NPY fragments of between 8 to 18 amino acids in length with a D-Thr amino acid substitution of the Thr32 position. A few specific peptide sequences are mentioned comprising the most C-terminal amino acid at position 36 of NPY, such as NPY27-36. The peptides are used for inducing satiety and lowering blood pressure.

During et al. (US2010/0168215) discloses expression vectors comprising a nucleic acid encoding NPY or a functional fragment thereof. The vector is for treating a neurological disease. The functional fragment of NPY is defined as retaining activity of full length NPY, namely being capable of binding to cognate NPY-receptors (especially Y2).

Specific fragments include NPY2-36, NPY13-36, NPY16-36 and NPY18-36, thus the disclosed fragments include the most C-terminal amino acid at position 36 of NPY.

Boublik et al (U.S. Pat. No. 5,026,685 and U.S. Pat. No. 5,328,899) discloses NPY analogues (NPY19-36 and NPY 17-36, respectively) shortened at the N-terminus, and their use i.a. for lowering blood pressure.

Abid et al. (J Biol Chem Vol 284, No 37, pp. 24715-24724, 2009) discloses that NPY1-36 is rapidly cleaved in serum to produce three main fragments namely NPY3-36, NPY3-35 and NPY2-36. NPY3-35 is shown to be unable to bind NPY Y1, Y2 and Y5 receptors and thus it is concluded to represent the major metabolic clearance product of the Y2/Y5 agonist NPY3-36.

Current clinical trials involving NPY are largely focused on treating obesity although its more recently discovered neuroprotective and neurogenic effects make it a potential candidate for treating nervous system disorders including depression, Alzheimer's disease, Parkinson's disease and epilepsy. However, NPY-based treatments have a range of potential serious adverse effects because of the broad functions exerted by the various GPCR NPY-receptors targeted: As an example, targeting Y1 via NPY is likely to cause hypertension, anxiety, depression and altered pain perception.

SUMMARY OF INVENTION

NPY is known to bind to and exert its various biological effects through NPY receptors Y1-Y6. NPY as an Y1-Y6 ligand or agonist is dependent on amino acid residue 36 (Tyr36), which position is amidated. It has previously been shown that NPY not comprising Tyr36 lacks the classical NPY effects such as on food intake which is mediated through the classical or cognate NPY-receptors (Y1-Y6). Also, NPY3-35 is known in the art as a degradation product with no biological effects through the known NPY-receptors.

The present inventors have now surprisingly found that not only NPY/NPY1-36 (SEQ ID NO:22) but in particular specified peptide fragments thereof not comprising Tyr36, including fragments such as NPY3-35 (SEQ ID NO:1), bind to NCAM (neural cell adhesion molecule), an interaction that has not previously been identified. Specifically, NPY and specified fragments thereof according to the present invention, bind predominantly to the Ig1 module of NCAM, in the area where two NCAM molecules would otherwise interact.

This new finding of an interaction with NCAM potentially holds promise of achieving new effects of specified NPY fragments, which effects may be achieved even in the absence of Tyr36 of NPY1-36. Without residue Tyr36, the NPY fragments will not bind to and activate the cognate NPY-receptors thus effectively avoiding the risk of adverse effects through general activation of Y1-Y6 receptors.

The present inventors have surprisingly found that specified NPY peptides according to the present invention have several neuronal effects, which have not previously been associated with such NPY peptides, namely stimulating neuritogenesis, increasing neuronal survival and neuroplasticity.

These properties make the NPY fragments of the present invention potentially useful for treatment of a range of diseases and disorders where neuritogenic, neuroplastic and neuroprotective effects are desired, in particular disorders of the central nervous system or brain, and the eye or retina/optic nerve.

Surprisingly, the NPY peptides according to the present invention are even more potent that full-length NPY with respect to at least inducing neuritogenesis, and with respect to neuroprotection. Furthermore, the NPY peptides according to the present invention surprisingly increase or enhance long-term potentation, whereas full-length NPY even has the opposite effect.

Thus, provided herein is an isolated peptide consisting of a peptide sequence of from 15 to 33 contiguous amino acid residues derived from neuropeptide Y (NPY) (SEQ ID NO:22), wherein said peptide comprises the sequence YSALRHYINLITRQR (NPY21-35; SEQ ID NO:19), or a functional variant having at least 60% sequence identity to SEQ ID NO:19, wherein said peptide does not comprise the Tyr amino acid of position 36 of SEQ ID NO:22, for use in a method of treating a disease or disorder of the central nervous system and/or the eye.

Said peptide for use in a method of treating a disease or disorder of the central nervous system and/or the eye may be selected from the group consisting of SEQ ID NOs: 1-19 (NPY3-35 to NPY21-35), or a functional variant thereof having at least 60% sequence identity thereto.

Also provided herein is an isolated peptide consisting of a peptide sequence of 15 to 32 contiguous amino acid residues derived from neuropeptide Y (NPY) (SEQ ID NO:22), wherein said peptide comprises the sequence YSALRHYINLITRQR (NPY21-35; SEQ ID NO:19), or a functional variant having at least 60% sequence identity to SEQ ID NO:19, wherein said peptide does not comprise the Tyr amino acid of position 36 of NPY (SEQ ID NO:22).

Said isolated peptide may be selected from the group consisting of SEQ ID NOs: 2-19 (NPY4-35 to NPY21-35), or a functional variant thereof having at least 60% sequence identity thereto.

The NPY-fragment peptides according to the present invention may be formulated as a monomer, or as a multimer comprising two, three, four or more peptides.

It is also an aspect of the present invention to provide a nucleic acid construct encoding a peptide consisting of a peptide sequence of from 15 to 33 contiguous amino acid residues derived from neuropeptide Y (NPY) (SEQ ID NO:22), wherein said peptide comprises or consists of the sequence YSALRHYINLITRQR (NPY21-35; SEQ ID NO:19), or a functional variant having at least 60% sequence identity to SEQ ID NO:19, wherein said peptide does not comprise the Tyr amino acid of position 36 of SEQ ID NO:22; and also their use in a method of treating a disease or disorder of the central nervous system and/or the eye.

Said nucleic acid construct may be comprised in a delivery vehicle, such as a delivery vector, such as a viral vector. Said viral vector may be a recombinant adeno-associated virus (rAAV) vector.

The disease or disorder of the eye to be treated according to the present invention is preferably a retinal or optic nerve disease or disorder. Said retinal or optic nerve disorder may be selected from the group consisting of retinal detachment, retinopathies including diabetic, radiation and hypertension retinopathies, macular degeneration such as age-related macular degeneration (AMD) of any stage, retinitis pigmentosa, cone-rod dystrophy, glaucoma, optic neuropathies, Leber's congenital amaurosis (LCA), lipemia retinalis, eye injury, angioid streaks, myopic degeneration, retinal vein and artery occlusion, ocular ischemic syndrome, uveitis/vasculitis, and cancers of the retina including retinoblastoma and metastatic eye cancer.

For the treatment of retinal or optic nerve disorders, said peptide or nucleic acid construct encoding said peptide, may be administered directly into the eye by means of intravitreal or subretinal administration.

The peptide or nucleic acid construct encoding said peptide of the invention may also be used for treatment of a disease or disorder of the central nervous system, including neurodegenerative disorder such as Parkinson's disease, Alzheimer's disease, Huntington's disease Amyotrophic lateral sclerosis (ALS), spinocerebellar ataxias, Multiple Sclerosis, and other polyglutamine diseases.

The peptide or nucleic acid construct encoding said peptide of the invention may also be used for treatment of a disease or disorder of the central nervous system, including stroke, epilepsy and peripheral nerve lesion.

For the treatment of CNS disorders, said peptide or nucleic acid construct encoding said peptide may be administered directly into the brain or brain area by means of intracerebral or intrathecal administration.

Figure 1:
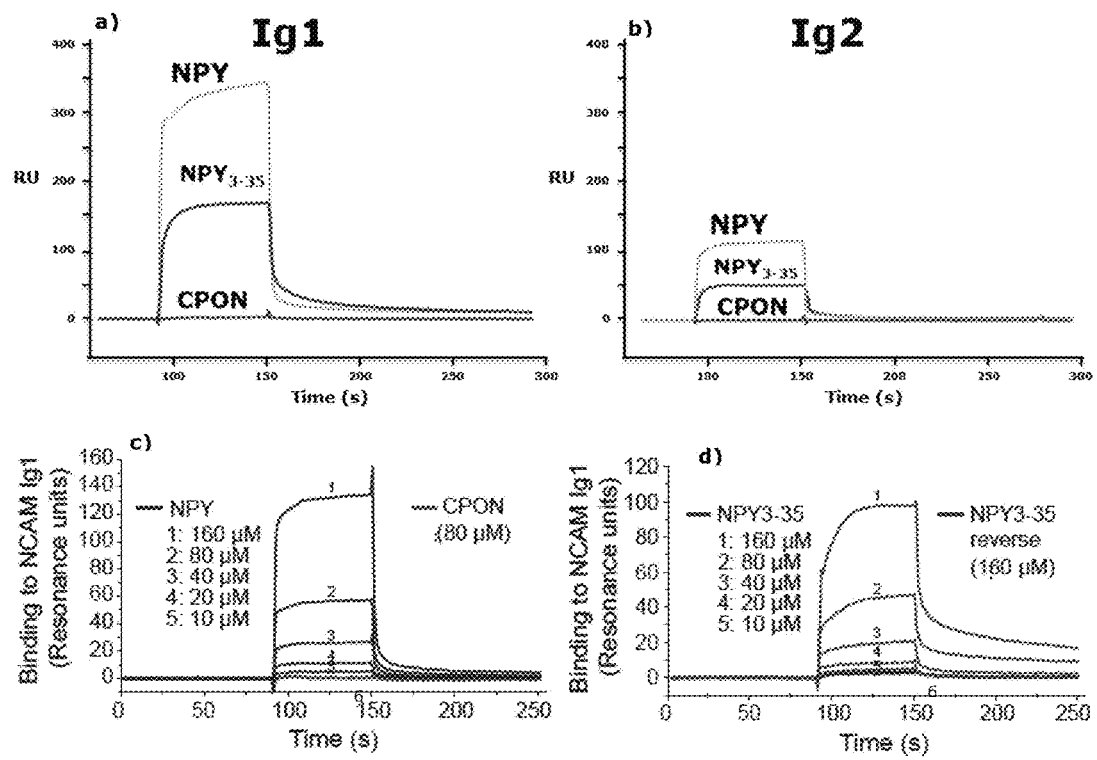
FIG. 1: SPR measurement of NPY and NPY3-35 binding to NCAM. The Ig1 or Ig2 module of NCAM was immobilized on a sensor chip and a series of peptide fragments of NPY or NPY antagonists injected to obtain binding and dissociation curves by use of surface plasmon resonance (SPR) (Biacore 2000). CPON=C-Flanking Peptide of Neuropeptide Y, RU=resonance units. (a) NPY and NPY3-35 binds to the NCAM Ig1-module. (b) NPY and NPY3-35 binds to the Ig2-module. (c) NCAM Ig1 was coupled to the chip and binding to NPY was measured in a concentration range between 10 μM and 160 μM (1-5). CPON at a concentration of 80 μM was used as a negative control (6). (d) NCAM Ig1 was coupled to the chip and binding to NPY3-35 was measured in a concentration range between 10 μM and 160 μM (1-5). A peptide with the reverse aminoacid sequence of NPY3-35 was used as a negative control (6).

The Morris Water Maze test: Reference memory training consisted of 3 consecutive trials daily for 3 days. Each trial started with the animal being placed in the water facing the wall of the pool. The starting position differed for each trial but was identical for all animals. In each trial, the animal was allowed 90 s to locate the platform. On the first 3 days immediately after training, the animals were given a 4 µl intracerebroventricular injection of either NPY3-35 (10 nmol) or saline. To test for the effects on long-term memory, the animals were given a 60 s probe trial 24 h, 1 and 2 weeks after reference memory training. In the probe trials, the platform was removed, and the animals started from a position in a quadrant adjacent to the original platform quadrant. Subsequently, after the 24 h and 1 wk probe trial, the animal was given one relearning trial under conditions identical to reference memory training to counteract memory extinction. NPY3-35 (10 nmol; indicated by arrows) improved the memory in rats as seen by lower latency times in the Morris Water maze task (a), and increased searching time in the platform quadrant in the probe test 2 weeks later (b). The memory enhancing effect was abolished when soluble NCAM Ig1 module (10 nmol) was injected together with NPY3-35, consistent with the NCAM specific effect of NPY3-35. *: $p<0.05$, **$p<0.01$ (Student's t-test, two-tailed, n=15-20 in each group). (c-d) NPY3-35 facilitates hippocampal upregulations in synaptic proteins 24 hours after three training trials and a single ICV injection. (c) Synaptotagmin, pCaMKII, sphinophilin, PSD-95 and AMPAR GluR2 subunit were all found to be upregulated, whereas synapsin1, synaptophysin, PKCalfa, GluR1 and NMDR were unaffected. *: $p<0.05$, (Student's t-test, two-tailed, n=5 in each group) (d) Immunoblots corresponding to data in (c). (e-f) The improved memory after NPY3-35 treatment was blocked by adding Ig1-module (disrupts binding to NCAM) and lasted at least 2 weeks (end of experiment) as shown by better performance in a classical probe test. *$P<0.05$, **$P<0.01$ vs. vehicle, Bonferroni post-hoc test after significant ANOVA.

Figure 15:
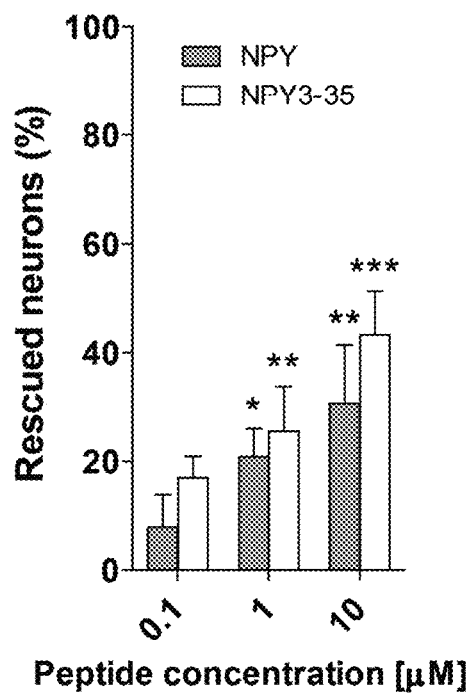

FIG. 15: Neuroprotective effects of NPY and NPY3-35 in kainate treated neurons. Neuropetide Y (NPY1-36) and NPY3-35 protects hippocampal neurons against kainate-induced excitotoxicity. Hippocampal neurons from rat embryos, embryonic stage day 19, were cultivated for 7 days before incubation with 300 µM kainate for 24 hrs. NPY or NPY3-35 was added 1 hour before kainate addition. Data are shown as mean values±SEM (n=8). 100% corresponds to untreated controls and 0% corresponds to kainate treated cultures. *$P<0.05$, $P<0.01$, *$P<0.001$, repeated-measures one-way ANOVA with Dunnett's post-hoc test versus kainate treated cultures.

Figure 16:
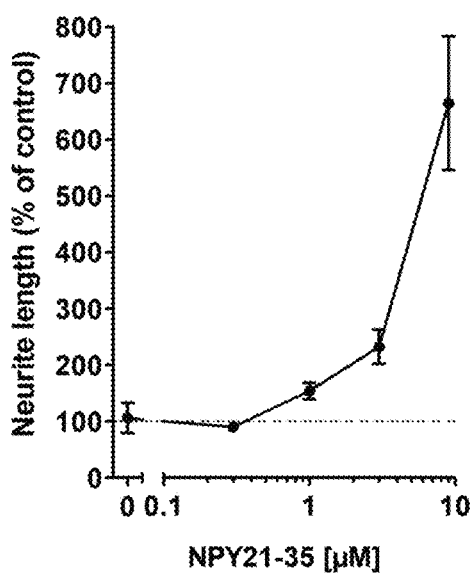

FIG. 16: NPY21-35 induce neurite outgrowth in E19 prenatal rat hippocampal cultures (24 h). This peptide is the shortest peptide that induces neuritogenesis as a monomer, when amino acids are removed successively from the N-terminus of NPY3-35. I.e. NPY3-35 to NPY21-35 induce neuritogenesis, while i.a. NPY22-35 does not (cf. example 2 for further data of neuritogenic effects of specified fragments).

DEFINITIONS AND ABBREVIATIONS

Affinity: the strength of binding between receptors and their ligands.

The term "agonist" in the present context refers to a peptide as defined herein, capable of binding to and activating a receptor.

The term "Individual" refers to vertebrates, particular members of the mammalian species, preferably primates including humans. As used herein, 'subject' and 'individual' may be used interchangeably.

A "polypeptide", "peptide" or "protein" is a polymer of amino acid residues preferably joined exclusively by peptide bonds, whether produced naturally or synthetically. The term "polypeptide" as used herein covers proteins, peptides and polypeptides, wherein said proteins, peptides or polypeptides may or may not have been post-translationally modified. A peptide is usually shorter in length than a protein, and single-chained.

An "isolated polypeptide" is a polypeptide separated and/or recovered from a component of their natural, typically cellular, environment, that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, tetramers or alternatively glycosylated or derived forms.

An "amino acid residue" can be a natural or non-natural amino acid residue linked peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 1 herein below. Non-natural amino acids are those not listed in Table 1. Also, non-natural amino acid residues include, but are not limited to, modified amino acid residues, L-amino acid residues, and stereoisomers of D-amino acid residues.

TABLE 1

Natural amino acids and their respective codes.

| Symbols | | |
|---|---|---|
| 1-Letter | 3-Letter | Amino acid |
| Y | Tyr | tyrosine |
| G | Gly | glycine |

TABLE 1-continued

Natural amino acids and their respective codes.

| Symbols | | Amino acid |
|---|---|---|
| 1-Letter | 3-Letter | |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers in one embodiment to the following classes: 1) HRK, 2) DENQ, 3) C, 4) STPAG, 5) MILV and 6) FYW.

Within the meaning of the term "equivalent amino acid substitution" as applied herein, one amino acid may be substituted for another, in one embodiment, within the groups of amino acids indicated herein below:
i) Amino acids having polar side chains (Asp, Glu, Lys, Arg, His, Asn, Gln, Ser, Thr, Tyr, and Cys)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

In the present context the standard one-letter code for amino acid residues as well as the standard three-letter code is applied. Abbreviations for amino acids are in accordance with the recommendations in the IUPAC-IUB Joint Commission on Biochemical Nomenclature Eur. J. Biochem, 1984, vol. 184, pp 9-37. Throughout the application either the three letter code or the one letter code for natural amino acids are used. Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

A "Bioactive agent" (i.e., biologically active substance/agent) is any agent, drug, compound, composition of matter or mixture which provides some pharmacologic, often beneficial, effect that can be demonstrated in-vivo or in vitro. It may refer to the peptide sequences according to the present invention, compounds or compositions comprising these and nucleic acid constructs encoding said peptides. As used herein, this term further includes any physiologically or pharmacologically active substance that produces a localized or systemic effect in an individual. Further examples of bioactive agents include, but are not limited to, agents comprising or consisting of an oligosaccharide, agents comprising or consisting of a polysaccharide, agents comprising or consisting of an optionally glycosylated peptide, agents comprising or consisting of an optionally glycosylated polypeptide, agents comprising or consisting of a nucleic acid, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites. It may be used either prophylactically, therapeutically, in connection with treatment of an individual, such as a human or any other animal.

The terms "drug", "medicament" as used herein include biologically, physiologically, or pharmacologically active substances that act locally or systemically in the human or animal body.

The terms "treatment" and "treating" as used herein refer to the management and care of a patient for the purpose of combating a condition, disease or disorder. The term is intended to include the full spectrum of treatments for a given condition from which the patient is suffering, and refer equally to curative therapy, prophylactic or preventative therapy and ameliorating or palliative therapy, such as administration of the peptide or composition for the purpose of: alleviating or relieving symptoms or complications; delaying the progression of the condition, partially arresting the clinical manifestations, disease or disorder; curing or eliminating the condition, disease or disorder; amelioration or palliation of the condition or symptoms, and remission (whether partial or total), whether detectable or undetectable; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The term "palliation", and variations thereof, as used herein, means that the extent and/or undesirable manifestations of a physiological condition or symptom are lessened and/or time course of the progression is slowed or lengthened, as compared to not administering compositions of the present invention.

The individual to be treated is preferably a mammal, in particular a human being. Treatment of animals, such as mice, rats, dogs, cats, cows, horses, sheep and pigs, is, however, also within the scope of the present invention.

An "individual in need thereof" refers to an individual who may benefit from the present invention. In one embodiment, said individual in need thereof is a diseased individual, wherein said disease may be a disease or disorder of the CNS and/or eye.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

A treatment according to the invention may be prophylactic, ameliorating or curative.

"Pharmacologically effective amount", "pharmaceutically effective amount" or "physiologically effective amount" of a "bioactive agent" is the amount of an active agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered. The precise amount will depend upon numerous factors, e.g., the active agent, the activity of the composition, the delivery device employed, the physical characteristics of the composition, intended patient use (i.e. the number of doses administered per day), patient considerations, and the like, and can readily be determined by one skilled in the art, based upon the information provided herein. An "effective amount" of a bioactive agent can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 100%.

"Co-administering" or "co-administration" of bioactive agents/peptides of the invention and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 72 hours, such as 48 hours, for example less than 24 hours, such as less than 12 hours, for example less than 6 hours, such as less than 3 hours. However, these terms also mean that the bioactive agent and a therapeutic composition can be administered together.

Due to the imprecision of standard analytical methods, molecular weights and lengths of polymers are understood to be approximate values. When such a value is expressed as "about" X or "approximately" X, the stated value of X will be understood to be accurate to +/−20%, such as +/−10%, for example +/−5%.

DETAILED DESCRIPTION OF THE INVENTION

Pro-neuropeptide Y is a 97-amino acid long peptide (SEQ ID NO:32) which is cleaved into the following 2 chains: Neuropeptide Y (alternative name: neuropeptide tyrosine), and C-flanking peptide of NPY (Short name=CPON: SEQ ID NO:33).

Neuropeptide Y (NPY; NPY1-36; SEQ ID NO:22) is a highly conserved 36-amino acid endogenous peptide neurotransmitter, the most abundant neuropeptide in the brain and the autonomic nervous system of humans. Classically, the effects of NPY1-36 are mediated through binding to cognate NPY-receptors with varying degree. AT least six NPY receptors have been identified so far; Y1, Y2, Y3, Y4, Y5 and Y6; five NPY receptors in mammals: Y1, Y2, Y4, Y5 and Y6 (or y6; used interchangeably herein). They are G-protein coupled receptors belonging to the 7TM (7 transmembrane domains) family.

These receptors display different affinities for different forms of NPY. The Y1 receptor has highest affinity for full-length NPY, while Y2 and Y5 bind and are stimulated by full-length NPY and N-terminally truncated NPY. The physiological effects associated with the Y1 and Y2 receptors are the best known; exposure to a Y1 agonist causes an increase in blood pressure and potentiates postsynaptically the action of other vasoactive substances, whereas Y2 receptors are mainly located presynaptically, and upon stimulation mediate the inhibition of neurotransmitter release. Moreover, Y2 exerts a negative-feedback pathway in that its activation by NPY or NPY fragments in turn negatively regulates NPY release.

NPY is a prototype of peptide whose function can be altered by proteases. Among peptidases displaying a high affinity for NPY, the primary role appears to be played by serine-type protease dipeptidyl peptidase IV (CD26) that releases an N-terminal dipeptide. By cleaving the N-terminal Tyr-Pro dipeptide off NPY CD26 generates NPY3-36, a truncated form that loses its affinity for the Y1 receptor and becomes a Y2/Y5 receptor agonist. NPY can also be degraded by aminopeptidase P (AmP) by removing the N-terminal tyrosine from NPY to generate NPY2-36, a selective Y2 agonist. It has been indicated that the 36th, 35th, and 33rd residues of NPY analogues may also be removed by carboxypeptidases.

In addition to the brain, NPY and its receptors are expressed throughout the body, both in the central nervous system (CNS) and in the sympathetic nervous system. NPY regulates cardiovascular and other sympathetic functions together with norepinephrine. NPY displays vasoconstrictor activity exerted by inhibiting $Ca^{2+}$-activated $K^+$ channels in vascular smooth muscle, and it has been implicated in the control of blood pressure, sexual behaviour, food intake, neurological disorders, alcoholism, bone physiology, regulation of energy, circadian rhythms, balance, memory and learning.

Further, NPY plays an important role in mood disorders, anxiety, epilepsy and depression. Central NPY levels in the cerebrospinal fluid are low in subjects suffering from depression and correlate inversely with anxiety. Anti-depressant-like effects can be achieved in mice by administering a Y2 antagonist or a Y1 agonist. Y1 has also been implicated in the mediation of adult neuronal proliferation and hippocampal neurogenesis. Importantly, the effects of NPY are commonly accepted to be a result of its interactions with its 7TM receptors.

Because NPY and the 7TM receptors are thought to be involved in so many pathways, NPY-based treatments such as treatments involving receptor agonists are likely to cause severe pleiotropic effects, such as obesity, anxiety and hypertension.

NPY1-36 is characterised by C-terminal amidation of amino acid at position 36 (Tyr36), which amino acid position and its amidation is important for its classical binding to the cognate NPY-receptors (Y1-Y6/y6) (Berglund et al. 2003).

Interestingly, the present inventors have now identified herein a hitherto unknown interaction between NPY and NCAM (Neural Cell Adhesion Molecule). This novel interaction with NCAM is shown herein not only for full-length NPY1-36 and certain N-terminally truncated fragments, but to a greater extent for specified NPY fragments not comprising Tyr36, including NPY3-35 (SEQ ID NO:1). This interaction is shown herein to occur predominantly through binding to the Ig1 module of NCAM (i.e. where two NCAM molecules usually interact—NCAM homophilic cis-interaction). No binding is observed to the Ig3 module of NCAM.

NPY1-36 retains its binding capability to its cognate NPY-receptors (Y1-Y6) besides the new interaction with NCAM. However, the peptide fragments of the present invention not comprising Tyr36 (SEQ ID NOs: 1-19), including NPY3-35 (SEQ ID NO:1), interacts with NCAM without a concomitant binding of the cognate NPY-receptors. This may largely be due to the lack of Tyr36 of SEQ ID NOs: 1-19.

Thus, both NPY1-36 and peptide fragments of the present invention in some embodiments not comprising Tyr36 (SEQ ID NOs: 1-19), including NPY3-35, bind to NCAM, and there are overlapping biological effects associated with this binding to a certain degree. However, SEQ ID NOs: 1-19 binds to NCAM without a concomitant binding to and stimulation of the cognate NPY-receptors. Thus, the SEQ ID NOs: 1-19-NCAM binding is highly specific. This holds great potential in reducing the risk of adverse effects associated with administering NPY1-36, by avoiding the general activation of the cognate NPY-receptors.

Thus, SEQ ID NOs: 1-19, and functional variants thereof are potential new candidates for a much more specific induction of neuroprotective and neurogenic effects. This holds true even for NPY3-35 (SEQ ID NO:1) which has hitherto been regarded as an inactive degradation product of NPY.

Neural Cell Adhesion Molecule (NCAM)

NCAM is a homophilic binding glycoprotein expressed on the surface of neurons, glia, skeletal muscle and natural killer cells. NCAM has been implicated as having a role in cell-cell adhesion, neurite outgrowth, synaptic formation and plasticity, path-finding of axons, early synaptogenesis, synaptic maturation and learning and memory. Many aspects of neuronal development involve cell-cell adhesion mechanisms; these include neuronal cell migration, axon-bundle and synapse formation, formation of glial networks surrounding axons and synapses.

NCAM is a member of the Ig superfamily Cell Adhesion Molecules (CAMs) and is found predominantly in the synapses. Evidence suggests that NCAM mediates neuritogenesis by signalling via the Fibroblast growth factor receptor (FGFR) and the p59Fyn signalling pathway. NCAM comprises five Ig-like domains (Ig1, Ig2, Ig3, Ig4 and Ig5) and two fibronectin type III (FNIII) repeats. NCAM is known to have heterophilic and homophilic interactions with various ligands at the synapses. The different domains of NCAM have different roles, with the Ig domains being involved in homophilic (NCAN-NCAM) binding, while the FNIII domains are involved in signalling leading to neurite outgrowth.

Alternative splicing of NCAM results in at least 27 isoforms, of which the main three vary only by their cytoplasmic domain: NCAM-120 kDa (GPI anchored); NCAM-140 kDa (short cytoplasmic domain); NCAM-180 kDa (long cytoplasmic domain). NCAM can also be modified by the insertion of minor exons, which can modulate its activities. NCAM can further be modified by the addition to its fifth Ig domain of the negatively charged, polysialic acid (PSA) which appears to play an important role in the synapse formation mediated by NCAM. PSA has indeed been shown to be important for long-term potentiation (LTP). NCAM further interacts with to brain derived neurotrophic factor (BDNF) and to Glial cell-derived neurotrophic factor (GDNF).

Peptides of the Present Invention

The present inventors have identified novel NPY fragments and surprisingly found that the NPY peptides according to the present invention have several neuronal effects, which effects have not previously been associated with such NPY peptides, namely i) Neuritogenic properties, e.g. are capable of stimulating neurite outgrowth, ii) Neuroprotective properties, e.g. are capable of enhancing neuronal cell survival/neuroprotection, and iii) Neuroplastic effects, e.g. having an effect on LTP (long-term potentiation) and memory consolidation.

These properties make the NPY fragments of the present invention potentially useful for treatment of a range of diseases and disorders where neuritogenic, neuroplastic and/or neuroprotective effects are desired, in one embodiment disorders of the central nervous system or brain, and the eye especially the retina and optic nerve.

These effects on neurons surprisingly occur through a specific and new interaction with NCAM, and not via the cognate NPY-receptors.

Thus, the NPY peptides according to the present invention in one embodiment are capable of interacting (i.e. interacts)

with and/or binding to NCAM. In one embodiment the NPY peptides according to the present invention are capable of interacting with and/or binding to NCAM via the Ig1 module, and/or the Ig2 module of NCAM, and/or not the Ig3 module of NCAM.

In another embodiment, the NPY peptides according to the present invention do not bind to and/or do not stimulate or activate the cognate NPY-receptors. In one embodiment said cognate NPY-receptors comprise G-protein coupled receptors, in one embodiment receptors Y1, Y2 and/or Y5.

In one embodiment the NPY peptides according to the present invention are potent inducers of neuritogenesis, and/or neuroprotectors.

In one embodiment the NPY peptides according to the present invention increase or enhance LTP.

Peptide for Use

It is an aspect of the present invention to provide an isolated peptide consisting of a peptide sequence of from 15 to 33 contiguous amino acid residues derived from neuropeptide Y (NPY) (SEQ ID NO:22),
wherein said peptide comprises or consists of the sequence YSALRHYINLITRQR (NPY21-35; SEQ ID NO:19), or a functional variant having at least 60% sequence identity to SEQ ID NO:19,
wherein said peptide does not comprise the Tyr amino acid of position 36 of SEQ ID NO:22,
for use in a method of treating a disease or disorder of the central nervous system and/or the eye.

The terms 'peptide' and 'isolated peptide' may be used interchangeably herein. The terms 'variant' and 'functional variant' may be used interchangeably herein.

It is also an aspect of the present invention to provide a peptide consisting of 15 to 33 contiguous amino acid residues derived from neuropeptide Y (NPY) (SEQ ID NO:22), wherein said peptide comprises at least the sequence YSALRHYINLITRQR (NPY21-35; SEQ ID NO:19), or a variant thereof,
wherein said peptide does not comprise the Tyr amino acid of position 36 of SEQ ID NO:22,
for use in a method of treating a disease or disorder of the central nervous system and/or the eye.

In one embodiment there is provided provide a peptide consisting of 15 to 33 contiguous amino acid residues derived from neuropeptide Y (NPY) (SEQ ID NO:22), said peptide comprising at least the sequence YSALRHYINLITRQR (NPY21-35; SEQ ID NO:19), or a variant thereof, said peptide not comprising the Tyr amino acid of position 36 of SEQ ID NO:22, wherein said peptide is selected from the group consisting of:

(NPY3-35, SEQ ID NO: 1)
SKPDNPGEDAPAEDMARYYSALRHYINLITRQR, (NPY4-35, SEQ ID NO: 2)
KPDNPGEDAPAEDMARYYSALRHYINLITRQR, (NPY5-35, SEQ ID NO: 3)
PDNPGEDAPAEDMARYYSALRHYINLITRQR, (NPY6-35, SEQ ID NO: 4)
DNPGEDAPAEDMARYYSALRHYINLITRQR, (NPY7-35, SEQ ID NO: 5)
NPGEDAPAEDMARYYSALRHYINLITRQR, (NPY8-35, SEQ ID NO: 6)
PGEDAPAEDMARYYSALRHYINLITRQR,

-continued
(NPY9-35, SEQ ID NO: 7)
GEDAPAEDMARYYSALRHYINLITRQR, (NPY10-35, SEQ ID NO: 8)
EDAPAEDMARYYSALRHYINLITRQR, (NPY11-35, SEQ ID NO: 9)
DAPAEDMARYYSALRHYINLITRQR, (NPY12-35, SEQ ID NO: 10)
APAEDMARYYSALRHYINLITRQR, (NPY13-35, SEQ ID NO: 11)
PAEDMARYYSALRHYINLITRQR, (NPY14-35, SEQ ID NO: 12)
AEDMARYYSALRHYINLITRQR, (NPY15-35, SEQ ID NO: 13)
EDMARYYSALRHYINLITRQR, (NPY16-35, SEQ ID NO: 14)
DMARYYSALRHYINLITRQR, (NPY17-35, SEQ ID NO: 15)
MARYYSALRHYINLITRQR, (NPY18-35, SEQ ID NO: 16)
ARYYSALRHYINLITRQR, (NPY19-35, SEQ ID NO: 17)
RYYSALRHYINLITRQR, (NPY20-35, SEQ ID NO: 18)
YYSALRHYINLITRQR,
and (NPY21-35, SEQ ID NO: 19)
YSALRHYINLITRQR, or a variant thereof,
for use in a method of treating a disease or disorder of the central nervous system and/or the eye.

A peptide that 'comprises or consist of' a sequence means that the peptide may either comprise the sequence, consist of the sequence, or comprise at least the full sequence. A peptide that 'comprises at least' a peptide sequence, such as 'comprising at least the sequence YSALRHYINLITRQR' means that the peptide will include all of the peptide sequence YSALRHYINLITRQR (NPY21-35; SEQ ID NO:19). It does, however, not exclude that additional components or amino acids may be present.

In one embodiment the peptide according to the present invention for use in a method of treating a disease or disorder of the central nervous system and/or the eye is a variant having at least 60% sequence identity to any one of SEQ ID NOs: 1 to 19, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to any one of SEQ ID NO: s 1 to 19.

In another embodiment, the peptide according to the present invention for use in a method of treating a disease or disorder of the central nervous system and/or the eye is a variant having at from 60 to 65% sequence identity, for example from 65 to 70% sequence identity, such as from 70 to 75% sequence identity, for example from 75 to 80% sequence identity, such as from 80 to 85% sequence identity, for example from 85 to 90% sequence identity, such as from 90 to 95% sequence identity, for example from 95 to 99% sequence identity to any one of SEQ ID NO: s 1 to 19.

In one embodiment, said peptide for use in a method of treating a disease or disorder of the central nervous system and/or the eye is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or
a functional variant having at least 60% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In another embodiment said peptide for use in a method of treating a disease or disorder of the central nervous system and/or the eye has at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

It follows that said peptide for use in a method of treating a disease or disorder of the central nervous system and/or the eye may in one embodiment have from 60% to 65 sequence identity, such as from 65 to 70% sequence identity, for example from 70 to 75% sequence identity, such as from 75 to 80% sequence identity, for example from 80 to 85% sequence identity, such as from 85 to 90% sequence identity, for example from 90 to 95% sequence identity, such as from 95 to 99% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In one embodiment the peptide according to the present invention for use in a method of treating a disease or disorder of the central nervous system and/or the eye is a variant having between 1-10 amino acid substitutions as compared to any one of SEQ ID NOs: 1 to 19, such as 1 amino acid substitution, for example 2 amino acid substitutions, such as 3 amino acid substitutions, for example 4 amino acid substitutions, such as 5 amino acid substitutions, for example 6 amino acid substitutions, such as 7 amino acid substitutions, for example 8 amino acid substitutions, such as 9 amino acid substitutions, for example 10 amino acid substitutions as compared to any one of SEQ ID NOs: 1 to 19.

In one embodiment the peptide according to the present invention for use in a method of treating a disease or disorder of the central nervous system and/or the eye is a variant having between 1-10 amino acid substitutions as compared to SEQ ID NO:19, such as 1 amino acid substitution, for example 2 amino acid substitutions, such as 3 amino acid substitutions, for example 4 amino acid substitutions, such as 5 amino acid substitutions, for example 6 amino acid substitutions, such as 7 amino acid substitutions, for example 8 amino acid substitutions, such as 9 amino acid substitutions, for example 10 amino acid substitutions as compared to SEQ ID NO:19.

In one embodiment, one or more, or all, of said amino acid substitutions are conservative amino acid substitutions.

It follows that in one embodiment a peptide variant of a sequence as defined herein is a functional variant, i.e. a variant retaining some biological function and/or activity associated with the native sequence. In one embodiment a peptide variant according to the present invention is capable of binding to NCAM. In one embodiment a variant is capable of binding to the NCAM Ig1 module. In one embodiment a variant does not bind to and/or activate Y1, Y2 and/or Y5.

In one embodiment, said peptide for use in a method of treating a disease or disorder of the central nervous system and/or the eye is SEQ ID NO: 1 (NPY3-35), or a functional variant thereof having at least 60% sequence identity to SEQ ID NO:1.

In one embodiment, said peptide for use in a method of treating a disease or disorder of the central nervous system and/or the eye is SEQ ID NO:2 (NPY4-35), or a functional variant thereof having at least 60% sequence identity to SEQ ID NO:2.

In one embodiment, said peptide for use in a method of treating a disease or disorder of the central nervous system and/or the eye is SEQ ID NO:3 (NPY5-35), or a functional variant thereof having at least 60% sequence identity to SEQ ID NO:3.

In one embodiment, said peptide for use in a method of treating a disease or disorder of the central nervous system and/or the eye is SEQ ID NO:4 (NPY6-35), or a functional variant thereof having at least 60% sequence identity to SEQ ID NO:4.

In one embodiment, said peptide for use in a method of treating a disease or disorder of the central nervous system and/or the eye is SEQ ID NO:5 (NPY7-35), or a functional variant thereof having at least 60% sequence identity to SEQ ID NO:5.

In one embodiment, said peptide for use in a method of treating a disease or disorder of the central nervous system and/or the eye is SEQ ID NO:6 (NPY8-35), or a functional variant thereof having at least 60% sequence identity to SEQ ID NO:6.

In one embodiment, said peptide for use in a method of treating a disease or disorder of the central nervous system and/or the eye is SEQ ID NO:7 (NPY9-35), or a functional variant thereof having at least 60% sequence identity to SEQ ID NO:7.

In one embodiment, said peptide for use in a method of treating a disease or disorder of the central nervous system and/or the eye is SEQ ID NO:8 (NPY10-35), or a functional variant thereof having at least 60% sequence identity to SEQ ID NO:8.

In one embodiment, said peptide for use in a method of treating a disease or disorder of the central nervous system and/or the eye is SEQ ID NO:9 (NPY11-35), or a functional variant thereof having at least 60% sequence identity to SEQ ID NO:9.

In one embodiment, said peptide for use in a method of treating a disease or disorder of the central nervous system and/or the eye is SEQ ID NO:10 (NPY12-35), or a functional variant thereof having at least 60% sequence identity to SEQ ID NO:10.

In one embodiment, said peptide for use in a method of treating a disease or disorder of the central nervous system and/or the eye is SEQ ID NO:11 (NPY13-35), or a functional variant thereof having at least 60% sequence identity to SEQ ID NO:11.

In one embodiment, said peptide for use in a method of treating a disease or disorder of the central nervous system and/or the eye is SEQ ID NO:12 (NPY14-35), or a functional variant thereof having at least 60% sequence identity to SEQ ID NO:12.

In one embodiment, said peptide for use in a method of treating a disease or disorder of the central nervous system and/or the eye is SEQ ID NO:13 (NPY15-35), or a functional variant thereof having at least 60% sequence identity to SEQ ID NO:13.

In one embodiment, said peptide for use in a method of treating a disease or disorder of the central nervous system and/or the eye is SEQ ID NO:14 (NPY16-35), or a functional variant thereof having at least 60% sequence identity to SEQ ID NO:14.

In one embodiment, said peptide for use in a method of treating a disease or disorder of the central nervous system and/or the eye is SEQ ID NO:15 (NPY17-35), or a functional variant thereof having at least 60% sequence identity to SEQ ID NO:15.

In one embodiment, said peptide for use in a method of treating a disease or disorder of the central nervous system and/or the eye is SEQ ID NO:16 (NPY18-35), or a functional variant thereof having at least 60% sequence identity to SEQ ID NO:16.

In one embodiment, said peptide for use in a method of treating a disease or disorder of the central nervous system and/or the eye is SEQ ID NO:17 (NPY19-35), or a functional variant thereof having at least 60% sequence identity to SEQ ID NO:17.

In one embodiment, said peptide for use in a method of treating a disease or disorder of the central nervous system and/or the eye is SEQ ID NO:18 (NPY20-35), or a functional variant thereof having at least 60% sequence identity to SEQ ID NO:18.

In one embodiment, said peptide for use in a method of treating a disease or disorder of the central nervous system and/or the eye is SEQ ID NO:19 (NPY21-35), or a functional variant thereof having at least 60% sequence identity to SEQ ID NO:19.

Peptide

It is also an aspect of the present invention to provide an isolated peptide consisting of a peptide sequence of 15 to 32 contiguous amino acid residues derived from neuropeptide Y (NPY) (SEQ ID NO:22),
wherein said peptide comprises or consist of the sequence YSALRHYINLITRQR (NPY21-35; SEQ ID NO:19), or a variant having at least 60% sequence identity to SEQ ID NO:19,
wherein said peptide does not comprise the Tyr amino acid of position 36 of NPY (SEQ ID NO:22).

The terms 'peptide' and 'isolated peptide' may be used interchangeably herein. The terms 'variant' and 'functional variant' may be used interchangeably herein.

It is also an aspect of the present invention to provide an isolated peptide consisting of a peptide sequence of 15 to 32 contiguous amino acid residues derived from neuropeptide Y (NPY) (SEQ ID NO:22),
wherein said peptide comprises at least the sequence YSALRHYINLITRQR (NPY21-35; SEQ ID NO:19), or a variant thereof,
wherein said peptide does not comprise the Tyr amino acid of position 36 of NPY (SEQ ID NO:22).

It one embodiment there is provided an isolated peptide consisting of a peptide sequence of 15 to 32 contiguous amino acid residues derived from neuropeptide Y (NPY) (SEQ ID NO:22),
said peptide comprising at least the sequence YSALRHYINLITRQR (NPY21-35; SEQ ID NO:19), or a variant thereof,
said peptide not comprising the Tyr amino acid of position 36 of NPY (SEQ ID NO:22),
wherein said peptide is selected from the group consisting of:

```
(NPY4-35, SEQ ID NO: 2)
KPDNPGEDAPAEDMARYYSALRHYINLITRQR, (NPY5-35, SEQ ID NO: 3)
PDNPGEDAPAEDMARYYSALRHYINLITRQR, (NPY6-35, SEQ ID NO: 4)
DNPGEDAPAEDMARYYSALRHYINLITRQR, (NPY7-35, SEQ ID NO: 5)
NPGEDAPAEDMARYYSALRHYINLITRQR, (NPY8-35, SEQ ID NO: 6)
PGEDAPAEDMARYYSALRHYINLITRQR, (NPY9-35, SEQ ID NO: 7)
GEDAPAEDMARYYSALRHYINLITRQR, (NPY10-35, SEQ ID NO: 8)
EDAPAEDMARYYSALRHYINLITRQR, (NPY11-35, SEQ ID NO: 9)
DAPAEDMARYYSALRHYINLITRQR, (NPY12-35, SEQ ID NO: 10)
APAEDMARYYSALRHYINLITRQR, (NPY13-35, SEQ ID NO: 11)
PAEDMARYYSALRHYINLITRQR, (NPY14-35, SEQ ID NO: 12)
AEDMARYYSALRHYINLITRQR, (NPY15-35, SEQ ID NO: 13)
EDMARYYSALRHYINLITRQR, (NPY16-35, SEQ ID NO: 14)
DMARYYSALRHYINLITRQR, (NPY17-35, SEQ ID NO: 15)
MARYYSALRHYINLITRQR, (NPY18-35, SEQ ID NO: 16)
ARYYSALRHYINLITRQR, (NPY19-35, SEQ ID NO: 17)
RYYSALRHYINLITRQR, (NPY20-35, SEQ ID NO: 18)
YYSALRHYINLITRQR,
and (NPY21-35, SEQ ID NO: 19)
YSALRHYINLITRQR,
``` or a variant thereof.

A peptide that 'comprises or consist of' a sequence means that the peptide may either comprise the sequence, consist of the sequence, or comprise at least the full sequence. A peptide that 'comprises at least' a peptide sequence, such as 'comprising at least the sequence YSALRHYINLITRQR' means that the peptide will include all of the peptide sequence YSALRHYINLITRQR (NPY21-35; SEQ ID NO:19). It does, however, not exclude that additional components or amino acids may be present.

In one embodiment the peptide according to the present invention is a variant having at least 60% sequence identity to any of SEQ ID NOs: 2 to 19, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to any one of SEQ ID NOs: 2 to 19.

In another embodiment, the peptide according to the present invention is a variant having at from 60 to 65% sequence identity, for example from 65 to 70% sequence identity, such as from 70 to 75% sequence identity, for example from 75 to 80% sequence identity, such as from 80 to 85% sequence identity, for example from 85 to 90% sequence identity, such as from 90 to 95% sequence identity, for example from 95 to 99% sequence identity to any one of SEQ ID NOs: 2 to 19.

In one embodiment, said peptide is selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or
a variant having at least 60% sequence identity to a peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In another embodiment said peptide has at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

It follows that said peptide may in one embodiment have from 60% to 65 sequence identity, such as from 65 to 70% sequence identity, for example from 70 to 75% sequence identity, such as from 75 to 80% sequence identity, for example from 80 to 85% sequence identity, such as from 85 to 90% sequence identity, for example from 90 to 95% sequence identity, such as from 95 to 99% sequence identity to a peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In one embodiment the peptide according to the present invention is a variant having between 1-10 amino acid substitutions as compared to any one of SEQ ID NOs: 2 to 19, such as 1 amino acid substitution, for example 2 amino acid substitutions, such as 3 amino acid substitutions, for example 4 amino acid substitutions, such as 5 amino acid substitutions, for example 6 amino acid substitutions, such as 7 amino acid substitutions, for example 8 amino acid substitutions, such as 9 amino acid substitutions, for example 10 amino acid substitutions as compared to any one of SEQ ID NOs: 2 to 19.

In one embodiment, one or more, or all, of said amino acid substitutions are conservative amino acid substitutions.

It follows that in one embodiment a peptide variant of a sequence as defined herein is a functional variant, i.e. a variant retaining some biological function and/or activity associated with the native sequence. In one embodiment a peptide variant according to the present invention is capable of binding to NCAM. In one embodiment a variant is capable of binding to the NCAM Ig1 module. In one embodiment a variant does not bind to and/or activate Y1, Y2 and/or Y5.

In one embodiment, the peptide according to the present invention does not comprise or consist of the amino acid sequence SKPDNPGEDAPAEDMARYYSALRHYIN-LITRQR (NPY3-35, SEQ ID NO: 1).

In one embodiment, the peptide according to the present invention does not comprise or consist of the amino acid sequence SKPDNPGEDAPAEDMARYYSALRHYIN-LITRQR (NPY3-35, SEQ ID NO: 1), unless used in a method of treating a disease or disorder of the central nervous system and/or the eye.

In one embodiment, the isolated peptide according to the present invention is SEQ ID NO:2 (NPY4-35), or a functional variant thereof having at least 60% sequence identity to SEQ ID NO:2.

In one embodiment, the isolated peptide according to the present invention is SEQ ID NO:3 (NPY5-35), or a functional variant thereof having at least 60% sequence identity to SEQ ID NO:3.

In one embodiment, the isolated peptide according to the present invention is SEQ ID NO:4 (NPY6-35), or a functional variant thereof having at least 60% sequence identity to SEQ ID NO:4.

In one embodiment, the isolated peptide according to the present invention is SEQ ID NO:5 (NPY7-35), or a functional variant thereof having at least 60% sequence identity to SEQ ID NO:5.

In one embodiment, the isolated peptide according to the present invention is SEQ ID NO:6 (NPY8-35), or a functional variant thereof having at least 60% sequence identity to SEQ ID NO:6.

In one embodiment, the isolated peptide according to the present invention is SEQ ID NO:7 (NPY9-35), or a functional variant thereof having at least 60% sequence identity to SEQ ID NO:7.

In one embodiment, the isolated peptide according to the present invention is SEQ ID NO:8 (NPY10-35), or a functional variant thereof having at least 60% sequence identity to SEQ ID NO:8.

In one embodiment, the isolated peptide according to the present invention is SEQ ID NO:9 (NPY11-35), or a functional variant thereof having at least 60% sequence identity to SEQ ID NO:9.

In one embodiment, the isolated peptide according to the present invention is SEQ ID NO:10 (NPY12-35), or a functional variant thereof having at least 60% sequence identity to SEQ ID NO:10.

In one embodiment, the isolated peptide according to the present invention is SEQ ID NO:11 (NPY13-35), or a functional variant thereof having at least 60% sequence identity to SEQ ID NO:11.

In one embodiment, the isolated peptide according to the present invention is SEQ ID NO:12 (NPY14-35), or a functional variant thereof having at least 60% sequence identity to SEQ ID NO:12.

In one embodiment, the isolated peptide according to the present invention is SEQ ID NO:13 (NPY15-35), or a functional variant thereof having at least 60% sequence identity to SEQ ID NO:13.

In one embodiment, the isolated peptide according to the present invention is SEQ ID NO:14 (NPY16-35), or a functional variant thereof having at least 60% sequence identity to SEQ ID NO:14.

In one embodiment, the isolated peptide according to the present invention is SEQ ID NO:15 (NPY17-35), or a functional variant thereof having at least 60% sequence identity to SEQ ID NO:15.

In one embodiment, the isolated peptide according to the present invention is SEQ ID NO:16 (NPY18-35), or a functional variant thereof having at least 60% sequence identity to SEQ ID NO:16.

In one embodiment, the isolated peptide according to the present invention is SEQ ID NO:17 (NPY19-35), or a functional variant thereof having at least 60% sequence identity to SEQ ID NO:17.

In one embodiment, the isolated peptide according to the present invention is SEQ ID NO:18 (NPY20-35), or a functional variant thereof having at least 60% sequence identity to SEQ ID NO:18.

In one embodiment, the isolated peptide according to the present invention is SEQ ID NO:19 (NPY21-35), or a functional variant thereof having at least 60% sequence identity to SEQ ID NO:19.

Peptide and Peptide for Use

The present inventors have surprisingly shown that the peptides according to the present invention bind to Neural Cell Adhesion Molecule (NCAM).

In one embodiment, the peptides according to the present invention are capable of binding to and/or interacting with and/or stimulating (or activating) Neural Cell Adhesion Molecule (NCAM).

When reference is made to a 'peptide', this term will encompass both references to a peptide per se, and also to a peptide for use according to the present invention.

In a particular embodiment, the present peptides bind to the NCAM Ig1 module. In a particular embodiment, the peptides bind to the NCAM Ig1 module and not the NCAM Ig3 module. In a particular embodiment, the peptides do not bind to the NCAM Ig3 module.

In one embodiment, the peptides of the invention do not bind to the cognate NPY-receptors. In one embodiment, the peptides do not bind to the cognate NPY-receptors Y1, Y2 and Y5.

In one embodiment, the peptides according to the present invention are capable of stimulating neurite outgrowth.

In one embodiment, the peptides according to the present invention are capable of promoting or stimulating or increasing the survival of neurons.

In one embodiment, the peptides according to the present invention are capable of enhancing long-term potentiation (LTP).

In one embodiment, the peptides according to the present invention are capable of regulating neuroplasticity.

In one embodiment, the peptides according to the present invention are capable of stimulating learning and memory.

According to the present invention, a peptide as defined herein above may be a functional variant of said defined amino acid sequences.

Variants of peptides according to the present invention are meant to be the functional equivalents of said sequences, i.e. retaining their ability to bind to NCAM.

A functional variant is a variant that retains the same biological activity or capabilities as the peptide from which it is derived; such as those listed herein above: Capable of binding to NCAM, such as the Ig1 module of NCAM, stimulating neurite outgrowth, promoting or stimulating or increasing the survival of neurons, enhancing long-term potentiation, regulating neuroplasticity, and/or stimulating learning and memory.

The peptide variants according to the present invention may comprise one or more amino acid substitutions introduced independently of one another. In one embodiment, peptide variants according to the present invention comprises 1 amino acid substitution, for example 2 amino acid substitutions, such as 3 amino acid substitutions, for example 4 amino acid substitutions, such as 5 amino acid substitutions, for example 6 amino acid substitutions, such as 7 amino acid substitutions, for example 8 amino acid substitutions, such as 9 amino acid substitutions, for example 10 amino acid substitutions.

In one embodiment, said one or more amino acid substitution is a conservative amino acid substitution (or synonymous substitution), that is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

In one embodiment, a serine residue (Ser) of SEQ ID NO: 1, or a fragment thereof, is substituted with an amino acid selected from the group consisting of Gln, Asn and Thr (all amino acids with polar uncharged side chains); and independently thereof, a glycine residue (Gly) is substituted with an amino acid selected from the group consisting of Ala, Val, Leu, and Ile; and independently thereof, an arginine residue (Arg) is substituted with an amino acid selected from the group consisting of Lys and His (all have positively charged side chains); and independently thereof, a lysine residue (Lys) is substituted with an amino acid selected from the group consisting of Arg and His; and independently thereof, a methionine residue (Met) is substituted with an amino acid selected from the group consisting of Leu, Pro, Ile, Val, Phe, Tyr and Trp (all have hydrophobic side chains); and independently thereof, a glutamine residue (Gln) is substituted with an amino acid selected from the group consisting of Asp, Glu, and Asn; and independently thereof, an alanine residue (Ala) is substituted with an amino acid selected from the group consisting of Gly, Val, Leu, and Ile.

The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90, or by simple comparison of the specific amino acids present at corresponding positions in two peptide sequences to be compared.

Homology may be used as a synonym to identity/sequence identity.

A variant of a peptide of the invention may also be an amino acid sequence which has about 10% positive amino acid matches with any of SEQ ID NOs: 1 to 19, such as about 20% positive amino acid matches, for example about 30% positive amino acid matches, such as about 40% positive amino acid matches, for example about 50% positive amino acid matches, such as about 60% positive amino acid matches, for example about 70% positive amino acid matches, such as about 80% positive amino acid matches, for example about 90% positive amino acid matches, wherein a positive amino acid match is defined as the presence at the same position in two compared sequences of amino acid residues which has similar physical and/or chemical properties. Particular positive amino acid matches of the present invention are K to R, E to D, L to M, Q to E, I to V, I to L, A to S, Y to W, K to Q, S to T, N to S and Q to R.

In another embodiment, a variant according to the present invention include sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, and/or wherein a dibasic monocarboxylic amino acid is substituted for a dibasic monocarboxylic amino acid.

Conservative substitutions may be introduced in any one or more positions of a peptide according to the invention or a fragment thereof, as long as the variant remains functional. It may however also be desirable to introduce non-conservative substitutions in one or more positions (non-synonymous substitutions).

A non-conservative substitution leading to the formation of a variant of the peptide according to the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like.

The peptides according to the present invention comprise proteinogenic or natural amino acids, ie. the 22 amino acids naturally incorporated into polypeptides. Of these, 20 are encoded by the universal genetic code (cf. table 1 above) and the remaining 2; selenocysteine (Sec, U) and pyrrolysine (Pyl, O), are incorporated into proteins by unique synthetic mechanisms.

A peptide according to the invention in one embodiment may also comprise one or more non-naturally occurring amino acid residues (unnatural, non-proteinogenic or non-standard amino acids). Non-naturally occurring amino acids include e.g., without limitation, beta-2-naphthyl-alanine, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamnine, homoglutamine, pipecolic acid, thiazolidine carboxylic acid, dehydroproline, 3- and 4-methylproline, 3,3-dimethylproline, tert-leucine, norleucine, norvaline, 2-azaphenylalanine, 3-azaphenylalanine, 4-azaphenylalanine, and 4-fluorophenylalanine.

Any amino acids according to the present invention may be in the L- or D-configuration. If nothing is specified, reference to the L-isomeric form is preferably meant.

The standard and/or non-standard amino acids may be linked by peptide bonds (to form a linear peptide chain), or by non-peptide bonds (e.g. via the variable side-chains of the amino acids). Preferably, the amino acids of the present invention are linked by peptide bonds.

In one embodiment the peptide according to the present invention comprises Tyr at position 21 (Tyr21), ie. Tyr of position 21 is not substituted.

The term peptide also embraces post-translational modifications introduced by chemical or enzyme-catalyzed reactions, as are known in the art. These include acetylation, phosphorylation, methylation, glucosylation, glycation, amidation, hydroxylation, deimination, deamidation, carbamylation and sulfation of one or more amino acid residues, and also proteolytic modification by known proteinases including lysosomal kathepsins, and also calpains, secretases and matrix-metalloproteinases.

Also, functional equivalents of the peptides may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins (non-proteinogenic).

Sterically similar compounds may be formulated to mimic the key portions of the peptide structure. This may be achieved by techniques of modelling and chemical designing known to those of skill in the art. For example, esterification and other alkylations may be employed to modify the amino terminus of e.g a di-arginine peptide backbone, to mimic a tetra peptide structure. It will be understood that all such sterically similar constructs fall within the scope of the present invention. Peptides with N-terminal and C-terminal alkylations and esterifications are also encompassed within the present invention.

Where nothing is specified it is to be understood that the C-terminal amino acid of a peptide according to the present invention exists as the free carboxylic acid, this may also be specified as "—OH". However, the C-terminal amino acid of a peptide for use according to the invention may in another embodiment be the amidated derivative, which is indicated as "—$NH_2$" (or "$CONH_2$").

Where nothing else is stated the N-terminal amino acid of the peptide comprises a free amino-group, this may also be specified as "H—" (or "$NH_2$"). However, the N-terminal amino acid of a peptide according to the invention may in another embodiment be the acetylated derivative, which is indicated as "Acetyl" or "$COCH_3$".

In one embodiment the C-terminal amino acid of the peptide according to the present invention exists as the free carboxylic acid ("—OH"). In another embodiment the C-terminal amino acid of the peptide according to the present invention is an amidated derivative ("—$NH_2$"). In one embodiment the N-terminal amino acid of the peptide according to the present invention comprises a free amino-group ("H—"). In another embodiment the N-terminal amino acid of the peptide according to the present invention is the acetylated derivative ("-Acetyl" or "$COCH_3$").

A contiguous or consecutive peptide sequence is a sequence of consecutive amino acids being linked linearly by peptide bonds. Contiguous and consecutive amino acid sequence is used interchangeably herein.

In one embodiment, the peptide according to the present invention comprises a contiguous amino acid sequence of 32 amino acids, such as 31 amino acids, for example 30 amino acids, for example 29 amino acids, such as 28 amino acids, for example 27 amino acids, such as 26 amino acids, for example 25 amino acids, such as 24 amino acids, for example 23 amino acids, such as 22 amino acids, for example 21 amino acids, such as 20 amino acids, for example 19 amino acids, such as 18 amino acids, for example 17 amino acids, such as 16 amino acids, for example 15 amino acids derived from NPY (SEQ ID NO:22) which comprises at least NPY21-35 (SEQ ID NO:19) or a variant thereof.

In one embodiment, the peptide according to the present invention comprises a contiguous amino acid sequence of at most 32 amino acids, such as at most 31 amino acids, for example at most 30 amino acids, for example at most 29 amino acids, such as at most 28 amino acids derived from NPY (SEQ ID NO:22) which comprises at least NPY21-35 (SEQ ID NO:19) or a variant thereof.

In another embodiment, the peptide comprises a contiguous amino acid sequence of at least 15 amino acids, for example at least 16 amino acids, for example at least 17 amino acids, such as at least 18 amino acids, for example at least 19 amino acids, such as at least 20 amino acids derived from NPY (SEQ ID NO:22) which comprises at least NPY21-35 (SEQ ID NO:19) or a variant thereof.

A peptide of the present invention in one embodiment consists of from 15-32 contiguous amino acids. In one embodiment, the peptide of the invention consists of from 15-16, for example 16-17, such as 17-18, for example 18-19, such as 19-20, for example 20-21, such as 21-22, for example 22-23, such as 23-24, for example 24-25, such as 25-26, for example 26-27, such as 27-28, for example 28-29, such as 29-30, for example 30-31, such as 31-32 contiguous amino acids derived from NPY (SEQ ID NO:22) which comprises at least NPY21-35 (SEQ ID NO:19) or a variant thereof.

The peptide of the present invention in another embodiment comprises a contiguous amino acid sequence having a total length of more than or equal to 15, 16, 17, 18, 19, 20, 21, 22, 23, 24, 25, 26, 27, 28, 29, 30, 31 or 32 contiguous amino acid residues derived from NPY (SEQ ID NO:22) and comprising at least NPY21-35 (SEQ ID NO:19) or a variant thereof.

Compound of the Present Invention

It is an aspect of the present invention to provide a compound comprising or consisting of a peptide according to the present invention. In one embodiment, said peptide is formulated as a monomer (i.e. comprising 1 copy of the peptide), whereas in another embodiment, said peptide is formulated as a multimer.

It is an aspect of the present invention to provide a compound according to the present invention for use as a medicament and/or for use in a method of treating a disease or disorder of the central nervous system and/or the eye.

Multimeric Compound

In one embodiment the peptide according to the present invention is formulated as a multimer. A multimer is a protein comprising or consisting of multiple monomers. A multimer is an aggregate of multiple molecules (aka monomers, as mono=one) that is usually held together with non-covalent bonds. This definition distinguishes a multimer from a polymer, which is a series of monomers that are held together with covalent bonds.

A peptide sequence of the present invention may be connected to another (identical or non-identical) peptide sequence of the present invention by a chemical bond or through a linker group. In some embodiments a peptide of the invention may be formulated as an oligomer or multimer of monomers, wherein each monomer is as a peptide sequence as defined according to the present invention.

Thus, according to the invention a multimeric compound may be a polymer comprising two or more peptide sequences of the invention, said peptide sequences being identical or non-identical, wherein at least one of the two or more peptide sequences is a peptide according to the present invention. Preferably, both peptide sequences are a peptide according to the present invention.

In one embodiment the multimeric compound is a dimer, comprising two peptides according to the present invention, said two peptides being identical or non-identical with respect to each other.

In another embodiment the multimeric compound is a trimer, comprising three peptides according to the present invention, said peptides being identical or non-identical with respect to each other.

In another embodiment the multimeric compound is a tetramer, comprising four peptides according to the present invention, said peptides being identical or non-identical with respect to each other.

In one embodiment the multimeric compound is a dendrimer, such as a tetrameric or octameric dendrimer. Dendrimers are repeatedly branched, roughly spherical large molecules, typically symmetric around the core, and often adopts a spherical three-dimensional morphology.

Dendrimers according to the present invention may comprise 4 peptides, 8 peptides, 16 peptides, or 32 peptides. In one particular embodiment said dendrimer comprises four peptides (i.e. a tetrameric dendrimer) or eight peptides (octameric dendrimer).

In some particular embodiments, the multimeric compound may comprise two identical amino acid sequences of the present invention (dimer) or the compound may comprise four identical copies of an amino acid sequence of the present invention (tetrameric dendrimer).

The multimers according to the invention may be made by linking two or more peptide monomers via a peptide bond or a linker group. They may be linked to a lysine backbone, such as a lysine residue (each peptide chain is linked to a single lysine residue), or coupled to a polymer carrier, for example a protein carrier. Said linker group in one embodiment comprises a plurality of lysine residues, such as a core moiety having a plurality of lysine residues, such as seen in a lysine-based dendromeric structure containing three, seven, fifteen and more lysine residues However, any other linking of peptide monomers known to the skilled person may be envisioned.

The linking may in one embodiment occur at the N-terminal or C-terminal end of the peptide monomers.

Nucleic Acid Constructs Encoding NPY Peptide

There are a variety of diseases of the retina arising from genetic and non-genetic causes, or a combination of both. The retina is a prime location for gene therapy because of its accessibility, immune privileged status, and susceptible cell types. Several strategies have been attempted to rescue retinal disease, including gene replacement, gene knockdown with both ribozymes and siRNA and therapeutic gene supplementation.

In one embodiment of the present invention there is provided a nucleic acid construct encoding for and being capable of expressing a peptide according to the present invention. Preferably said nucleic acid construct will be able to continuously express a peptide according to the present invention for a prolonged period of time, such as at least 1 month, for example at least 2 months, such as at least 3 months, for example at least 4 months, such as at least 5 months, for example at least 6 months, such as at least 7 months, for example at least 8 months, such as at least 9 months, for example at least 12 months.

It is an aspect of the present invention to provide a nucleic acid construct encoding a peptide consisting of a peptide sequence of from 15 to 33 contiguous amino acid residues derived from neuropeptide Y (NPY) (SEQ ID NO:22), wherein said peptide comprises at least, or consists of, the sequence YSALRHYINLITRQR (NPY21-35; SEQ ID NO:19), or a functional variant having at least 60% sequence identity to SEQ ID NO:19, wherein said peptide does not comprise the Tyr amino acid of position 36 of SEQ ID NO:22.

It is also an aspect of the present invention to provide a nucleic acid construct encoding a peptide consisting of a peptide sequence of 15 to 32 contiguous amino acid residues derived from neuropeptide Y (NPY) (SEQ ID NO:22), wherein said peptide comprises or consist of the sequence YSALRHYINLITRQR (NPY21-35; SEQ ID NO:19), or a variant having at least 60% sequence identity to SEQ ID NO:19, wherein said peptide does not comprise the Tyr amino acid of position 36 of NPY (SEQ ID NO:22).

It is also an aspect of the present invention to provide a nucleic acid construct encoding a peptide consisting of 15 to 33 contiguous amino acid residues derived from neuropeptide Y (NPY) (SEQ ID NO:22), wherein said peptide comprises at least, or consists of, the sequence YSALRHYINLITRQR (NPY21-35; SEQ ID NO:19), or a functional variant thereof, wherein said peptide does not comprise the Tyr amino acid of position 36 of SEQ ID NO:22, for use in a method of treating a disease or disorder of the central nervous system and/or the eye.

In one embodiment the encoded peptide of the a nucleic acid construct is a variant having at least 60% sequence identity to any one of SEQ ID NOs: 1 to 19, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to any one of SEQ ID NOs: 1 to 19.

In one embodiment the encoded peptide of the a nucleic acid construct is a variant having from 60 to 65% sequence identity, for example from 65 to 70% sequence identity, such as from 70 to 75% sequence identity, for example from 75 to 80% sequence identity, such as from 80 to 85% sequence identity, for example from 85 to 90% sequence identity, such as from 90 to 95% sequence identity, for example from 95 to 99% sequence identity to any one of SEQ ID NOs: 1 to 19.

In one embodiment, said encoded peptide of the nucleic acid construct is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or a functional variant having at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

In one embodiment, said encoded peptide of the nucleic acid construct does not comprise or consist of SEQ ID NO:1 (NPY3-35), unless when used in a method of treating a disease or disorder of the central nervous system and/or the eye.

By nucleic acid construct is understood a genetically engineered nucleic acid. The nucleic acid construct may be a non-replicating and linear nucleic acid, a circular expression vector or an autonomously replicating plasmid. A nucleic acid construct may comprise several elements such as, but not limited to genes or fragments of same, promoters, enhancers, terminators, poly-A tails, linkers, polylinkers, operative linkers, multiple cloning sites (MCS), markers, STOP codons, internal ribosomal entry sites (IRES) and host homologous sequences for integration or other defined elements. It is to be understood that the nucleic acid construct according to the present invention may comprise all or a subset of any combination of the above-mentioned elements.

Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). Further, nucleic acid constructs according to the present invention may be synthesized without template, and may be obtained from various commercial suppliers (e.g. Genscript Corporation).

In one embodiment, the nucleic acid construct are naked DNA constructs comprising sequences encoding the peptide of the invention.

It is also an aspect of the present invention to provide the nucleic acid construct as described herein above comprised within a delivery vehicle. A delivery vehicle is an entity whereby a nucleotide sequence or polypeptide or both can be transported from at least one media to another. Delivery vehicles are generally used for expression of the sequences encoded within the nucleic acid construct and/or for the intracellular delivery of the construct or the polypeptide encoded therein.

In one embodiment, there is provided a delivery vehicle comprising the nucleic acid construct according to the present invention. A delivery vehicle may be selected from the group consisting of: RNA based vehicles, DNA based vehicles/vectors, lipid based vehicles (such as a liposome), polymer based vehicles (such as a cationic polymer DNA carrier), colloidal gold particles (coating) and virally derived DNA or RNA vehicles or vectors.

Methods of non-viral delivery include physical (carrier-free delivery) and chemical approaches (synthetic vector-based delivery).

Physical approaches, including needle injection, gene gun, jet injection, electroporation, ultrasound, and hydrodynamic delivery, employ a physical force that permeates the cell membrane and facilitates intracellular gene transfer. Said physical force may be electrical or mechanical.

Examples of chemical delivery vehicles include, but are not limited to: biodegradable polymer microspheres, lipid based formulations such as liposome carriers, cationically charged molecules such as liposomes, calcium salts or dendrimers, lipopolysaccharides, polypeptides and polysaccharides.

Another embodiment of the present invention comprises a vector which herein is denoted a viral vector (i.e. not a virus) as a delivery vehicle. Viral vectors according to the present invention are made from a modified viral genome, i.e. the actual DNA or RNA forming the viral genome, and introduced in naked form. Thus, any coat structures surrounding the viral genome made from viral or non-viral proteins are not part of the viral vector according to the present invention.

The virus from which the viral vector is derived may be selected from the non-exhaustive group of: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

In one embodiment, said viral vectors may be selected from the group consisting of adenoviruses, lentiviruses, adeno-associated viruses (AAV) and recombinant adeno-associated viruses (rAAV). In one preferred embodiment, said viral vector is a therapeutic rAAV vector such as a therapeutic rAAV vector.

An adenovirus is a group of double-stranded DNA containing viruses. Adenoviruses can be genetically modified making them replication incompetent or conditionally replication incompetent. In this form, as adenoviral constructs or adenovectors, they can be used as gene delivery vehicles for vaccination or gene therapy.

Gene therapy vectors using AAV can infect both dividing and quiescent cells and persist in an extrachromosomal state without integrating into the genome of the host cell. These features make AAV a very attractive candidate for creating viral vectors for gene therapy. To date, AAV vectors have been used in over 80 clinical trials worldwide.

At least 11 serotypes of AAV exists, and all of these are encompassed by the present invention.

Viral expression vectors that have been utilized to target retinal cells include adenoviruses, lentiviruses, and recombinant adeno-associated viruses (rAAV).

Recombinant adeno-associated viral vectors (rAAV) are moving to the forefront of gene therapy experiments. Given the non-pathogenic nature, low immunogenicity, ease of delivery, persistence, and targeting possibilities of rAAV, it is poised to become a major player in retinal gene therapy.

Vectors derived from adeno-associated virus (AAV) are currently the most promising vehicles for therapeutic gene delivery to the retina. Recently, subretinal administration of AAV2 has been demonstrated to be safe and effective in patients with a rare form of inherited childhood blindness, suggesting that AAV-mediated retinal gene therapy may be successfully extended to other blinding conditions. This is further supported by the great versatility of AAV as a vector platform as there are a large number of AAV variants and many of these have unique transduction characteristics useful for targeting different cell types in the retina including glia, epithelium and many types of neurons. Naturally occurring, rationally designed or in vitro evolved AAV vectors are currently being utilized to transduce several different cell types in the retina and to treat a variety of animal models of retinal disease. See e.g. Vandenberghe & Auricchio (Gene Ther 2012 February; 19(2):162-8 'Novel adeno-associated viral vectors for retinal gene therapy').

Recombinant Cell

An aspect of the present invention relates to a cell comprising the nucleic acid construct according to the present invention. Such a recombinant cell can be used a tool for in vitro research, as a delivery vehicle for the nucleic acid construct or as part of a gene-therapy regime. The nucleic acid construct according to the invention can be introduced into cells by techniques well known in the art and which include microinjection of DNA into the nucleus of a cell, transfection, electroporation, lipofection/liposome fusion and particle bombardment. Suitable cells include autologous and non-autologous cells, and may include xenogenic cells.

Method of Treatment

It is also an aspect of the present invention to provide a peptide or a nucleic acid construct encoding a peptide according to the present invention for use as a medicament.

It is a further aspect of the present invention to provide a peptide, or a nucleic acid construct encoding a peptide, said peptide consisting of 15 to 33 contiguous amino acid residues derived from neuropeptide Y (NPY) (SEQ ID NO:22), wherein said peptide comprises at least, or consist of, the sequence YSALRHYINLITRQR (NPY21-35; SEQ ID NO:19), or a functional variant thereof, wherein said peptide does not comprise the Tyr amino acid of position 36 of SEQ ID NO:22, for use in a method of treating a disease or disorder of the central nervous system and/or the eye.

Also provided is a method for treating a disease or disorder of the central nervous system and/or the eye, said method comprising administering to an individual in need thereof an effective amount of a peptide, or a nucleic acid construct encoding a peptide, said peptide consisting of 15 to 33 contiguous amino acid residues derived from neuropeptide Y (NPY) (SEQ ID NO:22), wherein said peptide comprises at least, or consist of, the sequence YSALRHYINLITRQR (NPY21-35; SEQ ID NO:19), or a functional variant thereof, wherein said peptide does not comprise the Tyr amino acid of position 36 of SEQ ID NO:22.

An individual in need as referred to herein, is an individual that may benefit from the administration of a peptide or pharmaceutical composition according to the present invention. Such an individual may suffer from a disease or disorder of the central nervous system and/or the eye or be in risk of suffering therefrom. The individual may be any human being, male or female, infant, middle-aged or old. The disorder to be treated or prevented in the individual may relate to the age of the individual, the general health of the individual, the medications used for treating the individual and whether or not the individual has a prior history of suffering from diseases or disorders that may have or have induced a disease or disorder of the central nervous system and/or the eye in the individual.

By 'treating a disease or disorder' is meant one or more of treatment, prevention and alleviation.

Also provided is the use of a peptide, or a nucleic acid construct encoding a peptide, said peptide consisting of 15 to 33 contiguous amino acid residues derived from neuropeptide Y (NPY) (SEQ ID NO:22), wherein said peptide comprises at least, or consist of, the sequence YSALRHYINLITRQR (NPY21-35; SEQ ID NO:19), or a functional variant thereof, wherein said peptide does not comprise the Tyr amino acid of position 36 of SEQ ID NO:22, for the manufacture of a medicament for use in a method of treating a disease or disorder of the central nervous system and/or the eye.

Method of Treatment—Diseases and Disorders of the Eye

In one embodiment there is provided a peptide or a nucleic acid construct according to the present invention for use in a method of treating a disease or disorder of the eye.

In one embodiment said disease or disorder of the eye is a disease or disorder involving neurons, in one embodiment retinal or optic nerve neurons.

In one embodiment said disease or disorder of the eye is a retinal or optic nerve disease or disorder.

In one embodiment said disease or disorder of the eye is a retinal disease or disorder. In another embodiment said disease or disorder of the eye is an optic nerve disease or disorder.

A retinal disease or disorder implies that the retina of the eye is involved in the disease or disorder. The retina comprises neurons, and as such retinal disorders as such are disorders in which neuritogenesis and/or neuroprotection are desirable.

The vertebrate retina is a light-sensitive layer of tissue, lining the inner surface of the eye. The optics of the eye creates an image of the visual world on the retina, which serves much the same function as the film in a camera. Light striking the retina initiates a cascade of chemical and electrical events that ultimately trigger nerve impulses. These are sent to various visual centers of the brain through the fibers of the optic nerve. In vertebrate embryonic development, the retina and the optic nerve originate as outgrowths of the developing brain, so the retina may be considered part of the central nervous system (CNS).

The retina is a layered structure with several layers of neurons interconnected by synapses. The only neurons that are directly sensitive to light are the photoreceptor cells. These are mainly of two types: the rods and cones. The entire retina contains about 7 million cones and 75 to 150 million rods. Rods function mainly in dim light and provide black-and-white vision, while cones support daytime vision and the perception of colour. A third, much rarer type of photoreceptor, the photosensitive ganglion cell, is important for reflexive responses to bright daylight. Neural signals from the rods and cones undergo processing by other neurons of the retina. The output takes the form of action potentials in retinal ganglion cells whose axons form the optic nerve.

The macula or macula lutea is an oval-shaped highly pigmented yellow spot near the center of the retina of the human eye. It has a diameter of around 1.5 mm and is often histologically defined as having two or more layers of ganglion cells. Near its center is the fovea, a small pit that contains the largest concentration of cone cells in the eye and is responsible for central, high resolution vision. The macula also contains the parafovea and perifovea.

There are many inherited and acquired diseases and disorders that affect the retina.

In one embodiment there is provided a peptide according to the present invention for use in a method of treating a retinal disease or disorder, wherein said retinal disease or disorder is selected from the group consisting of retinitis pigmentosa (group of genetic diseases that affect the retina and cause the loss of night vision and peripheral vision);

macular degeneration (diseases characterized by loss of central vision because of death or impairment of the cells in the macula);

cone-rod dystrophy (CORD) (diseases where vision loss is caused by deterioration of the cones and/or rods in the retina);

retinal detachment or separation (in which the retina detaches from the back of the eyeball; the term retinal detachment is used to describe a separation of the neurosensory retina from the retinal pigment epithelium);

hypertensive retinopathy and diabetic retinopathy (hypertension and diabetes mellitus can cause damage to the tiny blood vessels that supply the retina).

An optic nerve disease or disorder implies that the optic nerve of the eye is involved in the disease or disorder. The optic nerve is the second of twelve paired cranial nerves but is commonly considered to be part of the central nervous system, as it is derived from an outpouching of the diencephalon during embryonic development, covered with myelin and ensheathed in all three meningeal layers. Also it does not regenerate after injury. The optic nerve, also known as cranial nerve 2, transmits visual information from the retina to the brain. The fibers from the retina run along the optic nerve to nine primary visual nuclei in the brain, from which a major relay inputs into the primary visual cortex. The optic nerve is composed of retinal ganglion cell axons and support cells.

Damage or injury to the optic nerve typically causes permanent and potentially severe loss of vision, as well as an abnormal pupillary reflex, which is diagnostically important. The type of visual field loss will depend on which portions of the optic nerve were damaged.

Injury to the optic nerve can be the result of congenital or inheritable problems like Leber's Hereditary Optic Neuropathy, glaucoma, trauma, toxicity, inflammation, ischemia, infection (very rarely), or compression from tumors or aneurysms. By far, the three most common injuries to the optic nerve are from glaucoma, optic neuritis (especially in those younger than 50 years of age), and anterior ischemic optic neuropathy (usually in those older than 50).

In one embodiment, said optic nerve disease or disorder is selected from the group consisting of injury to the optic nerve, including traumatic and congenital injuries to the optic nerve, including Leber's Hereditary Optic Neuropathy, glaucoma, trauma, toxicity, inflammation, ischemia, infection (very rarely), compression from tumors or aneurysms, optic neuritis and anterior ischemic optic neuropathy.

Retinitis Pigmentosa

In one embodiment there is provided a peptide or a nucleic acid construct according to the present invention for use in the treatment of retinitis pigmentosa.

Retinitis pigmentosa (commonly referred to as "RP") is a disease characterized by progressive loss of the light sensing photoreceptor cells that line the back of the eye.

Usually the rod photoreceptors (responsible for night vision) are affected first, which is why loss of night vision (nyctalopia) is usually the first symptom. Loss of daytime vision (mediated by the cone photoreceptors) is usually preserved until the late stages of the disease. It may eventually lead to blindness.

Mottling of the retinal pigment epithelium with black bone-spicule pigmentation is typically indicative of retinitis pigmentosa. Other ocular features include waxy pallor of the optic nerve head, attenuation (thinning) of the retinal vessels, cellophane maculopathy, cystic macular edema, and posterior subcapsular cataract.

RP is one of the most common forms of inherited retinal degeneration. There are multiple genes that, when mutated, can cause the Retinitis pigmentosa phenotype, including the gene coding for rhodopsin and opsin. When a specific gene is implicated the RP may be diagnosed accordingly based on the specific mutation, and is denoted by a suffix (e.g. RP4 is the RHO mutation).

Currently there is no cure for retinitis pigmentosa, but treatments are now available in some countries. The progression of the disease can be reduced by the daily intake of vitamin A. A very recent approach for therapy is the *Argus* II retinal implant (anelaborate epiretinal prosthesis surgically implanted in and on the eye that includes an antenna, an electronics case, and an electrode array).

Retinal Detachment

In one embodiment there is provided a peptide or a nucleic acid construct according to the present invention for use in the treatment of retinal detachment.

Retinal detachment is a disorder of the eye in which the retina peels away from its underlying layer of support tissue. Initial detachment may be localized, but without rapid treatment the entire retina may detach, leading to vision loss and blindness.

The optical system of the eye focuses light on the retina, and the retina translates that focused image into neural impulses and sends them to the brain via the optic nerve. Occasionally, posterior vitreous detachment, injury or trauma to the eye or head may cause a small tear in the retina. The tear allows vitreous fluid to seep through it under the retina, and peel it away. Photoreceptors in patients with retinal detachment display abundant structural plasticity in the form of axonal retraction, neurite extension, and formation of presynaptic varicosities.

A retinal detachment is commonly preceded by posterior vitreous detachment. A posterior vitreous detachment (PVD) is a condition of the eye in which the vitreous membrane separates from the retina. It refers to the separation of the posterior hyaloid membrane from the retina anywhere posterior to the vitreous base (a 3-4 mm wide attachment to the ora serrata). Broadly speaking, the condition is common for older adults and over 75% of those over the age of 65 develop it. Although less common among people in their 40s or 50s, the condition is not rare for those individuals.

Retinal detachment may be caused by e.g. AIDS, cataract surgery, diabetic retinopathy, eclampsia, homocysteinuria, malignant hypertension, retinoblastoma, metastatic eye cancer, stickler syndrome and Von Hippel-Lindau disease.

In one embodiment there is provided a peptide or a nucleic acid construct according to the present invention for use in the treatment of posterior vitreous detachment.

Retinal detachment may be sub-classified into the following three types, which are all encompassed by the present invention:

1) Rhegmatogenous retinal detachment—occurs due to a break in the retina (called a retinal tear) that allows fluid to pass from the vitreous space into the subretinal space. Retinal breaks are divided into three types—holes, tears and dialyses. Holes form due to retinal atrophy especially within an area of lattice degeneration. Tears are due to vitreoretinal traction. Dialyses which are very peripheral and circumferential may be either tractional or atrophic, the atrophic form most often occurring as idiopathic dialysis of the young. A minority of rhegmatogenous retinal detachments result from trauma, including blunt blows to the orbit, penetrating trauma, and concussions to the head. Gradual onset appears to be the norm, with over 50% presenting more than one month after the inciting injury.

2) Exudative, serous, or secondary retinal detachment— occurs due to inflammation, injury or vascular abnormalities that results in fluid accumulating underneath the retina without the presence of a hole, tear, or break. In evaluation of retinal detachment it is critical to exclude exudative detachment as surgery will make the situation worse, not better. Although rare, exudative retinal detachment can be caused by the growth of a tumor on the layers of tissue beneath the retina, namely the choroid. This cancer is called a choroidal melanoma, and 3) Tractional retinal detachment—occurs when fibrous or fibrovascular tissue, caused by an injury, inflammation or neovascularization, pulls the sensory retina from the retinal pigment epithelium.

Treatment of retinal detachment by use of the peptides according to the present invention is an alternative or may be an add-on to the surgical treatment employed today, including Cryopexy and laser photocoagulation, Scleral buckle surgery, Pneumatic retinopexy and Vitrectomy.

Retinopathies

In one embodiment there is provided a peptide or a nucleic acid construct according to the present invention for use in the treatment of a retinopathy.

In one embodiment there is provided a peptide or a nucleic acid construct according to the present invention for use in the treatment of a retinopathy selected from the group consisting of diabetic retinopathy, hypertensive retinopathy, radiation retinopathy, proliferative vitreoretinopathy (PVR), retinopathy due to autoimmune disease, retinopathy due to anemia, and retinopathy due to retinal vein or artery occlusion.

In one embodiment there is provided a peptide or a nucleic acid construct according to the present invention for use in the treatment of diabetic retinopathy.

Diabetic retinopathy is retinopathy (damage to the retina) caused by complications of diabetes, which can eventually lead to blindness. It is an ocular manifestation of diabetes, a systemic disease, which affects up to 80 percent of all patients who have had diabetes for 10 years or more. The longer a person has diabetes, the higher his or her chances of developing diabetic retinopathy.

Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. Small blood vessels such as those in the eye are especially vulnerable to poor blood glucose control. During the initial stage, called non-proliferative diabetic retinopathy (NPDR), most people do not notice any change in their vision. Early changes that are reversible and do not threaten central vision are sometimes termed simplex retinopathy or background retinopathy As the disease progresses, severe non-proliferative diabetic retinopathy enters an advanced, or proliferative (PDR), stage when blood vessels proliferate. The lack of oxygen in the retina causes fragile, new, blood vessels to grow along the retina and in the clear, gel-like vitreous humour that fills the inside of the eye. Without timely treatment, these new blood vessels can bleed, cloud vision, and destroy the retina. Fibrovascular proliferation can also cause tractional retinal detachment. The new blood vessels can also grow into the angle of the anterior chamber of the eye and cause neovascular glaucoma.

There is no cure for diabetic retinopathy, however further vision loss may be slowed or stopped by laser surgery/laser photocoagulation, injection of corticosteroids or Anti-VEGF (VEGF antibody) into the eye, or vitrectomy (surgery to remove some or all of the vitreous humor from the eye).

Hypertensive retinopathy is damage and adaptive changes to the retina and retinal circulation due to high blood pressure (i.e. hypertension).

Radiation retinopathy is damage to retina due to exposure to ionizing radiation. Said radiation may be administered for treatment of ocular and other cancers, such as cancers of the head and neck area. Radiation retinopathy has a delayed onset, typically after months or years of radiation, and is slowly progressive. An exposure to doses of 30-35 Gy or more is usually required to induce clinical symptoms, however, retinopathy may develop after as little as 15 Gy of external-beam radiation.

Proliferative vitreoretinopathy (PVR) is a disease that develops as a complication, secondary to rhegmatogenous retinal detachment (occurs due to a break in the retina) following retinal disease, injury or surgery. PVR occurs in about 8-10% of patients undergoing primary retinal detachment surgery and prevents the successful surgical repair of rhegmatogenous retinal detachment. PVR is nowadays be treated with surgery to reattach the detached retina but the visual outcome of the surgery is very poor.

Age-Related Macular Degeneration (AMD)

In one embodiment there is provided a peptide or a nucleic acid construct according to the present invention for use in the treatment of age-related macular degeneration.

In one embodiment there is provided a peptide or a nucleic acid construct according to the present invention for use in the treatment of any stage of age-related macular degeneration (AMD).

Age-related macular degeneration (AMD) is a medical condition which usually affects older adults and results in a loss of vision in the center of the visual field (the macula) because of damage to the retina. It is a major cause of blindness and visual impairment in older adults (>50 years).

AMD occurs in a "dry" and a "wet" form. The dry (nonexudative) form results from atrophy of the retinal pigment epithelial layer below the retina, which causes vision loss through loss of photoreceptors (rods and cones) in the central part of the eye. Cellular debris called drusen accumulates between the retina and the choroid, and the retina can become detached. The wet (exudative) form, which is more severe, causes vision loss due to abnormal blood vessel growth (choroidal neovascularization) where blood vessels grow up from the choroid behind the retina, whereby the retina can become detached. Bleeding, leaking, and scarring from these blood vessels eventually cause irreversible damage to the photoreceptors and rapid vision loss if left untreated.

Myopic Degeneration

In one embodiment there is provided a peptide or a nucleic acid construct according to the present invention for use in the treatment of myopic degeneration (also known as degenerative myopia or myopic macular degeneration).

Myopia, also commonly known as near-sightedness, occurs because the eye is longer than average, causing a blurry image on the retina. In healthy myopic people, vision can be corrected using eyeglasses, contact lenses or laser vision correction. Unlike age-related macular degeneration, myopic macular degeneration can occur at ages as young as 30 years old.

Cone Dystrophy

In one embodiment there is provided a peptide or a nucleic acid construct according to the present invention for use in the treatment of cone dystrophy.

A cone dystrophy is an inherited ocular disorder characterized by the loss of cone cells, the photoreceptors responsible for both central and color vision. The pathogenesis of cone dystrophy has yet to be elucidated. It appears that the dystrophy is primary. However, the retinal pigment epithelium (RPE) rapidly becomes involved, leading to a retinal dystrophy primarily involving the macula.

Other Eye Diseases

There are many inherited and acquired diseases or disorders that may affect the retina and/or optic nerve. In one embodiment there is provided a peptide or a nucleic acid construct according to the present invention for use in the treatment of a condition selected from the group consisting of retinal vein occlusion and retinal artery occlusion, such as central retinal vein occlusion (CRVO) and Branch retinal vein occlusion (BRVO) (which may in turn cause e.g. glaucoma and retinopathy); Uveitis/Vasculitis; Ocular hypertension (when consistent over longer periods of time, can result in nerve damage); Optic neuropathy (aka. optic atrophy, which is damage to the optic nerve due to any cause) including Ischemic optic neuropathy, Optic neuritis, Compressive optic neuropathy, Infiltrative optic neuropathy, Traumatic optic neuropathy, Mitochondrial optic neuropathies, Nutritional optic neuropathies, Toxic optic neuropathies and Hereditary optic neuropathies; Leber's congenital amaurosis (LCA), Lipemia retinalis, eye injury, Angioid streaks (aka. Knapp streaks or Knapp striae), and cancers of the retina including retinoblastoma and metastatic eye cancer.

In one embodiment there is provided a peptide or a nucleic acid construct according to the present invention for use in a method of treating a disease or disorder of the eye, wherein said disease or disorder of the eye is an optic nerve disease. In one embodiment, said optic nerve disease is injury to the optic nerve such as injury caused by glaucoma, Optic neuritis, Anterior Ischemic Optic Neuropathy, or Optic nerve hypoplasia.

Optic neuritis is inflammation of the optic nerve. It is associated with a number of diseases, the most notable one being multiple sclerosis. Up to 50% of patients with MS will develop an episode of optic neuritis, and 20-30% of the time optic neuritis is the presenting sign of MS. Some other causes of optic neuritis include infection (e.g. syphilis, Lyme disease, herpes zoster), autoimmune disorders (e.g. lupus), inflammatory bowel disease, drug induced (e.g. chloramphenicol, ethambutol) vasculitis, and diabetes.

Ischemic optic neuropathy (ION) is the loss of structure and function of a portion of the optic nerve due to obstruction of blood flow to the nerve (i.e. ischemia). Anterior Ischemic Optic Neuropathy (AION) is a particular type of infarct that affects patients with an anatomical predisposition and cardiovascular risk factors. It is caused by damage to the optic nerve from insufficient blood supply. AION is generally divided into two types: arteritic AION (or AAION) and non-arteritic AION (NAION or simply AION), both of which are encompassed by the present invention. AAION is due to temporal arteritis (also called giant cell arteritis), an inflammatory disease of medium-sized blood vessels that occurs especially with advancing age. In contrast, NAION results from the coincidence of cardiovascular risk factors in a patient with "crowded" optic discs. Non-arteritic AION is more common than AAION.

Optic nerve hypoplasia is the underdevelopment of the optic nerve causing little to no vision in the affected eye. This condition is the most common congenital optic nerve anomaly. The optic disc appears abnormally small, because not all the optic nerve axons have developed properly. It is often associated with endocrinopathies (hormone deficiencies), developmental delay, and brain malformations.

Leber's congenital amaurosis (LCA) is a rare inherited eye disease, an autosomal recessive disorder thought to be caused by abnormal development of photoreceptor cells.

Uveitis is broadly defined as inflammation of the uvea. The uvea consists of the middle, pigmented, vascular structures of the eye and includes the iris, ciliary body, and choroid.

Glaucoma

In one embodiment there is provided a peptide or a nucleic acid construct according to the present invention for use in the treatment of glaucoma.

Glaucoma is a group of diseases in which the optic nerve is damaged, involving loss of retinal ganglion cells causing optic neuropathy in a pattern of peripheral vision loss, initially sparing central vision. Untreated glaucoma can lead to permanent damage of the optic nerve and resultant visual field loss, which over time can progress to blindness. It is normally associated with increased fluid pressure in the eye (aqueous humour). The nerve damage involves loss of retinal ganglion cells in a characteristic pattern. The many different subtypes of glaucoma can all be considered to be a type of optic neuropathy.

Glaucoma can be roughly divided into two main categories, "open-angle" and "closed-angle" (or "angle closure") glaucoma. The angle refers to the area between the iris and cornea, through which fluid must flow to escape via the trabecular meshwork. Closed-angle glaucoma can appear suddenly and is often painful; visual loss can progress quickly, but the discomfort often leads patients to seek medical attention before permanent damage occurs. Open-angle, chronic glaucoma tends to progress at a slower rate and patients may not notice they have lost vision until the disease has progressed significantly. Open-angle glaucoma accounts for 90% of glaucoma cases in the US. It is painless and does not have acute attacks Worldwide, glaucoma is the second-leading cause of blindness after cataracts. Glaucoma affects one in 200 people aged 50 and younger, and one in 10 over the age of eighty. If the condition is detected early enough, it is possible to arrest the development or slow the progression with medical and surgical means; however no cure or improvement is possible at present.

Of the several causes for glaucoma, ocular hypertension (increased pressure within the eye) is the most important risk factor in most glaucomas, but in some populations, only 50% of people with primary open-angle glaucoma actually have elevated ocular pressure. Positive family history is a risk factor for glaucoma. Intraocular pressure can be lowered with medication, usually eye drops. Both laser and conventional surgeries are performed to treat glaucoma. Surgery is the primary therapy for those with congenital glaucoma (including Canaloplasty, Laser surgery, Trabeculectomy and Glaucoma drainage implants). Generally, these operations are a temporary solution, as there is not yet a cure for glaucoma.

Method of Treatment—Diseases and Disorders of the Central Nervous System

In one embodiment there is provided a peptide or a nucleic acid construct according to the present invention for use in a method of treating a disease or disorder of the central nervous system (CNS).

Neurodegenerative Disorders

In one embodiment there is provided a peptide or a nucleic acid construct according to the present invention for use in the treatment of a neurodegenerative disorder.

Particularly, said neurodegenerative disorder is such that neuritogenesis, neuroprotection and/or neuroplastic changes are desired. Neurodegeneration is the umbrella term for the progressive loss of structure or function of neurons, including death of neurons. Many neurodegenerative diseases including Parkinson's, Alzheimer's, and Huntington's occur as a result of neurodegenerative processes.

Neurodegenerative diseases are a growing cause of disability in the aging community. Alzheimer's disease (AD) is the most common neurodegenerative disorder. The annual incidence of AD worldwide is estimated to be 4.6 million cases, with one new case every 7 s. Neurodegeneration, the slow progression of dysfunction associated with a loss of neurons and axonal connections in the central nervous system (CNS), is the primary pathological characteristic of such neurological disorders as AD, Parkinson's disease (PD) and Huntington's disease (HD). This loss results in gross atrophy of the affected regions, including degeneration in the temporal lobe and parietal lobe, and parts of the frontal cortex and cingulate gyrus.

Many neurodegenerative diseases are caused by genetic mutations, most of which are located in completely unrelated genes. In many of the different diseases, the mutated gene has a common feature: a repeat of the CAG nucleotide triplet (encodes glutamine). A repeat of CAG results in a polyglutamine (polyQ) tract, and diseases showing this are known as polyglutamine diseases (polyQ diseases). These include Huntington's disease, spinocerebellar ataxias, DRPLA (Dentatorubropallidoluysian atrophy) and SBMA (Spinobulbar muscular atrophy or Kennedy disease).

In one embodiment, the there is provided a peptide according to the present invention for use in the treatment of a neurodegenerative disorder selected from the group consisting of Alzheimer's disease, Parkinson's disease, Huntington's disease, Amyotrophic lateral sclerosis (ALS; Lou Gehrig's Disease), Multiple Sclerosis, and the polyglutamine diseases including spinocerebellar ataxias (Spinocerebellar ataxia type 1, Spinocerebellar ataxia type 2, Spinocerebellar ataxia type 3 (aka Machado-Joseph's disease), Spinocerebellar ataxia type 6, Spinocerebellar ataxia type 7 and Spinocerebellar ataxia type 17), DRPLA (Dentatorubropallidoluysian atrophy) and SBMA (Spinobulbar muscular atrophy or Kennedy disease).

Alzheimer's Disease

In one embodiment there is provided a peptide or a nucleic acid construct according to the present invention for use in the treatment of Alzheimer's disease.

Alzheimer's disease (AD) is the most common form of dementia. Most often, it is diagnosed in people over 65 years of age, although the less-prevalent early-onset Alzheimer's can occur much earlier.

Although the course of Alzheimer's disease is unique for every individual, there are many common symptoms. The earliest observable symptoms are often mistakenly thought to be 'age-related' concerns, or manifestations of stress. In the early stages, the most commonly recognised symptom is inability to acquire new memories, such as difficulty in recalling recently observed facts. As the disease advances, symptoms include confusion, irritability and aggression, mood swings, language breakdown, long-term memory loss, and the general withdrawal of the sufferer as their senses decline. Gradually, bodily functions are lost, ultimately leading to death. The mean life expectancy following diagnosis is approximately seven years.

Specific brain regions have been shown to shrink as AD patients progress from mild cognitive impairment to AD. Hallmarks of AD can be found in the brains of AD patients, who have a greater number of amyloid plaques (insoluble deposits of amyloid beta around neurons) and neurofibrillary tangles (aggregates of the microtubule-associated, hyperphosphorylated protein Tau, within the cells) in specific brain regions such as the temporal lobe. The accumulation of neurofibrillary tangles leads to disintegration of the neuron transport system.

Parkinson's Disease

In one embodiment there is provided a peptide or a nucleic acid construct according to the present invention for use in the treatment of Parkinson's disease.

Parkinson's disease (PD) is a degenerative disorder of the central nervous system. It results from the death by unknown causes of the dopamine-containing cells of the substantia nigra, which is a region of the midbrain. Early in the course of the disease symptoms are movement-related, including shaking, rigidity, slowness of movement and difficulty with walking and gait. Later, cognitive and behavioural problems may arise, with dementia commonly occurring in the advanced stages of the disease. PD is more common in the elderly with most cases occurring after the age of 50 years.

The pathology of the disease is characterized by the accumulation of a protein called α-synuclein into inclusions called Lewy bodies in neurons, and from insufficient formation and activity of dopamine produced in certain neurons of parts of the midbrain.

Huntington's Disease

In one embodiment there is provided a peptide or a nucleic acid construct according to the present invention for use in the treatment of Huntington's disease.

Huntington's disease, chorea, or disorder (HD), is a neurodegenerative genetic disorder that affects muscle coordination and leads to cognitive decline and dementia. It typically becomes noticeable in middle age.

The disease is caused by an autosomal dominant mutation on either of an individual's two copies of a gene called Huntingtin. The Huntingtin gene (HTT) codes for the protein Huntingtin (Htt). Part of this gene is a repeated section called a trinucleotide repeat, which varies in length between individuals and may change length between generations. When the length of this repeated section reaches a certain threshold, it produces an altered form of the protein, called mutant Huntingtin protein (mHtt). The differing functions of these proteins are the cause of pathological changes which in turn cause the disease symptoms as the mutated protein results in gradual damage to specific areas of the brain.

Multiple Sclerosis

In one embodiment there is provided a peptide or a nucleic acid construct according to the present invention for use in the treatment of Multiple sclerosis.

Multiple sclerosis (MS, also known as disseminated sclerosis or encephalomyelitis disseminata) is an inflammatory disease in which the fatty myelin sheaths around the axons of the brain and spinal cord are damaged, leading to demyelination and scarring as well as a broad spectrum of signs and symptoms.

MS affects the ability of nerve cells in the brain and spinal cord to communicate with each other. Nerve cells communicate by sending electrical signals called action potentials down long fibers called axons, which are wrapped in an insulating substance called myelin. In MS, the body's own immune system attacks and damages the myelin. When myelin is lost, the axons can no longer effectively conduct signals. The name multiple sclerosis refers to scars (scleroses—better known as plaques or lesions) particularly in the white matter of the brain and spinal cord, which is mainly composed of myelin.

Almost any neurological symptom can appear with the disease, and often progresses to physical and cognitive disability. MS takes several forms, with new symptoms occurring either in discrete attacks (relapsing forms) or slowly accumulating over time (progressive forms). Between attacks, symptoms may go away completely, but permanent neurological problems often occur, especially as the disease advances. There is no known cure for Multiple sclerosis. Treatments attempt to return function after an attack, prevent new attacks, and prevent disability.

Polyglutamine Diseases

In one embodiment there is provided a peptide or a nucleic acid construct according to the present invention for use in the treatment of a polyglutamine (polyQ) disease. In one embodiment, said polyglutamine disease is a spinocerebellar ataxias. In one embodiment, said polyglutamine disease is Spinocerebellar ataxia type 1, Spinocerebellar ataxia type 2, Spinocerebellar ataxia type 3 (aka Machado-Joseph's disease), Spinocerebellar ataxia type 6, Spinocerebellar ataxia type 7 and Spinocerebellar ataxia type 17, DRPLA (Dentatorubropallidoluysian atrophy) and SBMA (Spinobulbar muscular atrophy or Kennedy disease).

In one embodiment there is provided a peptide according to the present invention for use in the treatment of Machado-Joseph's disease. Machado-Joseph's disease (MJD) or Spinocerebellar ataxia type 3 (SCA3) is a rare autosomal, dominantly inherited neurodegenerative disease that causes progressive cerebellar ataxia, which results in a lack of muscle control and coordination of the upper and lower extremities. The symptoms are caused by a genetic mutation that results in an expansion of abnormal CAG trinucleotide repeats in the ATXN3 gene, that results in degeneration of cells in the hindbrain. Some symptoms, such as clumsiness and rigidity, make MJD commonly mistaken for drunkenness and/or Parkinson's disease. Eventually, MJD leads to paralysis; however, intellectual functions usually remain the same.

In one embodiment there is provided a peptide according to the present invention for use in the treatment of SBMA (Spinobulbar muscular atrophy or Kennedy disease). SBMA is a debilitating neurodegenerative disease resulting in muscle cramps and progressive weakness due to degeneration of motor neurons in the brain stem and spinal cord. The condition is associated with mutation of the androgen receptor (AR) gene and is inherited in a X-linked recessive manner. No cure is known.

In one embodiment there is provided a peptide according to the present invention for use in the treatment of DRPLA. Dentatorubral-pallidoluysian atrophy (DRPLA) is an autosomal dominant spinocerebellar degeneration caused by an expansion of a CAG repeat encoding a polyglutamine tract in the atrophin-1 protein. It is also known as Haw River Syndrome and Naito-Oyanagi disease. While several sporadic cases have been reported from Western countries, this disorder seems to be very rare except in Japan.

In one embodiment there is provided a peptide according to the present invention for use in the treatment of Spinocerebellar ataxia.

Other CNS Disorders

In one embodiment, the there is provided a peptide or a nucleic acid construct according to the present invention for use in the treatment of a disease or disorder of the central nervous system, wherein said disorder may be selected from the group consisting of peripheral nerve lesions, stroke and epilepsy.

Epilepsy

In one embodiment there is provided a peptide or a nucleic acid construct according to the present invention for use in the treatment of epilepsy.

Epilepsy is a common and diverse set of chronic neurological disorders characterized by seizures. Epilepsy can involve recurrent and unprovoked seizures, or a single seizure combined with brain alterations which increase the chance of future seizures. In many cases a cause cannot be identified, but epilepsy is often associated with brain trauma (sometimes as a consequence of brain surgery), strokes, brain cancer, and drug and alcohol misuse among others.

Epileptic seizures result from abnormal, excessive or hypersynchronous neuronal activity in the brain. About 50 million people worldwide have epilepsy, and nearly 80% of epilepsy occurs in developing countries. Epilepsy becomes more common as people age. Most epilepsy syndromes are lifelong but some forms are confined to particular stages of childhood. Epilepsy should not be understood as a single disorder, but rather as syndromic disorder with vastly divergent symptoms, all involving episodic abnormal electrical activity in the brain and numerous seizures. Epilepsy is usually controlled, but not cured, with medication. However, over 30% of people with epilepsy do not have seizure control even with the best available medications. Surgery may be considered in difficult cases.

Stroke or Cerebrovascular Accident (CVA)

In one embodiment there is provided a peptide or a nucleic acid construct according to the present invention for use in the treatment of stroke.

A stroke, or cerebrovascular accident (CVA), is the rapid loss of brain function due to disturbance in the blood supply to the brain. This can be due to ischemia caused by blockage (thrombosis, arterial embolism) or a hemorrhage. As a result, the affected area of the brain cannot function, which might result in an inability to move one or more limbs on one side of the body, inability to understand or formulate speech, or an inability to see one side of the visual field. A stroke is a medical emergency and can cause permanent neurological damage and death.

Ischemic stroke occurs because of a loss of blood supply to part of the brain, initiating the ischemic cascade, to which brain tissue is especially vulnerable since it has little respiratory reserve and is completely dependent on aerobic metabolism.

In addition to injurious effects on brain cells, ischemia and infarction can result in loss of structural integrity of brain tissue and blood vessels, partly through the release of matrix metalloproteases. The loss of vascular structural integrity results in a breakdown of the protective blood brain barrier that contributes to cerebral edema, which can cause secondary progression of the brain injury.

Peripheral Nerve Lesions

In one embodiment there is provided a peptide or a nucleic acid construct according to the present invention for use in the treatment of peripheral nerve lesions.

A neuron's response to trauma can often be determined by the severity of the injury, classified by Seddon's classification. In Seddon's Classification, nerve injury is described as either neurapraxia (a temporary interruption of conduction without loss of axonal continuity; a physiologic block of nerve conduction in the affected axons), axonotmesis (loss of the relative continuity of the axon and its covering of myelin, but preservation of the connective tissue framework of the nerve), or neurotmesis (a total severance or disruption of the entire nerve fiber).

Following trauma to the nerve, a short onset of afferent impulses, termed "injury discharge", occurs. While lasting only minutes, this occurrence has been linked to the onset of neuropathic pain. When an axon is severed, the segment of the axon distal to the cut degenerates and is absorbed by Schwann cells. The proximal segment fuses, retracts, and swells, forming a "retraction bulb." The synaptic terminal function is lost, as axoplasmic transport ceases and no neurotransmitters are created. The nucleus of the damaged axon undergoes chromatolysis in preparation for axon regeneration. Schwann cells in the distal stump of the nerve and basal lamina components secreted by Schwann cells guide and help stimulate regeneration. The regenerating axon must make connections with the appropriate receptors in order to make an effective regeneration. If proper connections to the appropriate receptors are not established, aberrant reinnervation may occur. If the regenerating axon is halted by damaged tissue, neurofibrils may create a mass known as a neuroma.

In the event that an injured neuron degenerates or does not regenerate properly, the neuron loses its function or may not function properly. Neuron trauma is not an isolated event and may cause degenerative changes in surrounding neurons. When one or more neurons lose their function or begin to malfunction, abnormal signals sent to the brain may be translated as painful signals.

Method of Preparation (Peptide)

The peptides according to the present invention may be prepared by any methods known in the art. Thus, the NPY-derived peptides may be prepared by standard peptide-preparation techniques such as solution synthesis or Merrifield-type solid phase synthesis.

In one embodiment, a peptide according to the invention is a non-naturally occurring peptide; being derived from a naturally occurring protein (NPY; SEQ ID NO:22). This applies especially to SEQ ID NOs:2-19.

In another embodiment, the peptide according to the invention is a naturally occurring peptide being derived from a naturally occurring protein (NPY; SEQ ID NO:22). This applies especially to SEQ ID NO:1, being a metabolic clearance or degradation product of NPY of hitherto no or unknown function.

In one embodiment a peptide according to the present invention is purified from a naturally occurring source thereof, such as serum. Protein purification is a series of processes intended to isolate a single type of protein from a complex mixture. The starting material is usually a biological tissue. The various steps in the purification process may free the protein from a matrix that confines it, separate the protein and non-protein parts of the mixture, and finally separate the desired protein from all other proteins. Separation steps may exploit differences in (for example) protein size, physico-chemical properties, binding affinity and biological activity.

In one embodiment a peptide according to the invention is synthetically made or produced.

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

In one embodiment the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Peptides may be synthesised either batch-wise on a fully automated peptide synthesiser using 9-fluorenylmethyloxycarbonyl (Fmoc) or tert-Butyloxycarbonyl (Boc) as N-a-amino protecting group and suitable common protection groups for side-chain functionalities.

After purification such as by reversed phase HPLC, peptides may be further processed to obtain for example cyclic or C- or N-terminal modified isoforms. The methods for cyclization and terminal modification are well-known in the art.

Peptides according to the invention may be synthesized as monomers or multimers such as dimers or tetramers (>80% purity, Schafer-N, Copenhagen, Denmark).

Administration and Dosage

According to the present invention, a peptide or a nucleic acid construct encoding said peptide, or a composition comprising a peptide as defined herein is administered to individuals in need of treatment in pharmaceutically effective doses or a therapeutically effective amount. The dosage requirements will vary with the particular drug composition employed, the route of administration and the particular subject being treated, which depend on the severity and the sort of the disorder as well as on the weight and general state of the subject. It will also be recognized by one skilled in the art that the optimal quantity and spacing of individual dosages of a peptide compound will be determined by the nature and extent of the condition being treated, the form, route and site of administration, and the particular patient being treated, and that such optima can be determined by conventional techniques. It will also be appreciated by one of skill in the art that the optimal course of treatment, i.e., the number of doses of a compound given per day for a defined number of days, can be ascertained using conventional course of treatment determination tests.

A 'bioactive agent' will be used to denote collectively a peptide, a nucleic acid construct encoding said peptide, and a composition comprising a peptide according to the present invention.

In one embodiment of the present invention, the bioactive agent is administered in doses of from 1 µg/day to 100 mg/day; such as from 1 µg/day to 10 µg/day, such as 10 µg/day to 100 µg/day, such as 100 µg/day to 250 µg/day, such as 250 µg/day to 500 µg/day, such as 500 µg/day to 750 µg/day, such as 750 µg/day to 1 mg/day, such as 1 mg/day to 2 mg/day, such as 2 mg/day to 5 mg/day, or such as 5 mg/day to 10 mg/day, such as 10 mg/day to 20 mg/day, such as 20 mg/day to 30 mg/day, such as 30 mg/day to 40 mg/day, such as 40 mg/day to 50 mg/day, such as 50 mg/day to 75 mg/day, or such as 75 mg/day to 100 mg/day.

In one embodiment of the present invention, one single dose of the bioactive agent is administered and may comprise of from 1 µg/kg body weight to 100 mg/kg body weight; such as from 1 to 10 µg/kg body weight, such as 10 to 100 µg/day, such as 100 to 250 µg/kg body weight, such as 250 to 500 µg/kg body weight, such as 500 to 750 µg/kg body weight, such as 750 µg/kg body weight to 1 mg/kg body weight, such as 1 mg/kg body weight to 2 mg/kg body weight, such as 2 to 5 mg/kg body weight, such as 5 to 10 mg/kg body weight, such as 10 to 20 mg/kg body weight, such as 20 to 30 mg/kg body weight, such as 30 to 40 mg/kg body weight, such as 40 to 50 mg/kg body weight, such as 50 to 75 mg/kg body weight, or such as 75 to 100 mg/kg body weight.

A dose according to the present invention may be administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day, wherein administration from 1 to 3 times per day is preferred. A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

Routes of Administration

It will be appreciated that the preferred route of administration will depend on the general condition and age of the subject to be treated, the nature of the condition to be treated, the location of the tissue to be treated in the body and the active ingredient chosen.

In one embodiment of the present invention, the route of administration allows for the bioactive agent to cross the blood-brain barrier.

Systemic Treatment

For systemic treatment according to the present invention the route of administration is capable of introducing the bioactive agent (a peptide, a nucleic acid construct encoding said peptide, and a composition comprising a peptide according to the present invention) into the blood stream to ultimately target the sites of desired action.

Such routes of administration are any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intracerebral, intravenous and intradermal administration).

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the bioactive agent may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

Local Treatment

The bioactive agent according to the invention may in one embodiment be used as a local treatment, i.e. be introduced directly to the site(s) of action. Accordingly, the bioactive agent may be applied to the skin or mucosa directly, or the bioactive agent may be injected into the site of action, for example into the diseased tissue or to an end artery leading directly to the diseased tissue.

These administration forms preferably avoid the blood brain barrier, and the blood-retina barrier.

Local Treatment—Injection into the Eye

In one particular embodiment, the bioactive agent according to the present invention is injected directly into the eye, i.e. into the vitreous humour of the eye. This is termed intravitreal or intraocular injection. This will allow the injected matter to reach also the retina lining the inner surface of the eye. After the pupil is dilated and the eye is numbed with anesthesia, the medication is injected into the vitreous, or jelly-like substance in the back chamber of the eye. The medication may be administered by an injection into the eye as needed at regular intervals.

In another embodiment, the bioactive agent according to the present invention is injected into the retina, such as one or more of the layers of the retina. In one embodiment, said administration is subretinal administration.

Preferably, injection into the eye will occur in order to allow the injected matter to reach the retina, such as the neurons of the retina. Instruments developed for performing vitrectomies (surgery to remove some or all of the vitreous humor from the eye), or instruments developed for silicone oil injection (filling of the eye with liquid silicone to hold the retina in place) may be employed for this purpose, including cannulas and syringes.

Patients may use eye drops for several weeks or longer to allow the surface of the eye to heal after injection. In some cases heavy lifting is avoided for a few weeks.

Local Treatment—Injection into the Brain Area

In one particular embodiment, the bioactive agent according to the present invention is applied or injected directly into the brain, such as into a specific region of the brain. Thus, an effect of the bioactive agent may be achieved in the region of the brain where it is mainly required. This may depend on the condition being treated. This may be termed intracerebral administration.

In another embodiment, the bioactive agent is administered via intrathecal administration or injection, i.e. in the space under the arachnoid membrane of the brain or spinal cord.

Pharmaceutical Formulation

Whilst it is possible for the bioactive agent of the present invention (a peptide, a nucleic acid construct encoding said peptide, and a composition comprising a peptide) to be administered as the raw chemical (peptide), it is sometimes preferred to present them in the form of a pharmaceutical formulation. Such a pharmaceutical formulation may be referred to as a pharmaceutical composition, pharmaceutically acceptable composition or pharmaceutically safe composition.

Accordingly, the present invention further provides a pharmaceutical formulation, which comprises a bioactive agent of the present invention, or a pharmaceutically acceptable salt or ester thereof, and a pharmaceutically acceptable carrier, excipient and/or diluent. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavouring agents, solubilizers, lubricants, suspending agents, binders, preservatives, wetting agents, tablet disintegrating agents, or an encapsulating material.

Examples of solid carriers are lactose, terra alba, sucrose, cyclodextrin, talc, gelatin, agar, pectin, acacia, magnesium stearate, stearic acid or lower alkyl ethers of cellulose.

Examples of liquid carriers are syrup, peanut oil, olive oil, phospholipids, fatty acids, fatty acid amines, polyoxyethylene, water, saline or a glucose solution. Similarly, the carrier or diluent may include any sustained release material known in the art, such as glycerol monostearate or glycerol distearate, alone or mixed with a wax.

Also included are solid form preparations which are intended to be converted, shortly before use, to liquid form preparations. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

The bioactive agent of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol.

Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The bioactive agent of the invention may also be formulated for topical delivery. Regions for topical administration include the eye or the cornea, the skin surface and also mucous membrane tissues of the vagina, rectum, nose, mouth, and throat. The topical formulation may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example.

Lotions according to the present invention also include those suitable for application to the eye. An eye lotion may comprise a sterile aqueous solution optionally containing a bactericide.

The formulations of the present embodiment may also include other agents useful for pH maintenance, solution stabilization, or for the regulation of osmotic pressure.

Pharmaceutically acceptable salts of the instant peptide compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The peptide compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Second Active Ingredients

The bioactive agent of the present invention may be combined with or comprise one or more second or further active ingredients which are understood as other therapeutical compounds or pharmaceutically acceptable derivatives thereof.

Methods for treatment according to the present invention may thus further comprise one or more steps of administration of one or more second active ingredients, either concomitantly or sequentially, and in any suitable ratios. Such second active ingredients may, for example, be selected from compounds used to treat or prevent symptoms and complications associated with a disease or disorder of the CNS or eye.

Methods of treatment according to the present invention may include a step wherein the pharmaceutical composition or peptide as defined herein is administered simultaneously, sequentially or separately in combination with one or more second active ingredients.

It follows, that co-administration should be targeted so that to optimise treatment of the patient, i.e. in a patient with multiple sclerosis, a drug approved for this specific purpose may be complemented with the peptide, compound or composition according to the present invention to optimise and improve treatment outcome for the patient. This is regardless of whether the approved drug for the specific purpose is prophylactic, ameliorating or curative.

In one embodiment, the bioactive agent of the invention is used in combination with an (one or more) agent(s) known for treating a disease or disorder of the eye or retina/optic nerve. In one embodiment said agent is capable of inhibiting VEGF (vascular endothelial growth factor), for example an anti-VEGF antibody, such as Avastin, Macugen and Lucentis, which are approved for treatment of macular degeneration, diabetic retinopathy and retinal vein occlusion. In one embodiment anti-VEGF treatment may inhibit the neuroprotective effects of VEGF, thus warranting the co-administration of an agent with neuroprotective effects, such as the bioactive agent of the invention.

Thus in one embodiment there is provided a method of treating a disease or disorder of the eye or retina/optic nerve comprising use of or co-administration of a bioactive agent of the present invention and an agent capable of inhibiting VEGF. Co-administration may in one embodiment be simultaneous, separate or sequential.

Thus in one embodiment there is provided a method of treating a disease or disorder of the eye or retina/optic nerve comprising use of or administration of a bioactive agent of the invention in connection with surgery such as eye surgery. Thus, the bioactive agent may in one embodiment be administered before eye surgery and/or during eye surgery and/or after eye surgery.

Thus in one embodiment there is provided a method of treating retinal detachment comprising administration of a bioactive agent of the invention in connection with eye surgery, such as before eye surgery and/or during eye surgery and/or after eye surgery.

In one embodiment, the bioactive agent of the invention is used in combination with other peptides or peptide fragments which are not derived from NPY. In one particular embodiment, said peptide is derived from BDNF or GDNF. In one particular embodiment the bioactive agent of the invention is used in combination with a GDNF peptide, such as the GDNF peptides disclosed in WO 2007/019860.

Kit-of-Parts

The present invention also relates to a kit-of-parts comprising one or more of the bioactive agents described above (a peptide, a nucleic acid construct or a composition), and at least one additional or further component.

A kit of parts according to the present invention comprises one or more of the bioactive agents as defined herein for treatment, prevention or alleviation of a disease or disorder of the CNS or eye. Kits according to the present invention allows for simultaneous, sequential or separate administration of the bioactive agent according to the present invention and/or one or more second active ingredients as described herein elsewhere.

Sequences

| SEQ ID NO | Description |
| --- | --- |
| SEQ ID NO: 1 | NPY3-35<br>SKPDNPGEDAPAEDMARYYSALRHYINLITRQR |
| SEQ ID NO: 2 | NPY4-35<br>KPDNPGEDAPAEDMARYYSALRHYINLITRQR |
| SEQ ID NO: 3 | NPY5-35<br>PDNPGEDAPAEDMARYYSALRHYINLITRQR |
| SEQ ID NO: 4 | NPY6-35<br>DNPGEDAPAEDMARYYSALRHYINLITRQR |
| SEQ ID NO: 5 | NPY7-35<br>NPGEDAPAEDMARYYSALRHYINLITRQR |
| SEQ ID NO: 6 | NPY8-35<br>PGEDAPAEDMARYYSALRHYINLITRQR |
| SEQ ID NO: 7 | NPY9-35<br>GEDAPAEDMARYYSALRHYINLITRQR |
| SEQ ID NO: 8 | NPY10-35<br>EDAPAEDMARYYSALRHYINLITRQR |
| SEQ ID NO: 9 | NPY11-35<br>DAPAEDMARYYSALRHYINLITRQR |
| SEQ ID NO: 10 | NPY12-35<br>APAEDMARYYSALRHYINLITRQR |
| SEQ ID NO: 11 | NPY13-35<br>PAEDMARYYSALRHYINLITRQR |
| SEQ ID NO: 12 | NPY14-35<br>AEDMARYYSALRHYINLITRQR |
| SEQ ID NO: 13 | NPY15-35<br>EDMARYYSALRHYINLITRQR |
| SEQ ID NO: 14 | NPY16-35<br>DMARYYSALRHYINLITRQR |
| SEQ ID NO: 15 | NPY17-35<br>MARYYSALRHYINLITRQR |
| SEQ ID NO: 16 | NPY18-35<br>ARYYSALRHYINLITRQR |

| SEQ ID NO | Description |
|---|---|
| SEQ ID NO: 17 | NPY19-35<br>RYYSALRHYINLITRQR |
| SEQ ID NO: 18 | NPY20-35<br>YYSALRHYINLITRQR |
| SEQ ID NO: 19 | NPY21-35<br>YSALRHYINLITRQR |
| SEQ ID NO: 20 | NPY22-35<br>SALRHYINLITRQR |
| SEQ ID NO: 21 | NPY23-35<br>ALRHYINLITRQR |
| SEQ ID NO: 22 | NPY1-36 (NPY, full-length NPY)<br>(Tyr36 amidated)<br>YPSKPDNPGEDAPAEDMARYYSALRHYINLITRQRY |
| SEQ ID NO: 23 | NPY21-36 (Tyr36 amidated)<br>YSALRHYINLITRQRY |
| SEQ ID NO: 24 | NPY23-36 (Tyr36 amidated)<br>ALRHYINLITRQRY |
| SEQ ID NO: 25 | NPY25-36 (Tyr36 amidated)<br>RHYINLITRQRY |
| SEQ ID NO: 26 | NPY27-36 (Tyr36 amidated)<br>YINLITRQRY |
| SEQ ID NO: 27 | NPY31-36 (Tyr36 amidated)<br>ITRQRY |
| SEQ ID NO: 28 | NPY1-30<br>YPSKPDNPGEDAPAEDMARYYSALRHYINL |
| SEQ ID NO: 29 | NPY3-30<br>SKPDNPGEDAPAEDMARYYSALRHYINL |
| SEQ ID NO: 30 | NPY1-20<br>YPSKPDNPGEDAPAEDMARY |
| SEQ ID NO: 31 | NPY21-34<br>YSALRHYINLITRQ |
| SEQ ID NO: 32 | Pro-NPY, UniProt Accession No.:<br>P01303<br>(NPY_HUMAN; 97 amino acids)<br>MLGNKRLGLS GLTLALSLLV CLGALAEAYP<br>SKPDNPGEDA PAEDMARYYS ALRHYINLIT<br>RQRYGKRSSP ETLISDLLMR ESTENVPRTR<br>LEDPAMW |
| SEQ ID NO: 33 | CPON<br>aa 68-97 of Pro-NPY (last 30 aa) |
| SEQ ID NO: 34 | NPY24-35<br>LRHYINLITRQR |
| SEQ ID NO: 35 | NPY3-35 reversed sequence<br>RQRTILNIYHRLASYYRAMDEAPADEGPNDPKS |
| SEQ ID NO: 36 | NPY21-35 ALA-21<br>ASALRHYINLITRQR |
| SEQ ID NO: 37 | Free acid NPY (C-terminal —OH)-<br>TYR30 not amidated<br>YPSKPDNPGEDAPAEDMARYYSALRHYINLITRQRY |
| SEQ ID NO: 38 | NPY3-36 (Tyr36 amidated)<br>SKPDNPGEDAPAEDMARYYSALRHYINLITRQRY |
| SEQ ID NO: 39 | NPY21-36 (Tyr36 amidated)<br>YSALRHYINLITRQRY |
| SEQ ID NO: 40 | NPY23-36 (Tyr36 amidated)<br>ALRHYINLITRQRY |
| SEQ ID NO: 41 | NPY23-36 ALA-36<br>ALRHYINLITRQRA |
| SEQ ID NO: 42 | NPY25-36 (Tyr36 amidated)<br>RHYINLITRQRY |
| SEQ ID NO: 43 | NPY27-36 (Tyr36 amidated)<br>YINLITRQRY |
| SEQ ID NO: 44 | NPY31-36 (Tyr36 amidated)<br>ITRQRY |

EXAMPLES

Example 1: Methods

Peptides

Peptides were synthesized as monomers from Schafer-N, Copenhagen, Denmark. If dimers or tetramers were used they consisted of two and four chains, respectively, coupled to a lysine backbone, as previously described (Pankratova et al., 2010).

Surface Plasmon Resonance Analysis

The analysis was performed with a Biacore 2000 machine (GE Healthcare, Hilleroed, Denmark). NCAM Ig1 module was immobilized on a sensor chip. NPY, NPY fragments or control molecules were infused over the chip. The data were analyzed by non-linear curve fitting using the software package BIAevaluation v.4 (GE Healthcare). The curves were fitted to a 1:1 Langmuir binding model, and rate and equilibrium constants were calculated. Cf. FIG. 1.

NPY Receptor Binding

Figure 2A:
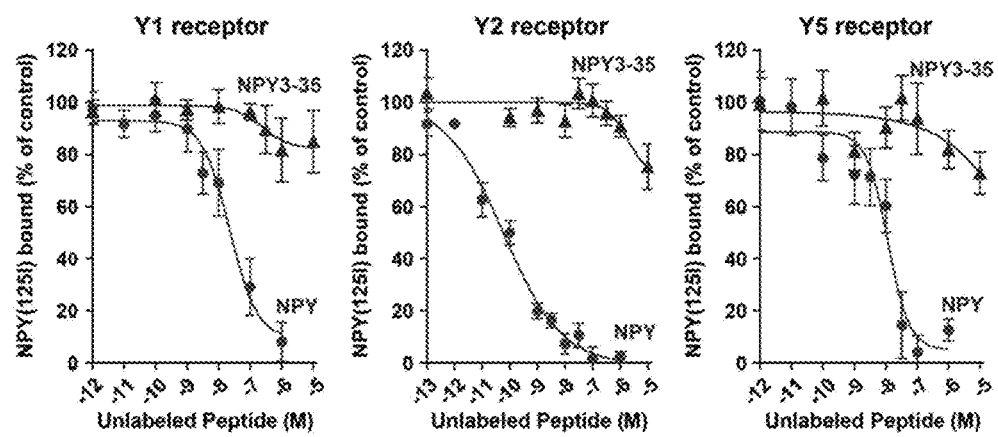
FIG. 2: NPY binds and activates G-protein coupled receptors Y1, Y2 and Y5, NPY3-35 does not. (a) NPY displaces $I^{125}$-NPY binding to cognate NPY receptors Y1, Y2 and Y5 in HEK293 cell cultures overexpressing Y1, Y2 or Y5 receptors, while NPY3-35 does not. (b) NPY but not NPY3-35 could stimulate activation of G-protein coupled receptors in the agonist stimulated [35S]GTPgammaS functional binding assay (scale bar=1 μm). (c) Quantitative measures of the levels of binding seen in (b). (d) NPY3-35 could displace 125I-labelled NPY3-35 binding NCAM-180-expressing HEK293 cells, but not after NCAM knockdown which per se decreased the 125I-labelled NPY3-35 binding. (e-f) NCAM knockdown was confirmed by immunoblotting.
Figure 3:
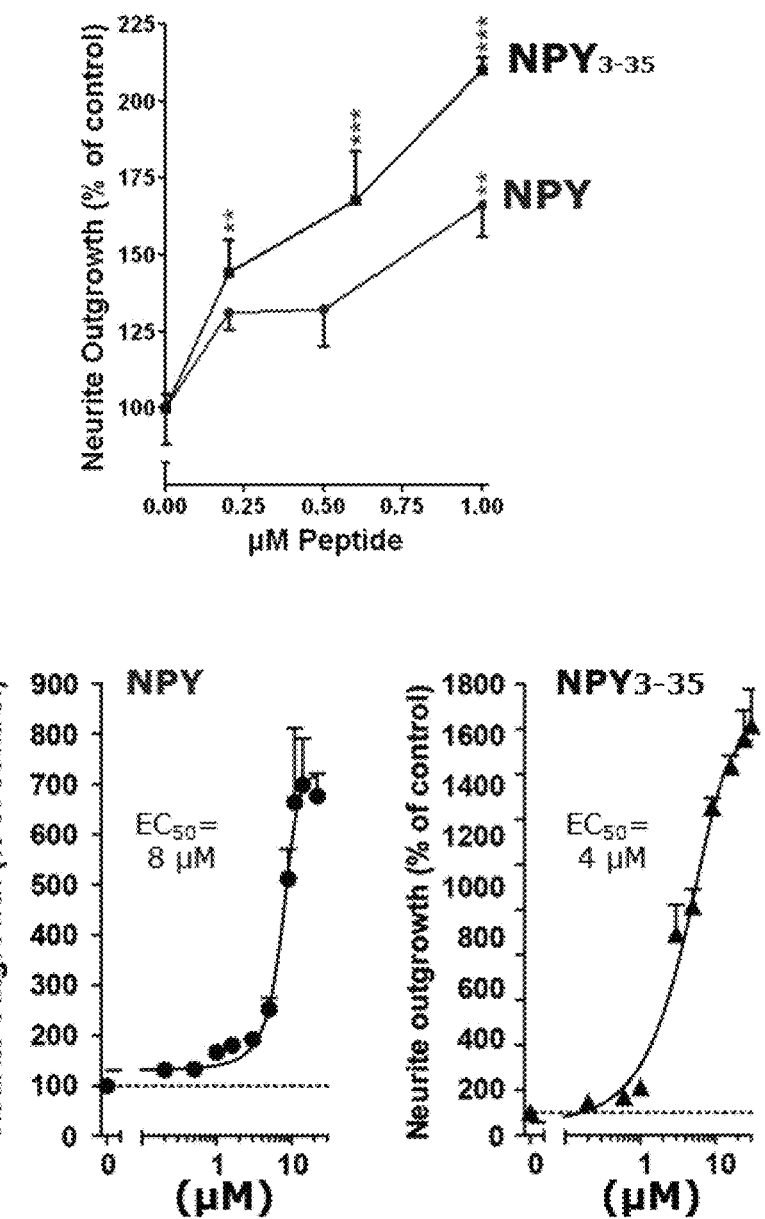
FIG. 3: NPY and NPY3-35 induce neurite outgrowth in E19 prenatal rat hippocampal cultures (24 h). $P<0.01$, *$P<0.001$ vs. control, Dunnett's post-hoc test after significant repeated-measures one-way ANOVA.
Figure 4:
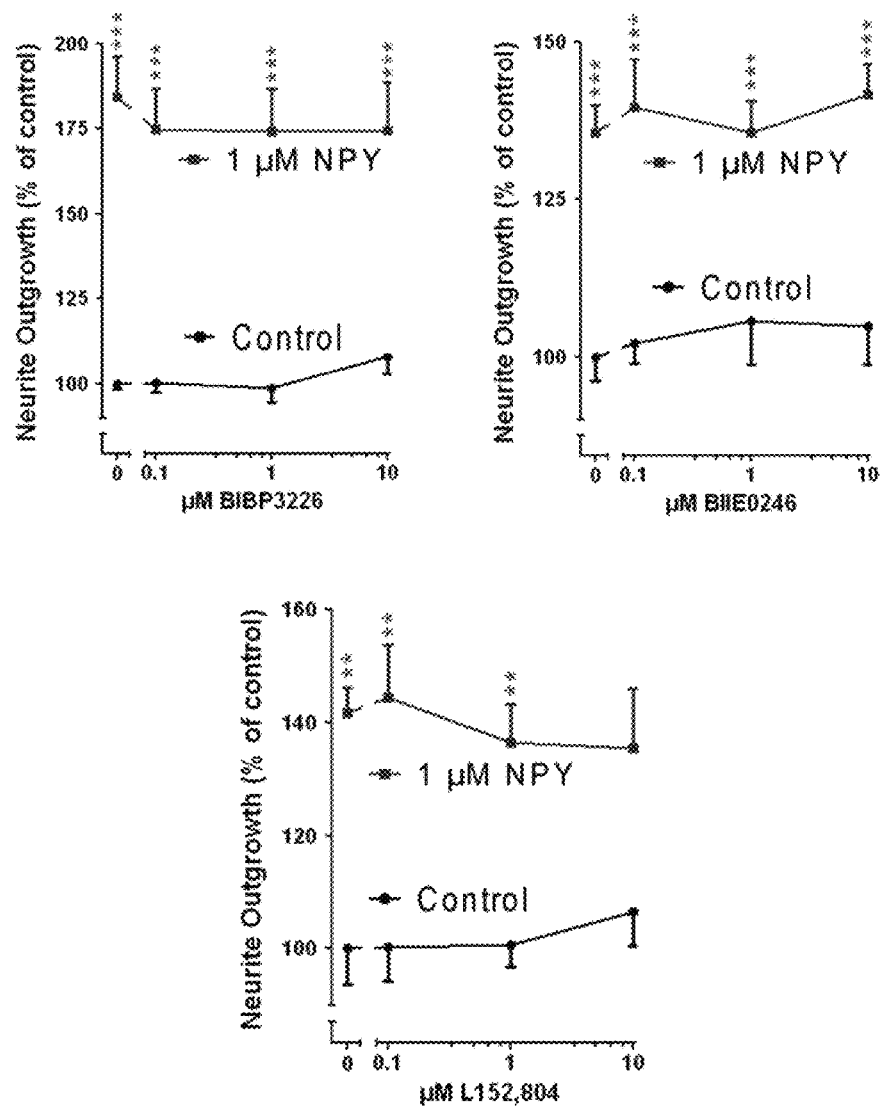
FIG. 4: The neuritogenic effect of NPY is not mediated through the cognate NPY-receptors Y1, Y2 and Y5; administration of NPY receptor agonists does not negatively affect neurite outgrowth induced by NPY (A: NPY Y1 receptor agonist BIBP3226; B: NPY Y2 receptor agonist BIIE0246 and C: NPY Y5 receptor agonist L-152,804). $P<0.01$, *$P<0.001$ vs. control, Dunnett's post-hoc test after significant repeated-measures one-way ANOVA.
Figure 5:
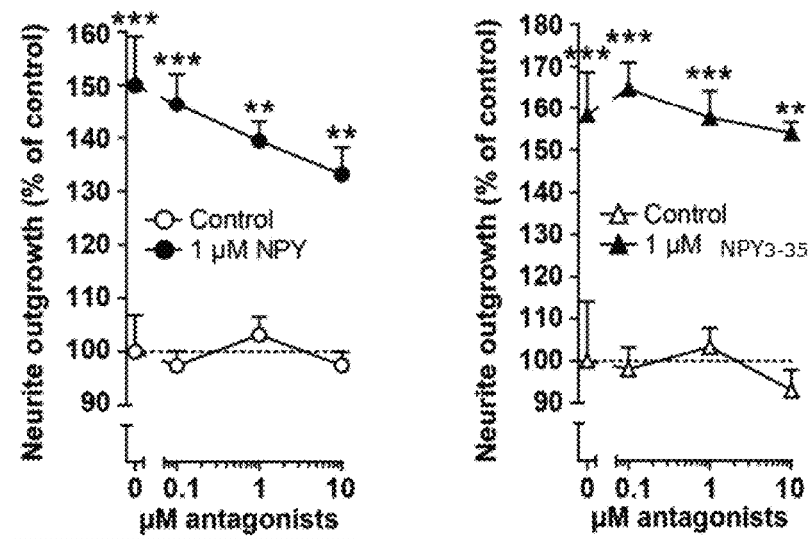
FIG. 5: The neuritogenic effect of NPY and NPY3-35 is not mediated through the cognate NPY-receptors Y1, Y2 and Y5; administration of NPY Y1, Y2 and Y5 receptor agonists BIBP3226, BIIE0246 and L-152,804 in combination does not negatively affect neurite outgrowth. $P<0.01$, *$P<0.001$ vs. control, Dunnett's post-hoc test after significant repeated-measures one-way ANOVA.
Figure 6:
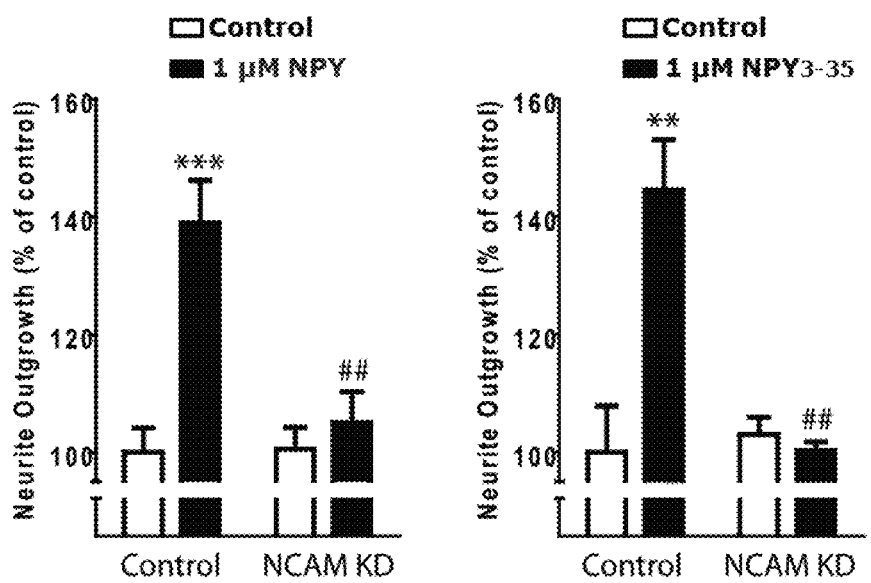
FIG. 6: The neuritogenic effect of NPY and NPY3-35 is mediated through interaction with NCAM as NCAM knockdown abolishes the beneficial effects of NPY and NPY3-35 on neurite outgrowth. Knockdown achieved with short-hairpin DNA plasmid targeting NCAM. $P<0.01$, *$P<0.001$ vs. corresponding control, ##$P<0.01$ vs. NPY- or NPY3-35-treated control cultures, Bonferroni post-hoc test after significant one-way ANOVA.
Figure 7:
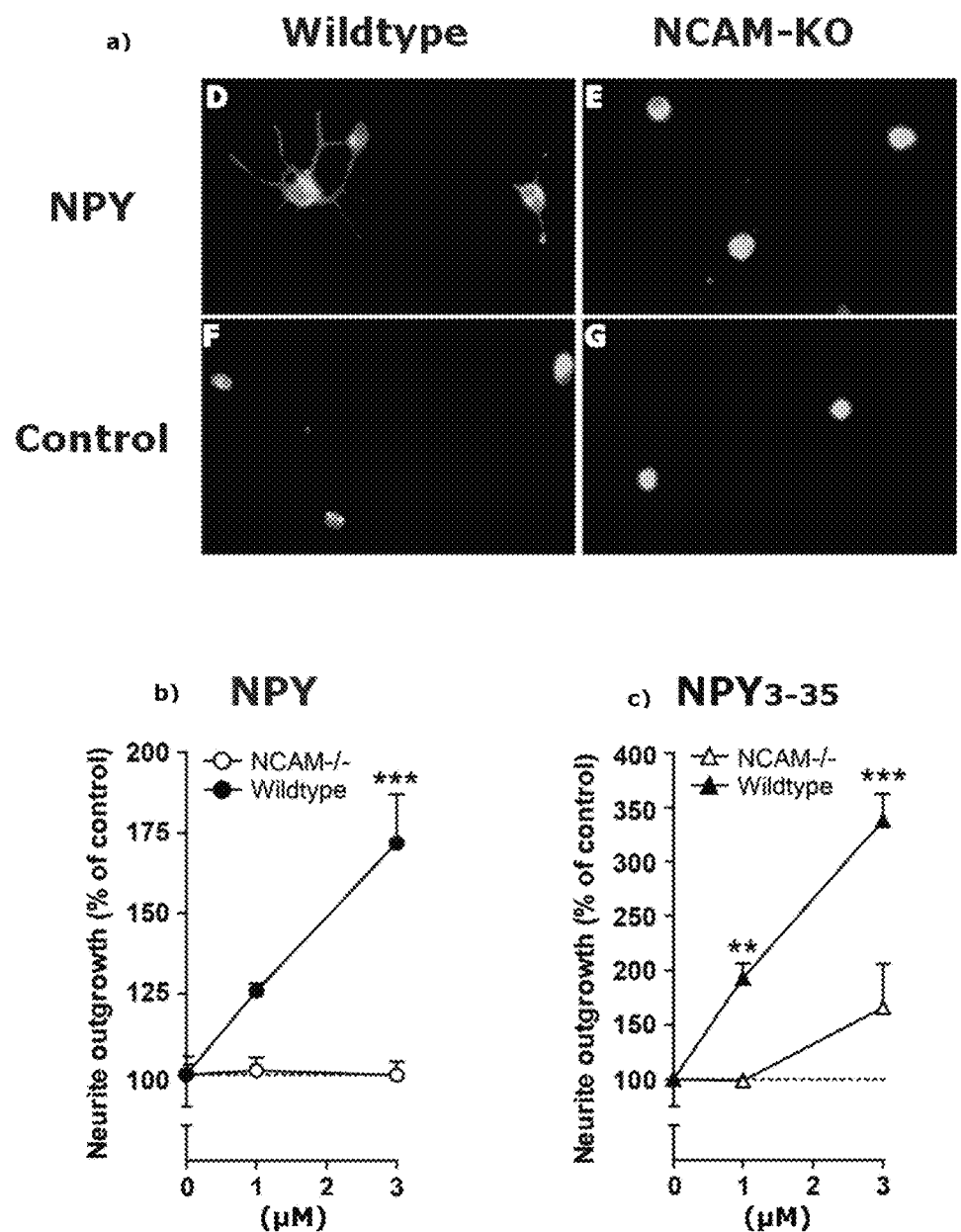
FIG. 7: NPY does not induce neurite outgrowth in NCAM-KO (knock-out) mice. (a) Microscopy. D: Neurite outgrowth in wild-type mouse neuronal cultures after addition of 9 μM NPY ligand. F: Neurite outgrowth in wild-type mouse neuronal cultures, control treatment. E: Neurite outgrowth in neuronal cultures from NCAM knock-out mice with addition of 9 μM NPY ligand. G: Neurite outgrowth in neuronal cultures from NCAM KO mice, control treatment. Prenatal cultures. (b-c) Graphical illustration of neuritogenic effect of NPY (a) and NPY3-35 (b) on wildtype and NCAM−/− cells (neuronal cultures from WT or NCAM KO mice). P<0.01, *P<0.001 vs. control, Dunnett's post-hoc test after significant repeated-measures one-way ANOVA.
Figure 8:
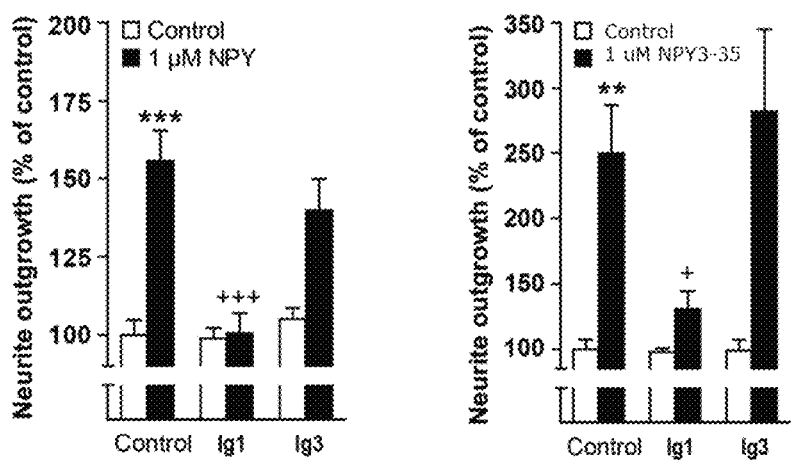
FIG. 8: NPY and NPY3-35 signalling via NCAM is blocked by addition of Ig1 module. Neuritogenic effects of NPY (left) and NPY3-35 (right) are abolished or diminished after addition of Ig1, not Ig3 module. P<0.01, *P<0.001 vs. control, +P<0.05, +++P<0.001 vs. NPY- or NPY3-35-treated control cultures, Bonferroni post-hoc test after significant one-way ANOVA.
Figure 9:
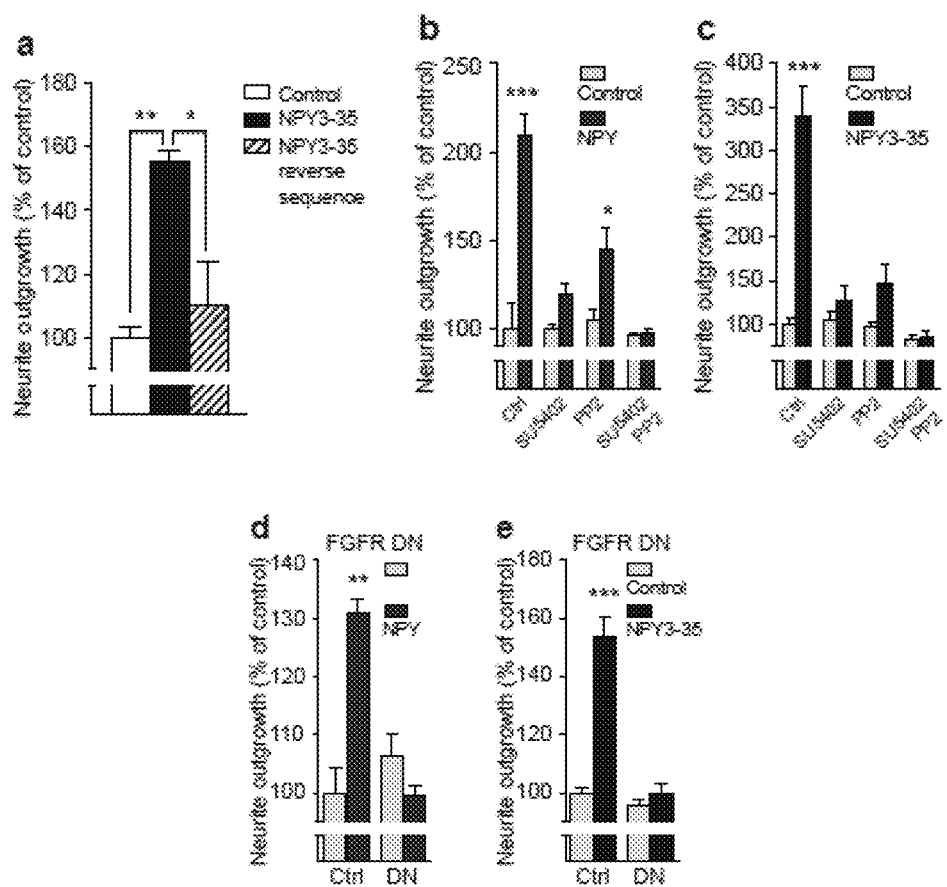
FIG. 9: Mechanisms of NPY and NPY3-35 neuritogenic effects in rat hippocampal neuron cultures. (a) A peptide with reverse sequence of NPY3-35 (YRQRTILNIYHR-LASYYRAMDEAPADEGPNDPKSPY; SEQ ID NO:45) did not induce the same neuritogenic effects as seen with NPY3-35. *: p<0.05, : p<0.01, compared to untreated controls (one-way ANOVA, follow by Dunnett's post hoc test n=2-6). (b-c) Inhibition of two well described signaling pathways used by NCAM when inducing neurite outgrowth, also abrogated the neuritogenic effects of NPY and NPY3-35. NPY and NPY3-35 induce NCAM-mediated neurite outgrowth via both Fyn/Fak and FGFR pathways. Use of specific pharmacological inhibitors of these pathways (PP2: Inhibititor of src family of tyrosine kinases (Fyn) and SU5402: Inhibitor of tyrosine kinase activity of FGFR1) inhibited the neuritogenic effects of NPY (b) and NPY3-35 (c) on neurite outgrowth. P<0.01, ***P<0.001 vs. control, #P<0.05, ##P<0.01, ###P<0.001 vs. NPY- or NPY3-35-treated cultures, Bonferroni post-hoc test after significant one-way ANOVA. (d-e) FGFR plays an important role in NPY and NPY3-35 induced neuritogenesis, as evident by the absent neuritogenic effects of (d) NPY and (e) NPY3-35 in cultures with kinase-defect dominant negative versions of FGFR1. *: p<0.05, : p<0.01, *: p<0.001, compared to untreated controls or control vector transfectants (repeated-measures one-way ANOVA, follow by Dunnett's post hoc test n=3-6).

HEK293 cells stably transfected to express NPY Y1, Y2 or Y5 receptors were treated with [$^{125}$I]-labeled NPY and subsequently supplied with rising concentrations of NPY or NPY3-35 to displace the cell bound [$^{125}$I]-labeled NPY. Cf. FIG. 2.

Neurite Outgrowth

Cultures of Wistar rat hippocampal neurons, embryonic stage day 19 (E19), seeded at a density of 12,500 cells/cm$^2$ in LabTek permanox slides and incubated for 24 hours (37° C., 5% $CO_2$) in supplemented neurobasal medium with raising concentrations of NPY or NPY3-35. When pharmacological inhibitors or antagonist are applied these are added to cultures 10 min prior to peptide addition. When soluble immunoglobulin modules are used, these are preincubated with peptide solution for 10 min before addition of the mix to the cultures. To knock down NCAM expression, the neurons were transfected with a p-GFP—V-RS vector that encodes short-hairpin RNA targeting NCAM (OriGene, Rockville, Md., USA) using a nucleofector device and a Rat Neuron Nucleofector kit (Amaxa, Gaithersburg, Md., USA). NCAM knock-out mice (C57Bl/6JZtm) were a kind gift from prof. Herbert Hildebrandt (Hannover Medical School) and were created as previous described (Cremer et al., 1994). The neurons were fixed, immunostained, and micrographs were recorded and evaluated as previously described (Rønn et al., 2000; Nielsen et al., 2009). Cf. FIGS. 3-9

Electrophysiology

Evoked fEPSPs

Figure 10:
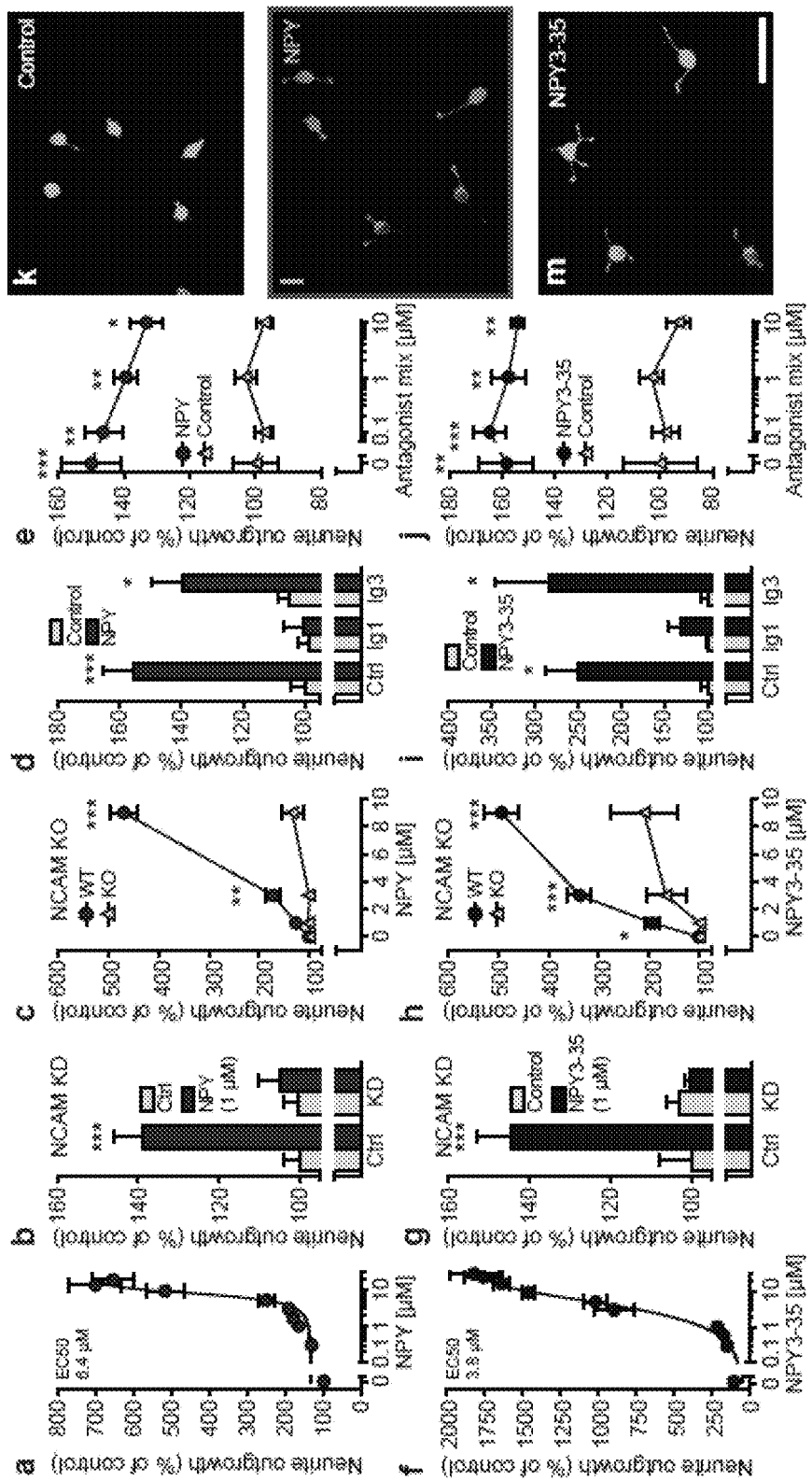
FIG. 10: NPY and NPY3-35 induce NCAM dependent neurite outgrowth. To investigate potential neuritogenic effects of NPY and derived peptides we added peptides to freshly prepared hippocampal neuronal cultures from rat fetuses, embryonic day 19. Neuritogenic effects of NPY (a) and NPY3-35 (f) were absent in neurons deprived of NCAM (b, g) and in neurons from NCAM (−/−) knockout mice (c, h). The neuritogenic effects of 1 µM NPY or NPY3-35 were also attenuated by addition of 1 µM soluble NCAM Ig1 but not Ig3 modules (d, i) whereas a mixture of NPY Y1, Y2, and Y5 receptor antagonists (Y1: BIBP3226, Y2: BIIE0246, Y5: L-152,804; 0.1-10 µM of each) was ineffective (e, j). *: p<0.05, : p<0.01, *: p<0.001, compared to untreated controls or control vector transfectants (repeated-measures one-way ANOVA, follow by Dunnett's post hoc test n=4-8. Representative images of cell cultures treated with vehicle (k), 1 µM NPY (l) or 1 µM NPY3-35 (m), scale bar=20 µm.

Naïve SD rats (n=14, all males, 42±2 days old, Charles River, Germany) were briefly sedated with isoflurane before decapitation. The skull was rapidly removed and the brain was immersed in ice-cold sucrose-based solution containing in mM: sucrose 75, NaCl 67, $NaHCO_3$ 26, Glucose 25, KCl 2.5, $NaH_2PO_4$ 1.25, $CaCl_2$ 0.5, $MgCl_2$ 7 (equilibrated with 5% $CO_2$ and 95% $O_2$, mean pH: 7.4 and mOsm: 308). Within the same solution, coronal slices of 400 μm thickness were cut on a Leica VT1200S vibratome. Slices were rested for >90 min at 34° C. in ACSF containing in mM: NaCl 119, $NaHCO_3$ 26, Glucose 25, KCl 2.5, $NaH_2PO_4$ 1.25, $CaCl_2$ 2.5, $MgSO_4$ 1.3; mean pH: 7.4 and mOsm: 303). In a submerged recording chamber, slices were constantly perfused with ACSF (32.5° C.) at a flow rate of 2.5 ml/min. Stimulation and recording electrode, both filled with ACSF (1.5-2 KiIn tip resistance) were placed in CA1 stratum radiatum. Current stimulation intensity was adjusted to generate 50-60% of maximal field excitatory postsynaptic potential (fEPSP). Paired-pulse stimulations (i.e. fEPSP1 and fEPSP2) with interstimulus interval of 50 ms were applied at 0.067 HZ throughout the entire experiment. Once stable fEPSPs were generated for 10 min or more, a 10 min baseline was acquired. Average amplitudes of fEPSP1 between groups were not different during baseline recordings (NPY3-35, 1.13±0.05 mV; NPY1-36, 0.94±0.08 mV; ACSF: 1.05±0.04 mV; p=0.08, one-way ANOVA). Next, NPY3-35 (1 μl), NPY1-36 (1 μl) or ACSF (control solution) was applied for 10 min during recordings. To avoid excessive loss of peptide and to avoid cross-contamination, silicon tubing and separate Sylgard silicon-coated glass bottles were used for each condition (i.e. NPY3-35, NPY1-36, ACSF). Recordings were continued for another 60 min. Data was acquired at 20 kHz using HEKA EPC-10 amplifier and PATCHMASTER software (HEKA Elektronik, Lambrecht/Pfalz, Germany). FITMASTER software (HEKA Elektronik) was used for off-line analysis. Four consecutive paired-pulse fEPSPs were averaged and expressed per min. For each recording, field EPSPs amplitudes (fEPSP1) were normalized to individual baseline values, and averaged per group. Changes in paired-pulse facilitation was calculated as the average ratio of [fEPSP2]/[fEPSP1] at 1-10, 21-30 and 71-80 min. Cf. FIG. 10.

Mouse Hippocampus LTP Protocol

Slice Preparation

Hippocampal slices were obtained from the left hemisphere of juvenile C57BL/6N mice (Taconic) (P12-22). After decapitation para-sagittal slices (300 μm) were cut on a vibratome (MicroM slicer HM 650V equipped with cooling unit CU65), while the tissue was immersed in ACSF of the following composition: (in mM NaCl, 125; KCl, 2.5; $NaHCO_3$, 26; $NaH_2PO_4$—$H_2O$, 1.25; $MgCl_2$, 1; $CaCl_2$, 2; Glucose, 25; bubbled with 5% $CO_2$ in 95% $O_2$). The slices rested in oxygenated ACSF (35° C.) for at least 1 hour before measurements were performed.

Long Term Potentiation (LTP) Protocol

Hippocampal slices were obtained from the left hemisphere of juvenile C57BL/6N mice (Taconic) (P12-22). After decapitation para-sagittal slices (300 μm) were cut on a vibratome (MicroM slicer HM 650V equipped with cooling unit CU65), while the tissue was immersed in ACSF of the following composition: (in mM NaCl, 125; KCl, 2.5; $NaHCO_3$, 26; $NaH_2PO_4.H_2O$, 1.25; $MgCl_2$, 1; $CaCl_2$, 2; Glucose, 25; bubbled with 5% $CO_2$ in 95% 02). The slices rested in oxygenated ACSF (35° C.) for at least 1 hour before measurements were performed.

Figure 11:
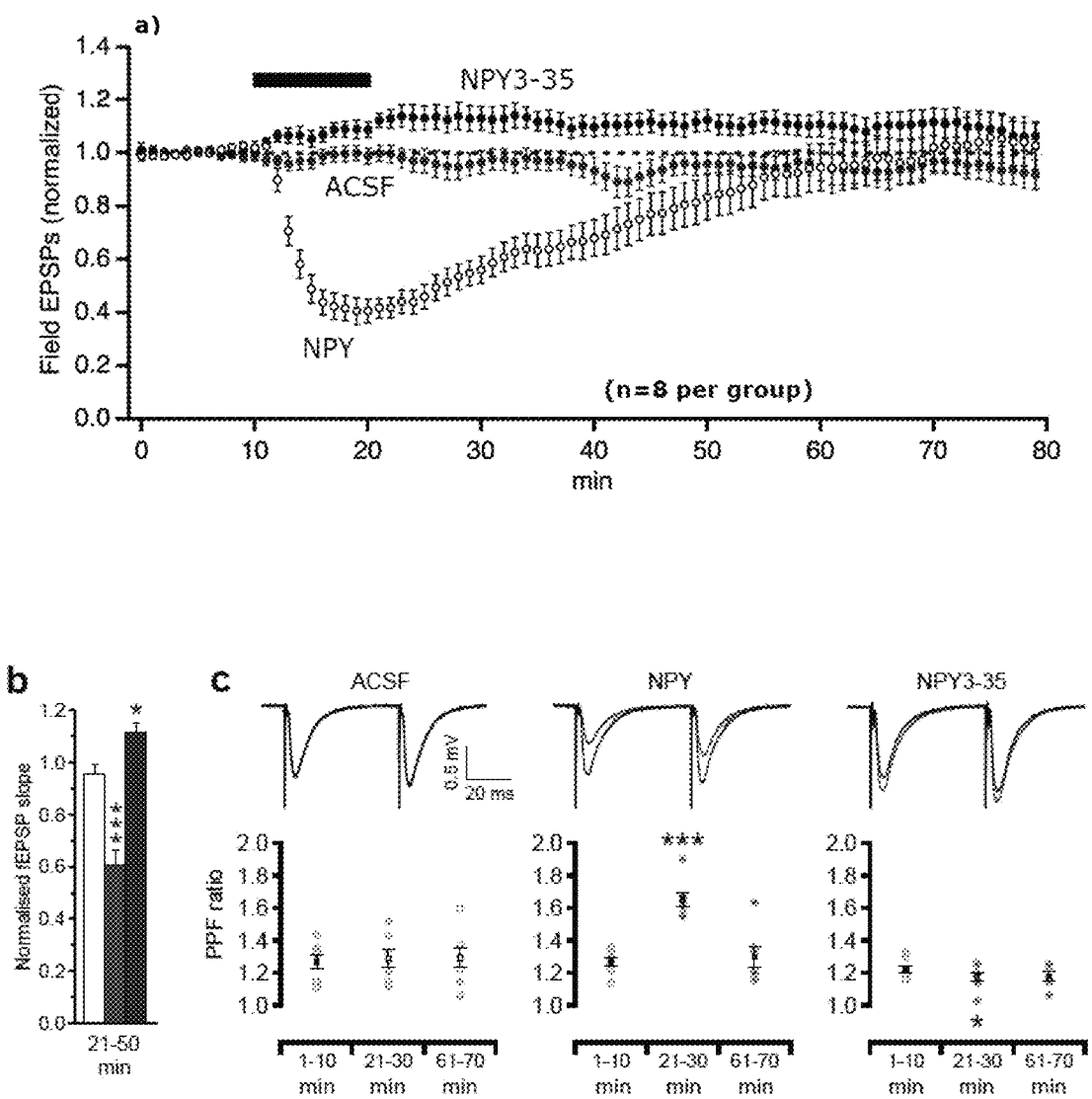
FIG. 11: Differential effects of NPY and NPY3-35 on synaptic neurotransmission in the hippocampus. (a) In acute rat slice preparations, supplication of NPY3-35 caused a slight but significant increase in the magnitude of evoked fEPSPs (fast excitatory postsynaptic potentials) when compared to ACSF (artificial cerebrospinal fluid (control)) in CA1 synapses, whereas NPY strongly attenuated the magnitude of fEPSPs. ACSF is without effect. Paired pulse stimulation in the stratum radiatum of the rat CA1 Schaffer collateral-CA pyramidal synapse. 0.067 Hz stimulation. Stimulation and recording electrodes are both in the CA1 stratum radiatum. Solid black horizontal bar shows 10-min period for peptide application. (b) NPY3-35 application causes a small, but significant, increase in the magnitude of evoked fEPSPs as revealed by the average during 30 min after the application of peptide has ended. *p<0.05, ***p<0.001 vs. ACSF, Bonferroni-adjusted post-hoc t-test following significant one-way ANOVA. (c—bottom) Consistent with a stimulatory effect on excitatory transmission, the paired-pulse facilitation (PPF) ratio decreases slightly following NPY3-35 application whereas NPY induces significant increase in the PPF ratio (1-10 vs. 21-30 min). At 61-70 min, complete washout is observed for NPY, but not for NPY3-35. (c—top) The PPF ratio is unaltered during ACSF conditions. Representative traces show average paired-pulse fEPSPs recorded during baseline (1-10 min, black lines) and after peptide/ACSF application (21-30 min, red lines NPY, blue line NPY3-35). Scale bar applies for all traces. *p<0.05, p<0.01, *p<0.001, paired t-test; NPY, n=8 slices, 7 animals; NPY3-35, n=8 slices, 7 animals; ACSF, n=8 slices, 4 animals.

Measurements were performed in oxygenated ACSF at room temperature (1.1 ml/min). Schaeffer collaterals were stimulated with a bipolar concentric electrode. The field potential in the stratum radiatum of CA1 was recorded with an extracellular glass microelectrode (4-6 MO, filled with ACSF), positioned at least 500 μm away from the stimulation electrode. The stimulus intensity was set 0.03 mA above threshold. After a 15-min baseline obtained while stimulating at 0.05 Hz, a treatment consisting either of ACSF, NPY 3-35 (1 μM), NPY 3-35 (1 μM)+Ig1 (1 μM) or NPY (1 μM) was applied to the extracellular medium. After 15 min, LTP was induced by stimulating the Schaeffer collaterals at 100 Hz for 1 s, 4 times with a 20 s interval. A new baseline was established over the following 30 min with continuous treatment. Potentiation was estimated by measuring the rising slope of the field EPSP (fEPSP). Cf. FIG. 11

Spatial Memory in the Morris Water Maze Test

Figure 12:
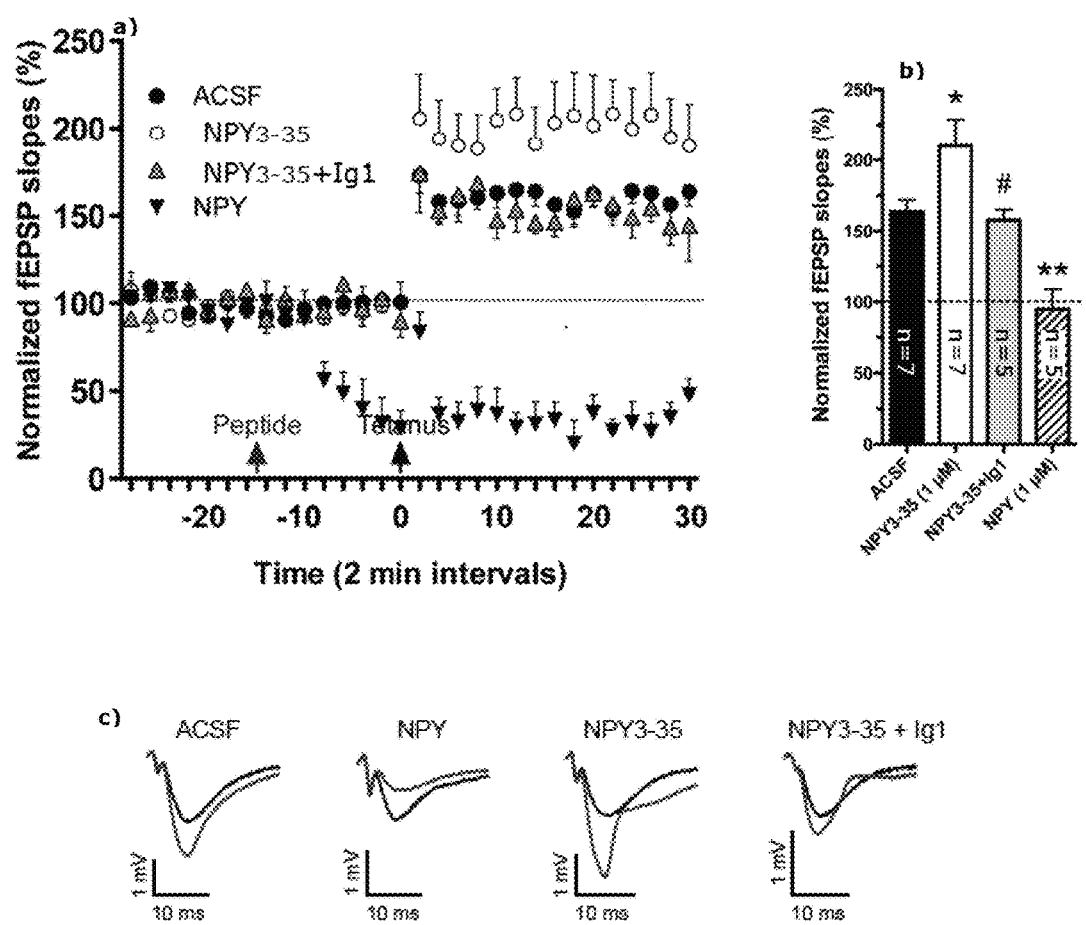
FIG. 12: NPY3-35 enhances LTP (long term potentiation) in the mouse hippocampus while NPY inhibits LTP a) Effect of NPY3-35 is blocked by addition of soluble Ig1 module, confirming involvement of NCAM Ig1 module in mediating the effects of NPY3-35 on LIP. Rat Schaeffer collateral CA1 pyramidal synapses were stimulated and the field potentials in the stratum radiatum of CA1 were recorded. The stimulus intensity was set 30 µA above threshold. After 15-min baseline was obtained by stimulating at 0.05 Hz. Subsequently (first arrow), either NPY3-35 (1 µM; n=7), NPY3-35+Ig1 (both 1 µM; n=5), NPY (1 µM; n=5), or control ACSF (n=8) was applied to the extracellular medium. After 15 min (second arrow), LIP was induced by stimulating the Schaffer collaterals. Data are normalized to 15-min baseline before application of peptide. (b) Statistical analysis of the average effect on fEPSP slopes during the 30-min after induction of LTP normalized to 10-min interval immediately before induction of LTP, confirms the effects reported in d. *p<0.05, **p<0.01, Bonferroni-adjusted post-hoc t-test following significant one-way ANOVA. (c) Traces showing average effects on fEPSPs during baseline (black curves) and after induction of LIP (lighter curves).
Figure 13:
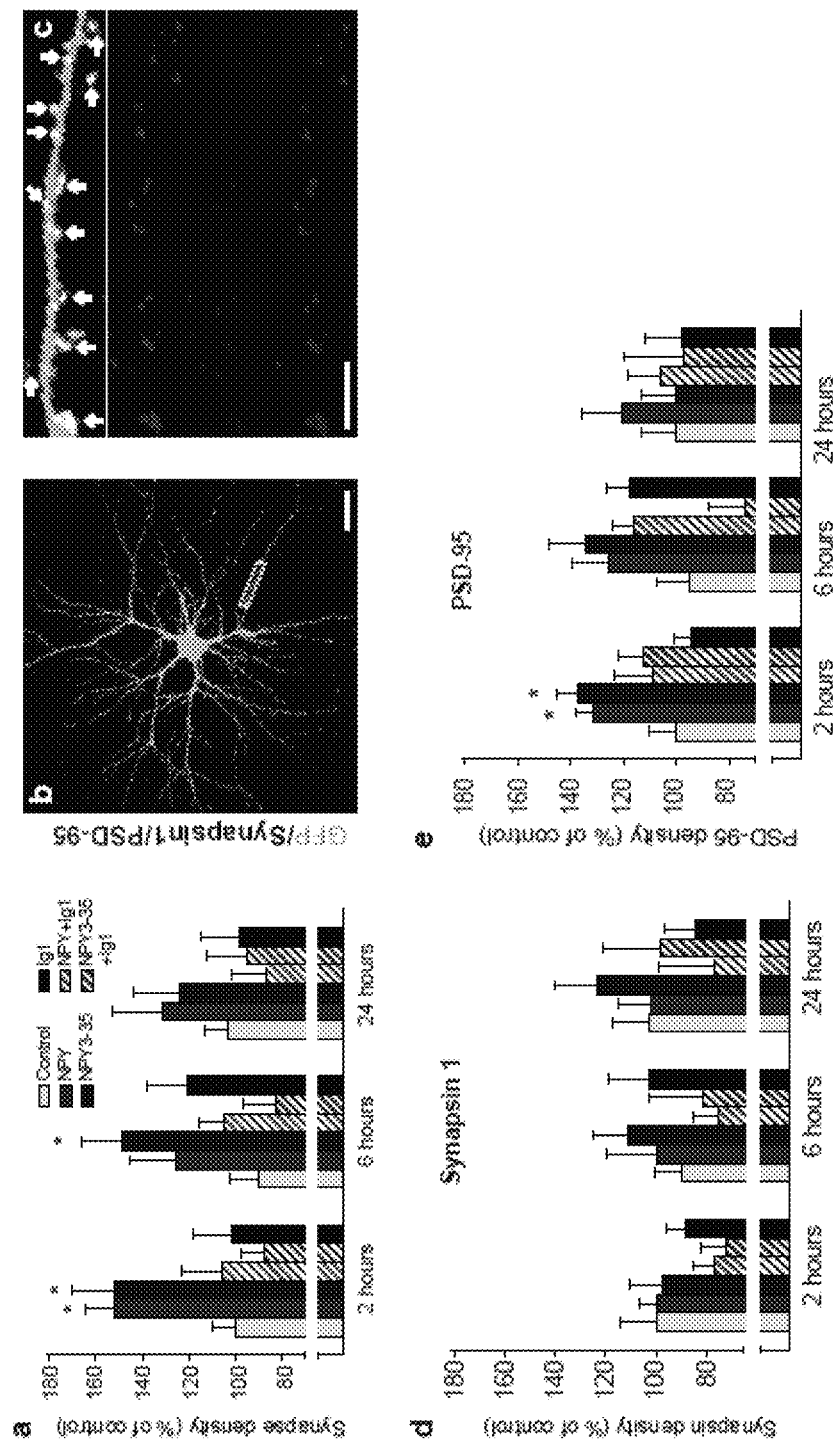
FIG. 13: NPY and NPY3-35 increase the synaptic densities in a NCAM-dependent manner in hippocampal neurons. Rat hippocampal neurons were seeded on a confluent glia cell layer in culture chamber slides, and grown for 14 days (37° C., 5% CO2). After the first 6 days, in vitro, the cultures were lipofectamin transfected with a plasmid with the coding sequence for green fluorescence protein. At day 14, 1 µM of NPY or NPY3-35 were added 2, 6, or 24 hours before the cultures were fixated and immunostained for presynaptic protein synapsin 1 and presynaptic protein PSD-95. Punctas with colocalized GFP-positive cells (green), synapsin 1 (red) and PSD-95 (blue) were regarded as synapses and the synapse density was estimated from total number of punctas per area. To investigate NCAM dependence of any effects a subset of cultures were incubated with peptide together with soluble NCAM Ig1. a) NPY and NPY3-35 significantly increased synaptic density at 2 hours, and NPY3-35 also after 6 hours, an effect which was shown to be NCAM dependent since co-incubation with NCMA Ig1 abolished the effect. b) Representative micrograph of one of the neurons in the study (scale bar 20 µm). c) Magnified dendrite from the boxed area in FIG. 13b, with white arrows pointing to synaptic punctas (scale bar 4 µm). The observed NPY and NPY3-35 induced upregulations in synaptic densities was only correlated with upregulations in e) postsynaptic PSD-95, whereas no changes was seen in d) synapsin 1 levels. Statistics: *P<0.05 versus control, one-way ANOVA, followed by Tukeys post hoc test (control n=9, NPY n=7-9, NPY3-35 n=7-8, NPY+Ig1 n=6, NPY3-35+Ig1 n=5-6, Ig1 n-3-5).
Figure 14:
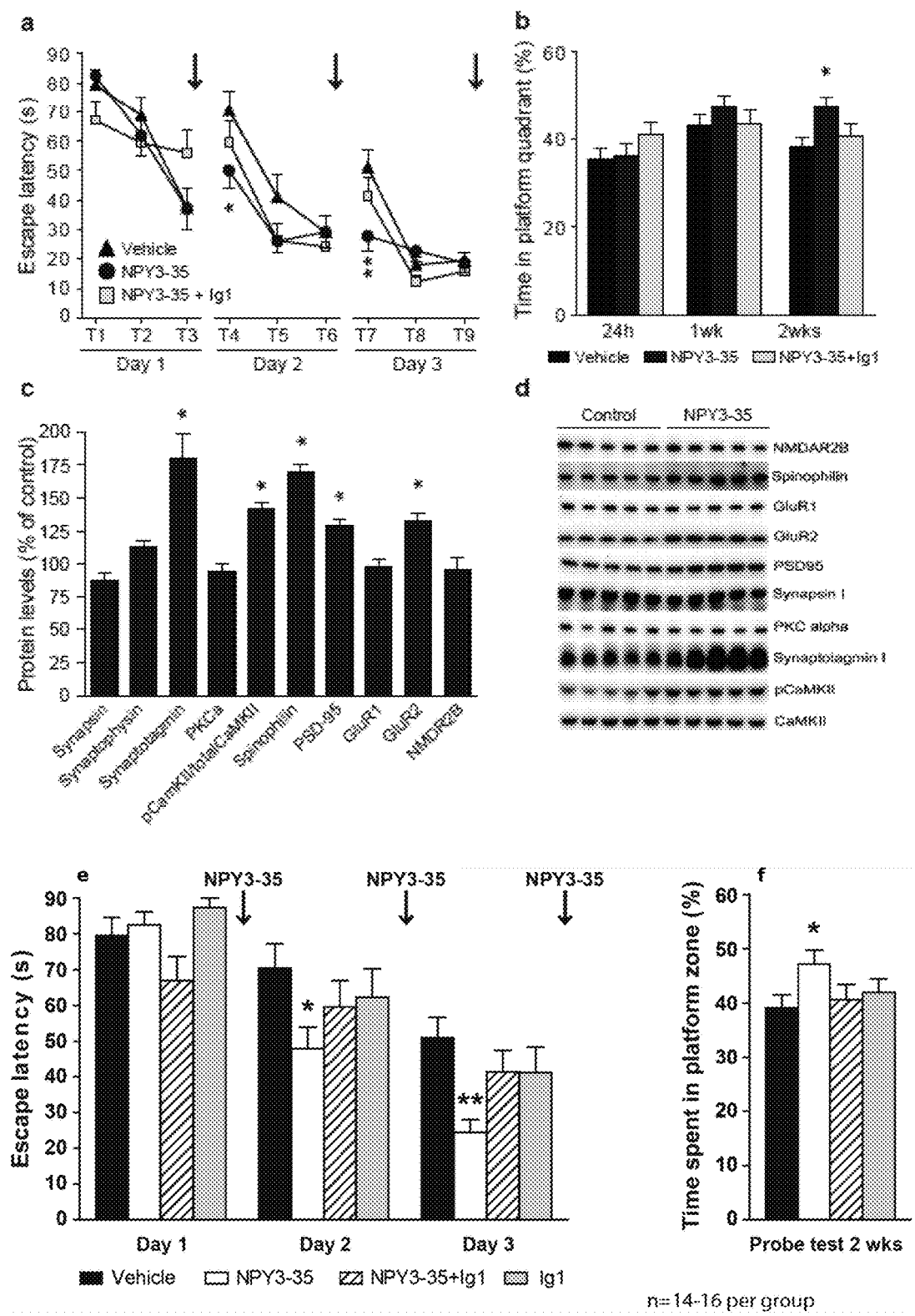
FIG. 14: NPY3-35 improves consolidation of spatial memory in rats performing the water maze test. NPY3-35 treated animals display shorter escape latencies to find platform at the first trial on day 2 and 3 (a:T4 and T7) of training than vehicle treated rats indicating improved memory of platform location.

The Morris water maze test was a 160 cm wide circular black tank placed in a dimly lit room and filled with 21° C. water up to 20 cm from the top. The tank was surrounded by visual orientation marks, and a 10 cm wide escape platform was placed 1.5 cm below the surface for it to be unseen. A video camera was placed above the tank and connected to a computerized tracking system (Ethovision 3.1, Noldus IT, Wageningen, the Netherlands). The tank was divided into 4 equally large quadrants that also served as starting positions. The escape latency time to locate the platform and the time spent in each quadrant was recorded. Prior to training, an intracerebroventricular cannula was inserted in the anaesthetized rats and the animals were allowed 1 week for recovery. The rats were handled 2 min daily for 5 days prior to start of the experiment. Reference memory training consisted of 3 consecutive trials daily for 3 days. Each trial started with the animal being placed in the water facing the wall of the pool. The starting position differed for each trial but was identical for all animals. In each trial, the animal was allowed 90 s to locate the platform. The animals that did not find the platform were guided to the platform and given a latency score of 90 s. After each trial, the rats were allowed 20 s of orientation time on the platform and then removed from the pool for 20 s before the next trial was initiated. After the last trial each day, the animals were dried and returned to their home cages. On the first 3 days immediately after training, the animals were given an intracerebroventricular 4 μl injection of NPY3-35 or PBS/1% BSA solution. To test for the effects on long-term memory, the animals were given a 60 s probe test 24 h, 1 and 2 weeks after reference memory training. In the probe tests, the platform was removed, and the animals started from a position in a quadrant adjacent to the original platform quadrant. At the end of the probe test, the animal was guided to the reintroduced platform and allowed to stay there for 20 s. Subsequently, after the 24 h and the 1 week probe test, the animal was given one relearning test under conditions identical to reference memory training to counteract memory extinction. Cf. FIGS. 12a-b Kainate-Induced Cytotoxicity Cultures of rat hippocampal neurons, embryonic stage day 19 (E19), seeded at a density of 50,000 cells/cm² in poly-L-lysine coated LabTek permanox slides. Cultures were incubated for 7 days (37° C., 5% $CO_2$) in supplemented neurobasal medium and treated with raising concentrations of NPY or NPY3-35. 1 hour later 300 mM kainate was added and cultures were incubated for 24 hours before being fixed, stained and analysed as previous described (Pankratova et al., 2010). Cf. FIG. 13

REFERENCES

Cremer, H., et al. *Nature* 367:455-459 (1994)
Nielsen J., et al. *J. Neurosci.* 29, 11360-11376 (2009)
Pankratova S., et al. *Brain.* 133:2281-2294 (2010)
Rønn L. C., et al. *J. Neurosci. Methods.* 100, 25-32 (2000)
Berglund et al. 2003: Recent developments in our understanding of the physiological role of PP-fold peptide receptor subtypes. Exp. Biol. Med. 228, 217-244.

Example 2: Neurite Outgrowth

Neurite outgrowth in cultures of hippocampal neurons from wistar rats, embryonic stage day 19, incubated for 24 hours (37° C., 5% $CO_2$) in supplemented Neurobasal medium with NPY fragments added; effect compared to un-stimulated controls (set to 100%). Values are mean normalized to un-stimulated controls±standard error of mean (SEM). *P<0.05, P<0.05, *P<0.05, Student's t-test versus un-stimulated control.

| NPY Sequences tested (tested sequence in bold, underlined) | Neuritogenic effect | |
|---|---|---|
| | 1 µM NPY fragment (% of control) | 3 µM NPY fragment (% of control) |
| $NPY_{1-36}$ (full-length: SEQ ID NO: 22)<br>YPSKPDNPGEDAPAEDMARYYSALRHYINLITRQRY | 166.3 ± 12.0<br>(n = 4)* | 180.3 ± 13.5<br>(n = 4)* |
| $NPY_{3-36}$ (SEQ ID NO: 38)<br>YPSKPDNPGEDAPAEDMARYYSALRHYINLITRQRY | 112.1 ± 5.8<br>(n = 4) | 164.7 ± 11.7<br>(n = 4)** |
| $NPY_{21-36}$ (SEQ ID NO: 39)<br>YPSKPDNPGEDAPAEDMARYYSALRHYINLITRQRY | 107.8 ± 4.9<br>(n = 8) | 186.5 ± 25.8<br>(n = 8)** |
| $NPY_{23-36}$ (SEQ ID NO: 40)<br>YPSKPDNPGEDAPAEDMARYYSALRHYINLITRQRY | 107.2 ± 5.0<br>(n = 4) | 156.1 ± 14.0<br>(n = 4)** |
| $NPY_{23-36}$ ala36 (SEQ ID NO: 41)<br>YPSKPDNPGEDAPAEDMARYYSALRHYINLITRQRA | 89.1 ± 8.0<br>(n = 2) | 91.7 (n = 1) |
| $NPY_{25-36}$ (SEQ ID NO: 42)<br>YPSKPDNPGEDAPAEDMARYYSALRHYINLITRQRY | 95.9 ± 7.8<br>(n = 4) | 96.1 ± 4.3<br>(n = 3) |
| $NPY_{27-36}$ (SEQ ID NO: 43)<br>YPSKPDNPGEDAPAEDMARYYSALRHYINLITRQRY | 106.6 ± 6.3<br>(n = 3) | 99.1 ± 4.5<br>(n = 2) |
| $NPY_{31-36}$ (SEQ ID NO: 44)<br>YPSKPDNPGEDAPAEDMARYYSALRHYINLITRQRY | 100.2 ± 2.3<br>(n = 2) | 91.8 ± 8.3<br>(n = 2) |
| $NPY_{3-35}$ (SEQ ID NO: 1)<br>YPSKPDNPGEDAPAEDMARYYSALRHYINLITRQRY | 210.1 ± 4.2<br>(n = 7)*** | 889.4 ± 131.4<br>(n = 4)*** |
| $NPY_{3-35}$ reversed sequence (SEQ ID NO: 35)<br>YRQRTILNIYHRLASYYRAMDEAPADEGPNDPKSPY | 109.9 ± 15.7<br>(n = 4) | 285.3 ± 100.9<br>(n = 4)<br>N.S., P = 0.08 |
| $NPY_{4-35}$ (SEQ ID NO: 2)<br>YPSKPDNPGEDAPAEDMARYYSALRHYINLITRQRY | 185.4 ± 8.1<br>(n = 3)** | 637.3 ± 22.0<br>(n = 3)*** |
| $NPY_{5-35}$ (SEQ ID NO: 3)<br>YPSKPDNPGEDAPAEDMARYYSALRHYINLITRQRY | 193.5 ± 5.8<br>(n = 3)*** | 605.0 ± 9.8<br>(n = 3)*** |
| $NPY_{6-33}$ (SEQ ID NO: 4)<br>YPSKPDNPGEDAPAEDMARYYSALRHYINLITRQRY | 165.9 ± 10.0<br>(n = 3)** | 683.1 ± 65.7<br>(n = 3)*** |
| $NPY_{8-35}$ (SEQ ID NO: 6)<br>YPSKPDNPGEDAPAEDMARYYSALRHYINLITRQRY | 163.7 ± 19.3<br>(n = 3)* | 909.4 ± 66.7<br>(n = 3)*** |
| $NPY_{10-35}$ (SEQ ID NO: 8)<br>YPSKPDNPGEDAPAEDMARYYSALRHYINLITRQRY | 169.1 ± 10.6<br>(n = 3)** | 709.4 ± 11.3<br>(n = 3)*** |
| $NPY_{13-35}$ (SEQ ID NO: 11)<br>YPSKPDNPGEDAPAEDMARYYSALRHYINLITRQRY | 174.23 ± 6.9<br>(n = 2)*;<br>164.2 ± 7.2<br>(n = 4)*** | 305.43 ± 26.3<br>(n = 2)*;<br>275.8 ± 31.2<br>(n = 4)*** |
| $NPY_{21-35}$ (SEQ ID NO: 19)<br>YPSKPDNPGEDAPAEDMARYYSALRHYINLITRQRY | 154.20 ± 20.4<br>(n = 2)*;<br>154.1 ± 8.7<br>(n = 4)*** | 232.69 ± 42.8<br>(n = 2)*;<br>266.4 ± 26.6<br>(n = 4)*** |
| $NPY_{21-35}$ ala21 (SEQ ID NO: 36)<br>YPSKPDNPGEDAPAEDMARYASALRHYINLITRQRY | 95.4 ± 4.5<br>(n = 2) | 94.1 ± 6.8<br>(n = 2) |
| $NPY_{1-30}$ (SEQ ID NO: 28)<br>YPSKPDNPGEDAPAEDMARYYSALRHYINLITRQRY | 76.9 (n = 1) | 98.7 (n = 1) |
| $NPY_{1-20}$ (SEQ ID NO: 30)<br>YPSKPDNPGEDAPAEDMARYYSALRHYINLITRQRY | 97.84 ± 5.5<br>(n = 4) | 99.09 ± 4.1<br>(n = 4) |
| $NPY_{22-35}$ (SEQ ID NO: 20)<br>YPSKPDNPGEDAPAEDMARYYSALRHYINLITRQRY | 103.96 ± 0.5<br>(n = 2) | 91.42 ± 12.8<br>(n = 2) |

-continued

| NPY Sequences tested (tested sequence in bold, underlined) | Neuritogenic effect | |
|---|---|---|
| | 1 µM NPY fragment (% of control) | 3 µM NPY fragment (% of control) |
| NPY$_{23-35}$ (SEQ ID NO: 21)<br>YPSKPDNPGEDAPAEDMARYYSALRHYINLITRQRY | 96.25 ± 6.0<br>(n = 4) | 103.68 ± 10.0<br>(n = 4) |
| NPY$_{24-35}$ (SEQ ID NO: 34)<br>YPSKPDNPGEDAPAEDMARYYSALRHYINLITRQRY | 96.9 ± 5.6<br>(n = 3) | 103.2 ± 10.5<br>(n = 3) |
| NPY$_{21-34}$ (SEQ ID NO: 31)<br>YPSKPDNPGEDAPAEDMARYYSALRHYINLITRQRY | 87.7 ± 9.6<br>(n = 2) | 97.5 ± 6.9<br>(n = 2) |
| NPY$_{3-30}$ (SEQ ID NO: 29)<br>YPSKPDNPGEDAPAEDMARYYSALRHYINLITRQRY | 88.64 ± 8.3<br>(n = 4) | 105.07 ± 5.7<br>(n = 4) |
| Free acid NPY (C-terminal —OH)<br>(SEQ ID NO: 37)<br>YPSKPDNPGEDAPAEDMARYYSALRHYINLITRQRY | 124.4 ± 10.7<br>(n = 5)* | 179.6 ± 17.3<br>(n = 5)*** |

Example 3: Neuroprotective Effect of NPY-Derived Peptides in Mixed Retinal Cell Cultures The neuroprotective effect on the survival of retinal cells of NPY-derived peptides of the present invention can be demonstrated in the following way:

Wistar rat pups (3-5 days old) are sacrificed to prepare primary mixed cultures of retinal cells. Retinas are dissected under sterile conditions, using a light microscope, in Ca2+- and Mg2+-free Hanks' balanced salt solution containing: 137 mM NaCl, 5.4 mM KCl, 0.45 mM KH2PO4, 0.34 mM Na2HPO4, 4 mM NaHCO3, 5 mM glucose, pH 7.4), and digested with 0.1% trypsin (w/v) for 15 min at 37° C. Cells were diluted in MEM, supplemented with 25 mM Hepes, 26 mM NaHCO3, 10% FBS and penicillin (100 U/mL)-streptomycin (100 µg/mL), and plated on poly-D-lysine (0.1 mg/mL)-coated coverslips or 24-multiwell plates for 3-9 days, at a density of 2×10$^6$ cells/cm$^2$ (37° C., 5% CO2). Staining with [3,8-diamino-5-(3-(diethylmethylamino)propyl)-6-phenyl phetananthri-dinium diiodide] (PI) as a Marker of Retinal Cell Death:

PI is a marker of dying cells with disrupted cell membranes due to necrosis or late apoptosis, and binds to DNA emitting a bright red fluorescence (630 nm) when excited by blue-green light (493 nm). Retinal cells plated on coverslips are exposed to the toxic substance 3,4-methylenedioxymethamphetamine (MDMA; 400-1600 µM), glutamate (500 µM) or kainate for 24 h-48 h, at 37° C. Retinal cells not treated with the toxic substances are used as control. To demonstrate the neuroprotective effect of NPY-derived peptides, the retinal cells are simultaneously incubated with one or more NPY-derived peptides (e.g. 100 nM to 100 µM). After drug incubations, the cells are washed twice and incubated with PI (0.04 mg/mL) for 3 min, and then observed with a fluorescence microscope (Zeiss Axioshop 2 Plus) coupled to an Axiocam HRc camera. The number of PI-positive retinal cells is subsequently counted in five random fields in each coverslip.

The neuroprotective effect of the NPY-derived peptides is demonstrated as a significant decrease in the number of PI-positive retinal cells induced by MDMA, glutamate or kainate after treatment with the NPY-derived peptides compared to the control condition.

Immunocytochemistry to Show Neuroprotection on Specific Populations of Retinal Cells:

The neuroprotective effect of NPY-derived peptides on selective types of retinal cells is demonstrated using immunocytochemistry. Thus rat retinal neural cells plated on coverslips as described above are exposed to MDMA (400-1600 µM), glutamate (500 µM) or kainate (30-150 µM) for 24 h-48 h at 37° C. After incubation, retinal cells are washed twice with phosphate-buffered saline (PBS) (137 mM NaCl, 27 mM KCl, 18 mM KH2PO4, 100 mM Na2HPO4, pH 7.4) and fixed with 4% paraformaldehyde for 20 min at room temperature. Cells are permeabilized with 1% TritonX-100 for 5 min at room temperature, and non-specific binding of the antibodies is prevented by incubation with 3% (w/v) fatty acid-free bovine serum albumin containing with 0.2% Tween20 for 1 h. Cells are then incubated for 90 min at room temperature with appropriate concentrations of the primary antibody: mouse anti-TUJ1 (neuronal marker), mouse anti-PKC (amacrine cells), or mouse anti-Brn3a (ganglion cell marker). After incubation, cells are washed three times with PBS and incubated with anti-mouse secondary antibodies at appropriate concentrations for 1 h at room temperature in the dark. After 5 min washing, cell nuclei are stained for 5 min with Hoechst 33342 (1 µg/mL in PBS). Cells are washed twice in PBS and mounted using a Prolong Antifade Kit (Dako Cytomation, Glostrup, Denmark). All antibody solutions are prepared in 3% fatty acid-free BSA solution. Retinal cells are visualized with a Zeiss Axioshop 2 Plus microscope, coupled to an Axiocam HRc camera.

The neuroprotective effect of NPY-derived peptides on neuronal retinal cells is demonstrated by increased number of the different types of retinal neuronal cells. Since the loss of retinal cells is centrally involved in the loss of vision in several eye disorders, neuroprotective effect of NPY-derived peptides demonstrates that these peptides are useful for treatment of eye diseases with retinal damage.

Example 4: Pig Model of Acute Retinal Ischemia

The neuroprotective effect on the survival and function of retinal cells of NPY-derived peptides according to the present invention can be demonstrated by using a pig model of acute retinal ischemia (previously described in Kyhn et al., 2009, Exp Eye Res 89:1012-20).

Induction of Retinal Ischemia for 2 Hours

Three month old female pigs of Danish Landrace/Duroc/Hampshire/Yorkshire breed receive an anesthetic cocktail of Tiletamine 1.19 mg/kg, Zolazepam 1.19 mg/kg (Zoletil 50 Vet Virbac SA, Carros, France), Methadone 0.24 mg/kg (Nycomed, Roskilde, Denmark), Ketamine 1.43 mg/kg (Intervet, Skovlunde, Denmark), and Xylazine 1.24 mg/kg (Intervet, Skovlunde, Denmark). Thereafter the anesthesia is maintained with continuous intravenous infusion of propofol 15 mg/kg/h (Fresenius Kabi, Bad Homburg, Germany). After induction the pigs are relaxed with pancuriumbromide 0.1 mg/kg (Organon, Holland). The animals are endotracheally intubated and artificially ventilated on 34% oxygen. The animals are placed resting on their elbows, to minimize the impact on the cardiovascular system. To prevent hypothermia, the pigs are wrapped in a blanket during anesthesia. Treatment of the animals adheres to the ARVO Statement for the Use of Animals in Ophthalmic and Vision Research.

Ischemia in the retina is induced in the following way. Through catheterization of the femoral artery the mean arterial blood pressure (MAP) is monitored. The intraocular pressure (IOP) is controlled by a 23 G cannula syringe inserted in the anterior chamber of the eye, and connected to an elevated bottle of Ringer Lactate. The ocular perfusion pressure (OPP=MAP−IOP) is clamped at 5 mmHg for 2 h by adjusting the height of the Ringer Lactate bottle. This procedure causes severe, reproducible ischemic damage to the inner retina and particularly its ganglion cells, as evidenced by multifocal electroretinography (mfERG) and quantitative histology (Kyhn et al., 2009). Before induction of retinal ischemia in the pigs, baseline mfERG recording is performed as described below. Immediately after termination of 2 h of ischemia, the NPY-derived peptides of the invention dissolved in isotonic saline are injected intravitreally in one eye in a volume of 0.1-0.2 ml to achieve concentrations in the range of 1-100 µM based on calculations that the intraocular volume is approximately 4 ml. A control group receives intravitreal saline injection.

Induced mfERG Recording

Multifocal stimulation is performed with VERIS Science 5.0.1. Visual stimuli are displayed on a 1.5-inch fundus/stimulation camera (Electro-Diagnostic Imaging, San Mateo, Calif., USA). Recordings are obtained by a Burian-Allen bipolar contact lens electrode (BA) (VERIS Infrared (IR) Illuminating Electrode; EDI Inc., San Mateo, Calif., USA) with hydroxypropyl methylcellulose 2% (Excelvision, Annonay, France) contact fluid. A reference electrode is placed behind the contralateral ear. The animals, as well as the respirator, are electrically grounded. The fundus area is monitored by means of a transpupillary IR light source. All recordings are performed in the same examination room, lit only by artificial light (28 cd/m$^2$). Pupils of the eyes are dilated to a diameter >8 mm with phenylephrine hydrochloride 10% (Metaoxedrin, SAD, Sonderborg, Denmark), topicamide 0.5% (Mydriacyl, Alcon, Puurs, Belgium) and atropine 1% (Atropin, SAD, Sonderborg, Denmark). Recordings are performed on both eyes after 15 min of light adaptation.

The mfERG stimulus used to record the induced mfERG response consists of a total of four frames: an initial pseudorandom frame, followed by a dark frame, a full-flash frame and finally another dark frame. A stimulus of 241 unscaled hexagons is used, m-exponent 15. One-segment recordings are performed at a frame rate of 75 Hz, with 16 samples per frame. Mean luminance is 100 cd/m$^2$. Responses are band-pass filtered outside of 10-300 Hz. Total recording length is 14.37 min. The stimulus grid and display luminance are calibrated as recommended by the ISCEV standards. We measure the induced (late) components of the mfERG as previously described (Kyhn et al., 2009). Recorded traces are divided into three groups: 1) the optic nerve head, 2) the inferior retina and 3) the visual streak. For each induced mfERG recorded, we identify the hexagons connected to the visual streak group and calculate the average amplitude. These averages are used for further analysis. The highest changes in the amplitudes are observed in the first induced negative component (iN1) and in the second induced positive component (iP2), therefore only these components are evaluated (Kyhn et al., 2009).

Histology

After the last induced mfERG recording, the eyes are enucleated for histological examination and the pigs euthanized by intravenous injection of 2-4 g pentobarbital (Pentobarbital 200 mg/ml, KVL, Copenhagen, Denmark). Globes are placed in 4% paraformaldehyde (PFA) for 10 min and the anterior segment and lens are removed. The posterior segment is post-fixed for 2 h in 4% PFA, with subsequent rinsing in increasing sucrose concentrations in Sorensen's phosphate buffer. A vertical cut is made extending from the superior retinal margin to 2-3 mm inferior to the optic disc, This comprises the superior ciliary margin, the visual streak and the optic disc. The tissue is embedded in gelatin medium and serially sectioned at 12 µm on a cryostat. For histopathological examination, sections are stained with Hematoxylin-Eosin (Htx-Eosin). The degree of perivasculitis is evaluated on a four step scale (0-3): 0=no perivasculitis; 1=discrete perivasculitis up until the maximum seen in normal eyes as a result of prolonged anesthesia and delay between euthanasia and fixation; 2=clearly pathological perivasculitis limited to the immediate vicinity of the vessels; and 3=severe perivasculitis with inflammation also present in adjacent layers of the retina). The perivasculitis is scored by an experienced histopathologist masked to the treatment of the pigs. Three sections from each eye are scored and the mean score from each eye is used for statistical analysis.

Immunohistochemical detection of neurons in the ganglion cell layer is performed using a mouse monoclonal antibody, antineuronal nuclei (NeuN) (1:100, MAB377, Chemicon International, Temecula, Calif., USA). Sections are incubated in a moist chamber for 16-18 h at 4° C., followed by rinsing in 0.1 M phosphate-buffered saline (PBS) with 0.25% Triton-X-100. Subsequently, sections are incubated with secondary FITC-conjugated antibodies (1:100, Jackson Immunoresearch, West Grove, Pa., USA) for 1-2 h at room temperature in the dark. Normal eyes, processed in parallel, are used as controls. The specimens are examined using an epifluorescence microscope equipped with the software Analysis Docu 3.2 (Soft Imaging System GmbH, Muenster, Germany) used in the cell counting.

Cell Counting of Retinal Ganglion Cells

For each histological section, an overview was created by mounting adjacent images magnified at 20 times. A grid (500×500 µm) is then placed onto the overview image. The number of NeuN positive cells in the ganglion cell layer with visible nucleoli is then counted. This process is repeated along the vertical meridian, starting from the superior disc margin in zones and ending 11,000 µm away. Zones 500 µm wide are counted and, in order to avoid overlap, zones of 500 µm are skipped between counted zones. Three sections (with a minimum of three sections between each used for measurements) from each pig are used, and the average cell count from the three sections is used. Measurements of normal eyes (three sections from each) are used as controls.

Analysis of the Neuroprotective Effect of NPY-Derived Peptides on the Retina

The neuroprotective effect of NPY-derived peptides of the invention compared to saline on the function of the retina is demonstrated by analysing mfERG recorded both before ischemia (i.e. baseline) and at 2 and 4 weeks after ischemia. We measure the ratio of the amplitudes of the iN1 and the iP2 components between the left (experimental) eye and the right (control) eye of the pigs. The neuroprotective effect on function is revealed by better mfERG signal in the NPY-derived peptide treated group compared to saline.

In the eyes of the same animals, the neuroprotective effects of NPY-derived peptides is demonstrated histologically by increased survival of NeuN-positive cells in the retinal ganglion cell layer at 2 and 4 weeks after induction of acute retinal ischemia. mfERG and histological analysis will be performed by persons blinded to the treatment of the animals.

Example 5: Neuroprotective Effect of NPY-Derived Peptides in Retinal Detachment Model in Cynomolgus Monkeys The neuroprotective effect on retinal function of NPY-derived peptides of the invention can be further demonstrated in a retinal detachment model using Cynomolgus monkeys.

The eyes of most animal species are quite different from the human eye, making it difficult to transfer results to the treatment of human retinal diseases. Limiting factors include the size of the eye (rodents), the retinal blood-supply (rabbits), the photoreceptor type and distribution (cats, rabbits and ground-squirrels), special properties like the tapetum lucidum (cat) and the cellular reaction to retinal detachment (rabbit and ground-squirrel). Another limiting factor, in most animal models, is the lack of a special feature of the human eye called the fovea. The fovea is a small area where high visual acuity is generated (reading, recognizing faces, and distinguish small details of an image). The retinal physiology of the fovea, explains the severe visual loss in patients with retinal diseases affecting this particular area. The fovea is located in the central part of the retina, it's only oxygen supply is from the underlying choroid. In contrast, the peripheral retina has a duplex oxygen supply consisting of an intraretinal and a choroidal arterial network. Hence, the fovea represents a central avascular zone. In the disease retinal detachment the central retina is affected so that the fovea is separated from choroidea and thereby from its blood supply. This results in foveal ischemia and neuroretinal damage leading to permanent visual loss in the affected eye.

It is not possible to establish an animal model for retinal detachment in pigs, the eyes of which in many ways resemble the human eye except for the lack of a regular fovea. The porcine retina tolerates retinal detachment far better than humans. In the porcine model, the retinal function, as measured by mfERG, remained normal despite seeks weeks of detachment (Sorensen N F et al., 2012, Graefes Arch Clin Exp Ophthalmol 250:79-86). This is different from humans, where studies have shown loss of function within seven days of detachment. In humans, the prognosis for visual acuity declines when the fovea is detached. Some of the difference in retinal function following retinal detachment, between the porcine and the human eye, can be explained by the difference in retinal transduction. The central vision in the porcine retina is gathered in an area called "the visual streak", where each bipolar cell receives stimulus from several photoreceptors. In comparison, the ratio between cone:bipolar cell:ganglion cell in the human fovea is 1:1:1. A central avascular foveal structure is only found in higher primates (humans and non-human primates) and birds of prey. The eye of a bird of prey is structurally different from the human eye in several aspects, and it is technically challenging to perform surgery and follow-up examinations on birds with the same equipment as used for human patients. Ideally, a non-human primate Cynomolgus monkey model is used to demonstrate a neuroprotective effect of NPY-derived peptides in retinal detachment.

Retinal Detachment Procedure:

Cynomolgus monkeys are anesthetized by administration of midazolam, Zoletil, Narcoxyl, Ketalar, Metadon and for maintenance: Haldid, Mebumal and Pavulon. Subsequently, a tube is inserted into the trachea of the animal for artificial ventilation (intubation).

During the anesthesia, an operation is conducted on the corpus vitreum of one eye of the Cynomolgus monkey where three holes approximately 0.7 mm in size are made through the sclera. The corpus vitreum is removed and at the same time substituted by water containing salt. After this, a small amount (0.1 ml) of salty water or a substance resembling the corpus vitreum (healon) will be injected into the retina, inducing a localized retinal detachment. Subsequently, the Cynomolgus monkeys will receive an injection (0.1-0.2 ml volume) into the eye of one or more NPY-derived peptides dissolved in isotonic saline aiming for a concentration of 1-100 µM (based on an estimated intraocular volume of 2 ml) or isotonic saline (control). Afterwards, bimanual palpation and indirect ophthalmoscopy is performed to exclude complications, and topical chloramphenicol ointment is given. Both before and 4-6 weeks after retinal detachment, the retinal function will be evaluated by multifocal electroretinography (mfERG) and the animals will be euthanized to allow for histological examination of the retina.

The neuroprotective effect of NPY-derived peptides on retinal function and neuronal survival in the retinal detachment model is demonstrated by increased signal in mfERG and increased number of surviving retinal neurons seen histologically after treatment with NPY-derived peptides compared to saline-treated eyes.

Items

1. An isolated peptide consisting of a peptide sequence of from 15 to 33 contiguous amino acid residues derived from neuropeptide Y (SEQ ID NO:22),
    wherein said peptide comprises the sequence YSAL-RHYINLITRQR (NPY21-35; SEQ ID NO:19), or a functional variant having at least 60% sequence identity to SEQ ID NO:19, wherein said peptide does not comprise the Tyr amino acid of position 36 of SEQ ID NO:22,
    for use in a method of treating a disease or disorder of the central nervous system and/or the eye.
2. The peptide for use according to item 1, wherein said peptide is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or
    a functional variant having at least 60% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

3. An isolated peptide consisting of a peptide sequence of 15 to 32 contiguous amino acid residues derived from neuropeptide Y (SEQ ID NO:22),
   wherein said peptide comprises the sequence YSALRHYINLITRQR (NPY21-35; SEQ ID NO:19), or a functional variant having at least 60% sequence identity to SEQ ID NO:19,
   wherein said peptide does not comprise the Tyr amino acid of position 36 of NPY (SEQ ID NO:22).
4. The peptide according to item 3, wherein said peptide is selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or
   a functional variant having at least 60% sequence identity to a peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.
5. The peptide or the peptide for use according to any of items 1 and 3, wherein said peptide variant has at least 60% sequence identity to SEQ ID NO:19, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to SEQ ID NO:19.
6. The peptide for use according to item 2, wherein said peptide variant has at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.
7. The peptide according to item 4, wherein said peptide variant has at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.
8. The peptide or the peptide for use according to any of the preceding items, wherein said peptide is capable of binding to Neural Cell Adhesion Molecule (NCAM).
9. The peptide or the peptide for use according to any of the preceding items, wherein said peptide is capable of stimulating neurite outgrowth and/or survival of neurons.
10. The peptide for use according to any of items 1-2, wherein said peptide is SKPDNPGEDAPAEDMARYYSALRHYINLITRQR (NPY3-35; SEQ ID NO:1), or a functional variant thereof having at least 60% sequence identity to SEQ ID NO:1.
11. The peptide or the peptide for use according to according to any of the preceding items, wherein said peptide variant comprises one amino acid substitution, for example two amino acid substitutions, such as three amino acid substitutions, for example four amino acid substitutions, such as five amino acid substitutions, for example six amino acid substitutions, such as seven amino acid substitutions.
12. The peptide or the peptide for use according to item 11, wherein said amino acid substitution is a conservative amino acid substitution.
13. The peptide or the peptide for use according to any of the preceding items, wherein the C-terminal amino acid exists as the free carboxylic acid ("—OH").
14. The peptide or the peptide for use according to any of the preceding items, wherein said peptide is formulated as a monomer.
15. The peptide or the peptide for use according to any of items 1 to 14, wherein said peptide is formulated as a multimer comprising two or more peptides.
16. The multimer according to item 15, wherein said multimeric peptide is a dimer (i.e. comprises two peptides).
17. The multimer according to item 15, wherein said multimeric peptide is a trimer (i.e. comprises three peptides).
18. The multimer according to item 15, wherein said multimeric peptide is a tetramer (i.e. comprises four peptides).
19. The multimer according to item 15, wherein said multimeric peptide is a dendrimer.
20. The multimer according to item 19, wherein said dendrimer comprises either 4, 8, 16 or 32 peptides.
21. The multimer according to item 15, wherein said multimer is a tetrameric dendrimer or a octameric dendrimer.
22. The multimer according to any of items 15 to 21, wherein said two or more peptides are identical with respect to each other.
23. The multimer according to any of items 15 to 21, wherein said two or more peptides are not identical with respect to each other.
24. The multimer according to any of items 15 to 21, wherein said two or more peptides are linked via a linker group.
25. The multimer according to any of items 15 to 21, wherein said linker group comprises one or more lysine residues.
26. A pharmaceutically acceptable composition comprising a peptide according to any of items 3-5 and 7-25.
27. A nucleic acid construct encoding a peptide consisting of a peptide sequence of from 15 to 33 contiguous amino acid residues derived from neuropeptide Y (NPY) (SEQ ID NO:22), wherein said peptide comprises or consists of the sequence YSALRHYIN- LITRQR (NPY21-35; SEQ ID NO:19), or a functional variant having at least 60% sequence identity to SEQ ID NO:19, wherein said peptide does not comprise the Tyr amino acid of position 36 of SEQ ID NO:22.

28. The nucleic acid construct according to item 27, wherein said functional variant has at least 60% sequence identity to SEQ ID NO:19, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to SEQ ID NO:19.

29. The nucleic acid construct for use according to any of items 27 to 28, wherein said encoded peptide is selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19; or
  a functional variant having at least 60% sequence identity, such as at least 65% sequence identity, for example at least 70% sequence identity, such as at least 75% sequence identity, for example at least 80% sequence identity, such as at least 85% sequence identity, for example at least 90% sequence identity, such as at least 95% sequence identity, for example at least 99% sequence identity to a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

30. A delivery vehicle comprising the nucleic acid construct according to any of items 27 to 29.

31. The delivery vehicle according to item 30, wherein said vehicle is selected from the group consisting of: RNA based vehicles, DNA based vehicles, lipid based vehicles, polymer based vehicles, colloidal gold particles and virally derived DNA or RNA vehicles.

32. The delivery vehicle according to item 30, wherein said vehicle is a viral vector selected from the group consisting of adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector 33. The delivery vehicle according to item 32, wherein said viral vector is a recombinant adeno-associated viruses (rAAV).

34. The peptide for use according to any of items 1-2, 5-6, and 8-25, or the nucleic acid construct according to any of items 27-33, wherein said disease or disorder of the central nervous system and/or the eye is a disease of the eye.

35. The use according to item 34, wherein said disease or disorder of the eye is a retinal or optic nerve disease or disorder.

36. The use according to item 35, wherein said disease or disorder is associated with retinal dystrophy or degeneration.

37. The use according to item 35, wherein said disease or disorder is retinal detachment, such as rhegmatogenous retinal detachment, exudative or secondary retinal detachment, and tractional retinal detachment.

38. The use according to item 35, wherein said disease or disorder is a retinopathy; such as diabetic retinopathy, including non-proliferative diabetic retinopathy (NPDR) and proliferative diabetic retinopathy (PDR); radiation retinopathy; hypertensive retinopathy; proliferative vitreoretinopathy; retinopathy due to autoimmune disease; retinopathy due to anemia; and retinopathy due to retinal vein or artery occlusion.

39. The use according to item 35, wherein said disease or disorder is macular degeneration, such as age-related macular degeneration (AMD), including dry or non-exudative AMD and wet or exudative AMD or myopic macular degeneration.

40. The use according to item 35, wherein said disease or disorder is retinitis pigmentosa.

41. The use according to item 35, wherein said disease or disorder is cone-rod dystrophy.

42. The use according to item 35, wherein said disease or disorder is glaucoma, including acute and chronic glaucoma, open-angle glaucoma and closed-angle glaucoma.

43. The use according to item 35, wherein said disease or disorder is selected from the group consisting of retinal vein and artery occlusion including central retinal vein occlusion and branch retinal vein occlusion; uveitis; ocular hypertension; optic neuropathy including ischemic optic neuropathy, compressive optic neuropathy, infiltrative optic neuropathy, traumatic optic neuropathy, mitochondrial optic neuropathies, nutritional optic neuropathies, toxic optic neuropathies, hereditary optic neuropathies; optic neuritis; optic nerve hypoplasia; Leber's congenital amaurosis (LCA), Lipemia retinalis, eye injury, Angioid streaks, and cancers of the retina including retinoblastoma and metastatic eye cancer.

44. The use according to any of items 35 to 43, wherein said peptide or nucleic acid construct is to be administered directly into the eye by means of intravitreal or subretinal administration.

45. The peptide for use according to any of items 1-2, 5-6, and 8-25, or the nucleic acid construct according to any of items 27-33, wherein said disease or disorder of the central nervous system and/or the eye is a disease or disorder of the central nervous system.

46. The use according to item 45, wherein said disease or disorder of the central nervous system is a neurodegenerative disorder.

47. The use according to item 46, wherein said neurodegenerative disorder is selected from the group consisting of Parkinson's disease, Alzheimer's disease, Huntington's disease Amyotrophic lateral sclerosis (ALS), spinocerebellar ataxias and Multiple Sclerosis.

48. The use according to item 46, wherein said neurodegenerative disorder is a polyglutamine disease, wherein said polyglutamine disease may be selected from the group consisting of Spinocerebellar ataxia type 1, Spinocerebellar ataxia type 2, Spinocerebellar ataxia type 3 (aka Machado-Joseph's disease), Spinocerebellar ataxia type 6, Spinocerebellar ataxia type 7 and Spinocerebellar ataxia type 17), DRPLA (Dentatorubro-pallidoluysian atrophy) and SBMA (Spinobulbar muscular atrophy or Kennedy disease).

49. The use according to item 45, wherein said disease or disorder of the central nervous system is stroke.

50. The use according to item 45, wherein said disease or disorder of the central nervous system is epilepsy.

51. The use according to any of items 45 to 50, wherein said peptide or nucleic acid construct is to be administered directly into the brain by means of intracerebral injection.
52. The use according to any of items 45 to 50, wherein said peptide or nucleic acid construct is to be administered by means of intrathecal injection.
53. The use according to item 45, wherein said disease or disorder of the central nervous system is a peripheral nerve lesion.
54. The peptide for use according to any of items 34 to 53, wherein said peptide is to be administered in combination with one or more second active ingredients.
55. The use according to item 54, wherein said second active ingredient is a GDNF-derived peptide, such as the GDNF-derived peptides disclosed in WO 2007/019860.
56. A kit of parts comprising a peptide, a nucleic acid construct or a composition according to any of the preceding items and at least one additional component.

The invention claimed is:

1. A method of treating a disease or disorder of the central nervous system selected from the group consisting of: a neurodegenerative disorder or disease, stroke, and epilepsy and an eye disease involving neurons and/or stimulating learning and memory, said method comprising administering to an individual in need thereof a composition comprising a peptide derived from neuropeptide Y (NPY) (SEQ ID NO:22), wherein said peptide is selected from the group consisting of:

a peptide consisting of 33 contiguous amino acid residues having the sequence SKPDNPGEDAPAED-MARYYSALRHYINLITRQR (NPY3-35, SEQ ID NO: 1), a peptide consisting of 32 contiguous amino acid residues having the sequence KPDNPGEDAPAED-MARYYSALRHYINLITRQR (NPY4-35, SEQ ID NO: 2), a peptide consisting of 31 contiguous amino acid residues having the sequence PDNPGEDAPAEDMARYYSAL-RHYINLITRQR (NPY5-35, SEQ ID NO: 3), a peptide consisting of 30 contiguous amino acid residues having the sequence DNPGEDAPAEDMARYYSAL-RHYINLITRQR (NPY6-35, SEQ ID NO: 4), a peptide consisting of 29 contiguous amino acid residues having the sequence NPGEDAPAEDMARYYSAL-RHYINLITRQR (NPY7-35, SEQ ID NO: 5), a peptide consisting of 28 contiguous amino acid residues having the sequence PGEDAPAEDMARYYSAL-RHYINLITRQR (NPY8-35, SEQ ID NO: 6), a peptide consisting of 27 contiguous amino acid residues having the sequence GEDAPAEDMARYYSAL-RHYINLITRQR (NPY9-35, SEQ ID NO: 7), a peptide consisting of 26 contiguous amino acid residues having the sequence EDAPAEDMARYYSALRHYIN-LITRQR (NPY10-35, SEQ ID NO: 8), a peptide consisting of 25 contiguous amino acid residues having the sequence DAPAEDMARYYSALRHYIN-LITRQR (NPY11-35, SEQ ID NO: 9), a peptide consisting of 24 contiguous amino acid residues having the sequence APAEDMARYYSALRHYIN-LITRQR (NPY12-35, SEQ ID NO: 10), a peptide consisting of 23 contiguous amino acid residues having the sequence PAEDMARYYSALRHYIN-LITRQR (NPY13-35, SEQ ID NO: 11), a peptide consisting of 22 contiguous amino acid residues having the sequence AEDMARYYSALRHYIN-LITRQR (NPY14-35, SEQ ID NO: 12), a peptide consisting of 21 contiguous amino acid residues having the sequence EDMARYYSALRHYINLITRQR (NPY15-35, SEQ ID NO: 13), a peptide consisting of 20 contiguous amino acid residues having the sequence DMARYYSALRHYINLITRQR (NPY16-35, SEQ ID NO: 14), a peptide consisting of 19 contiguous amino acid residues having the sequence MARYYSALRHYINLITRQR (NPY17-35, SEQ ID NO: 15), a peptide consisting of 18 contiguous amino acid residues having the sequence ARYYSALRHYINLITRQR (NPY18-35, SEQ ID NO: 16), a peptide consisting of 17 contiguous amino acid residues having the sequence RYYSALRHYINLITRQR (NPY19-35, SEQ ID NO: 17), a peptide consisting of 16 contiguous amino acid residues having the sequence YYSALRHYINLITRQR (NPY20-35, SEQ ID NO: 18), and a peptide consisting of 15 contiguous amino acid residues having the sequence YSALRHYINLITRQR (NPY21-35, SEQ ID NO: 19), or a variant of any one of the above peptides, wherein said variant comprises: 1) one conservative amino acid substitution in core sequence YSALRHYINLITRQR (NPY21-35, SEQ ID NO: 19), 2) one amino acid substitution outside said core sequence, or 3) both 1) and 2); provided that said variant has at least 90% sequence identity to any one of the above peptides, wherein said peptide or variant thereof stimulates neurite outgrowth, and wherein said peptide or variant thereof does not bind to and does not activate cognate NPY-receptors Y1, Y2 and/or Y5.

2. The method according to claim 1, wherein said peptide is a monomer.

3. The method according to claim 1, wherein said peptide is a multimer.

4. The method according to claim 3, wherein said multimer is a dendrimer comprising 4 peptides, 8 peptides, 16 peptides, or 32 peptides.

5. The method according to claim 3, wherein said multimer comprises two peptides, three peptides or four peptides.

6. The method according to claim 1, wherein said peptide is selected from the group consisting of:

```
(NPY3-35, SEQ ID NO: 1)
SKPDNPGEDAPAEDMARYYSALRHYINLITRQR, (NPY4-35, SEQ ID NO: 2)
KPDNPGEDAPAEDMARYYSALRHYINLITRQR, (NPY5-35, SEQ ID NO: 3)
PDNPGEDAPAEDMARYYSALRHYINLITRQR, (NPY6-35, SEQ ID NO: 4)
DNPGEDAPAEDMARYYSALRHYINLITRQR, (NPY7-35, SEQ ID NO: 5)
NPGEDAPAEDMARYYSALRHYINLITRQR, (NPY8-35, SEQ ID NO: 6)
PGEDAPAEDMARYYSALRHYINLITRQR, (NPY9-35, SEQ ID NO: 7)
GEDAPAEDMARYYSALRHYINLITRQR, (NPY10-35, SEQ ID NO: 8)
EDAPAEDMARYYSALRHYINLITRQR, (NPY11-35, SEQ ID NO: 9)
DAPAEDMARYYSALRHYINLITRQR, (NPY12-35, SEQ ID NO: 10)
APAEDMARYYSALRHYINLITRQR, (NPY13-35, SEQ ID NO: 11)
PAEDMARYYSALRHYINLITRQR, (NPY14-35, SEQ ID NO: 12)
AEDMARYYSALRHYINLITRQR, (NPY15-35, SEQ ID NO: 13)
EDMARYYSALRHYINLITRQR, (NPY16-35, SEQ ID NO: 14)
DMARYYSALRHYINLITRQR, (NPY17-35, SEQ ID NO: 15)
MARYYSALRHYINLITRQR, (NPY18-35, SEQ ID NO: 16)
ARYYSALRHYINLITRQR, (NPY19-35, SEQ ID NO: 17)
RYYSALRHYINLITRQR, (NPY20-35, SEQ ID NO: 18)
YYSALRHYINLITRQR,
and (NPY21-35, SEQ ID NO: 19)
YSALRHYINLITRQR.
```

7. The method according to claim 1, wherein said eye disease involving neurons is selected from the group consisting of: a retinal disease; an optic nerve disease; retinal dystrophy or degeneration; retinal detachment; a retinopathy; macular degeneration; retinitis pigmentosa; cone-rod dystrophy; glaucoma; retinal vein occlusion; artery vein occlusion; uveitis; ocular hypertension; optic neuropathies; optic neuritis; optic nerve hypoplasia; Leber's congenital amaurosis (LCA); lipemia retinalis; eye injuries; angioid streaks; and cancers of the retina.

8. The method according to claim 7, wherein said peptide is administered directly into an eye of said individual in need thereof.

9. The method according to claim 1, wherein said peptide is administered in combination with one or more further active ingredients and/or surgery.

10. The method according to claim 9, wherein said further active ingredient comprises an agent capable of inhibiting vascular endothelial growth factor (VEGF).

11. The method according to claim 9, wherein said peptide is administered simultaneously, separately or sequentially with respect to said one or more further active ingredients or surgery.

* * * * *

SEQUENCE LISTING

```
<160> NUMBER OF SEQ ID NOS: 45

<210> SEQ ID NO 1
<211> LENGTH: 33
<212> TYPE: PRT
<213> ORGANISM: Homo sapiens

<400> SEQUENCE: 1

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg

<210> SEQ ID NO 2
<211> LENGTH: 32
<212> TYPE: PRT
<213> ORGANISM: Homo sapiens

<400> SEQUENCE: 2

Lys Pro Asp Asn Pro Gly Glu Asp Ala Pro Ala Glu Asp Met Ala Arg
1               5                   10                  15

Tyr Tyr Ser Ala Leu Arg His Tyr Ile Asn Leu Ile Thr Arg Gln Arg
            20                  25                  30

<210> SEQ ID NO 3
<211> LENGTH: 31
<212> TYPE: PRT
<213> ORGANISM: Homo sapiens

<400> SEQUENCE: 3

Pro Asp Asn Pro Gly Glu Asp Ala Pro Ala Glu Asp Met Ala Arg Tyr
1               5                   10                  15

Tyr Ser Ala Leu Arg His Tyr Ile Asn Leu Ile Thr Arg Gln Arg
            20                  25                  30

<210> SEQ ID NO 4
<211> LENGTH: 30
<212> TYPE: PRT
<213> ORGANISM: Homo sapiens

<400> SEQUENCE: 4

Asp Asn Pro Gly Glu Asp Ala Pro Ala Glu Asp Met Ala Arg Tyr Tyr
1               5                   10                  15

Ser Ala Leu Arg His Tyr Ile Asn Leu Ile Thr Arg Gln Arg
            20                  25                  30

<210> SEQ ID NO 5
<211> LENGTH: 29
```

```
<212> TYPE: PRT
<213> ORGANISM: Homo sapiens

<400> SEQUENCE: 5

Asn Pro Gly Glu Asp Ala Pro Ala Glu Asp Met Ala Arg Tyr Tyr Ser
1               5                   10                  15

Ala Leu Arg His Tyr Ile Asn Leu Ile Thr Arg Gln Arg
            20                  25

<210> SEQ ID NO 6
<211> LENGTH: 28
<212> TYPE: PRT
<213> ORGANISM: Homo sapiens

<400> SEQUENCE: 6

Pro Gly Glu Asp Ala Pro Ala Glu Asp Met Ala Arg Tyr Tyr Ser Ala
1               5                   10                  15

Leu Arg His Tyr Ile Asn Leu Ile Thr Arg Gln Arg
            20                  25

<210> SEQ ID NO 7
<211> LENGTH: 27
<212> TYPE: PRT
<213> ORGANISM: Homo sapiens

<400> SEQUENCE: 7

Gly Glu Asp Ala Pro Ala Glu Asp Met Ala Arg Tyr Tyr Ser Ala Leu
1               5                   10                  15

Arg His Tyr Ile Asn Leu Ile Thr Arg Gln Arg
            20                  25

<210> SEQ ID NO 8
<211> LENGTH: 26
<212> TYPE: PRT
<213> ORGANISM: Homo sapiens

<400> SEQUENCE: 8

Glu Asp Ala Pro Ala Glu Asp Met Ala Arg Tyr Tyr Ser Ala Leu Arg
1               5                   10                  15

His Tyr Ile Asn Leu Ile Thr Arg Gln Arg
            20                  25

<210> SEQ ID NO 9
<211> LENGTH: 25
<212> TYPE: PRT
<213> ORGANISM: Homo sapiens

<400> SEQUENCE: 9

Asp Ala Pro Ala Glu Asp Met Ala Arg Tyr Tyr Ser Ala Leu Arg His
1               5                   10                  15

Tyr Ile Asn Leu Ile Thr Arg Gln Arg
            20                  25

<210> SEQ ID NO 10
<211> LENGTH: 24
<212> TYPE: PRT
<213> ORGANISM: Homo sapiens

<400> SEQUENCE: 10

Ala Pro Ala Glu Asp Met Ala Arg Tyr Tyr Ser Ala Leu Arg His Tyr
1               5                   10                  15

Ile Asn Leu Ile Thr Arg Gln Arg
```

-continued

```
                     20

<210> SEQ ID NO 11
<211> LENGTH: 23
<212> TYPE: PRT
<213> ORGANISM: Homo sapiens

<400> SEQUENCE: 11

Pro Ala Glu Asp Met Ala Arg Tyr Tyr Ser Ala Leu Arg His Tyr Ile
1               5                   10                  15

Asn Leu Ile Thr Arg Gln Arg
            20

<210> SEQ ID NO 12
<211> LENGTH: 22
<212> TYPE: PRT
<213> ORGANISM: Homo sapiens

<400> SEQUENCE: 12

Ala Glu Asp Met Ala Arg Tyr Tyr Ser Ala Leu Arg His Tyr Ile Asn
1               5                   10                  15

Leu Ile Thr Arg Gln Arg
            20

<210> SEQ ID NO 13
<211> LENGTH: 21
<212> TYPE: PRT
<213> ORGANISM: Homo sapiens

<400> SEQUENCE: 13

Glu Asp Met Ala Arg Tyr Tyr Ser Ala Leu Arg His Tyr Ile Asn Leu
1               5                   10                  15

Ile Thr Arg Gln Arg
            20

<210> SEQ ID NO 14
<211> LENGTH: 20
<212> TYPE: PRT
<213> ORGANISM: Homo sapiens

<400> SEQUENCE: 14

Asp Met Ala Arg Tyr Tyr Ser Ala Leu Arg His Tyr Ile Asn Leu Ile
1               5                   10                  15

Thr Arg Gln Arg
            20

<210> SEQ ID NO 15
<211> LENGTH: 19
<212> TYPE: PRT
<213> ORGANISM: Homo sapiens

<400> SEQUENCE: 15

Met Ala Arg Tyr Tyr Ser Ala Leu Arg His Tyr Ile Asn Leu Ile Thr
1               5                   10                  15

Arg Gln Arg

<210> SEQ ID NO 16
<211> LENGTH: 18
<212> TYPE: PRT
<213> ORGANISM: Homo sapiens

<400> SEQUENCE: 16
```

Ala Arg Tyr Tyr Ser Ala Leu Arg His Tyr Ile Asn Leu Ile Thr Arg
1               5                   10                  15

Gln Arg

<210> SEQ ID NO 17
<211> LENGTH: 17
<212> TYPE: PRT
<213> ORGANISM: Homo sapiens

<400> SEQUENCE: 17

Arg Tyr Tyr Ser Ala Leu Arg His Tyr Ile Asn Leu Ile Thr Arg Gln
1               5                   10                  15

Arg

<210> SEQ ID NO 18
<211> LENGTH: 16
<212> TYPE: PRT
<213> ORGANISM: Homo sapiens

<400> SEQUENCE: 18

Tyr Tyr Ser Ala Leu Arg His Tyr Ile Asn Leu Ile Thr Arg Gln Arg
1               5                   10                  15

<210> SEQ ID NO 19
<211> LENGTH: 15
<212> TYPE: PRT
<213> ORGANISM: Homo sapiens

<400> SEQUENCE: 19

Tyr Ser Ala Leu Arg His Tyr Ile Asn Leu Ile Thr Arg Gln Arg
1               5                   10                  15

<210> SEQ ID NO 20
<211> LENGTH: 14
<212> TYPE: PRT
<213> ORGANISM: Homo sapiens

<400> SEQUENCE: 20

Ser Ala Leu Arg His Tyr Ile Asn Leu Ile Thr Arg Gln Arg
1               5                   10

<210> SEQ ID NO 21
<211> LENGTH: 13
<212> TYPE: PRT
<213> ORGANISM: Homo sapiens

<400> SEQUENCE: 21

Ala Leu Arg His Tyr Ile Asn Leu Ile Thr Arg Gln Arg
1               5                   10

<210> SEQ ID NO 22
<211> LENGTH: 36
<212> TYPE: PRT
<213> ORGANISM: Homo sapiens
<220> FEATURE:
<221> NAME/KEY: MOD_RES
<222> LOCATION: (36)..(36)
<223> OTHER INFORMATION: AMIDATION

<400> SEQUENCE: 22

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 23
<211> LENGTH: 16
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: AMIDATION

<400> SEQUENCE: 23

Tyr Ser Ala Leu Arg His Tyr Ile Asn Leu Ile Thr Arg Gln Arg Tyr
1               5                   10                  15

<210> SEQ ID NO 24
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: AMIDATION

<400> SEQUENCE: 24

Ala Leu Arg His Tyr Ile Asn Leu Ile Thr Arg Gln Arg Tyr
1               5                   10

<210> SEQ ID NO 25
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: AMIDATION

<400> SEQUENCE: 25

Arg His Tyr Ile Asn Leu Ile Thr Arg Gln Arg Tyr
1               5                   10

<210> SEQ ID NO 26
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 26

Tyr Ile Asn Leu Ile Thr Arg Gln Arg Tyr
1               5                   10

<210> SEQ ID NO 27
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: AMIDATION

<400> SEQUENCE: 27

Ile Thr Arg Gln Arg Tyr
1               5

<210> SEQ ID NO 28
<211> LENGTH: 30
<212> TYPE: PRT
<213> ORGANISM: Homo sapiens

<400> SEQUENCE: 28

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu
            20                  25                  30

<210> SEQ ID NO 29
<211> LENGTH: 28
<212> TYPE: PRT
<213> ORGANISM: Homo sapiens

<400> SEQUENCE: 29

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu
            20                  25

<210> SEQ ID NO 30
<211> LENGTH: 20
<212> TYPE: PRT
<213> ORGANISM: Homo sapiens

<400> SEQUENCE: 30

Tyr Pro Ser Lys Pro Asp Asn Pro Gly Glu Asp Ala Pro Ala Glu Asp
1               5                   10                  15

Met Ala Arg Tyr
            20

<210> SEQ ID NO 31
<211> LENGTH: 14
<212> TYPE: PRT
<213> ORGANISM: Homo sapiens

<400> SEQUENCE: 31

Tyr Ser Ala Leu Arg His Tyr Ile Asn Leu Ile Thr Arg Gln
1               5                   10

<210> SEQ ID NO 32
<211> LENGTH: 97
<212> TYPE: PRT
<213> ORGANISM: Homo sapiens

<400> SEQUENCE: 32

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
            35                  40                  45

Tyr Ser Ala Leu Arg His Tyr Ile Asn Leu Ile Thr Arg Gln Arg Tyr
        50                  55                  60

Gly Lys Arg Ser Ser Pro Glu Thr Leu Ile Ser Asp Leu Leu Met Arg
65              70                  75                  80

Glu Ser Thr Glu Asn Val Pro Arg Thr Arg Leu Glu Asp Pro Ala Met
                85                  90                  95

Trp

<210> SEQ ID NO 33
<211> LENGTH: 30
<212> TYPE: PRT
<213> ORGANISM: Homo sapiens

<400> SEQUENCE: 33

Ser Ser Pro Glu Thr Leu Ile Ser Asp Leu Leu Met Arg Glu Ser Thr
1               5                   10                  15

Glu Asn Val Pro Arg Thr Arg Leu Glu Asp Pro Ala Met Trp
            20                  25                  30

<210> SEQ ID NO 34
<211> LENGTH: 12
<212> TYPE: PRT
<213> ORGANISM: Homo sapiens

<400> SEQUENCE: 34

Leu Arg His Tyr Ile Asn Leu Ile Thr Arg Gln Arg
1               5                   10

<210> SEQ ID NO 35
<211> LENGTH: 33
<212> TYPE: PRT
<213> ORGANISM: Homo sapiens

<400> SEQUENCE: 35

Arg Gln Arg Thr Ile Leu Asn Ile Tyr His Arg Leu Ala Ser Tyr Tyr
1               5                   10                  15

Arg Ala Met Asp Glu Ala Pro Ala Asp Glu Gly Pro Asn Asp Pro Lys
            20                  25                  30

Ser

<210> SEQ ID NO 36
<211> LENGTH: 15
<212> TYPE: PRT
<213> ORGANISM: Homo sapiens

<400> SEQUENCE: 36

Ala Ser Ala Leu Arg His Tyr Ile Asn Leu Ile Thr Arg Gln Arg
1               5                   10                  15

<210> SEQ ID NO 37
<211> LENGTH: 36
<212> TYPE: PRT
<213> ORGANISM: Homo sapiens

<400> SEQUENCE: 37

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 38
<211> LENGTH: 34
<212> TYPE: PRT
<213> ORGANISM: Homo sapiens
<220> FEATURE:
<221> NAME/KEY: MOD_RES
<222> LOCATION: (34)..(34)

```
<223> OTHER INFORMATION: AMIDATION

<400> SEQUENCE: 38

Ser Lys Pro Asp Asn Pro Gly Glu Asp Ala Pro Ala Glu Asp Met Ala
1               5                   10                  15
Arg Tyr Tyr Ser Ala Leu Arg His Tyr Ile Asn Leu Ile Thr Arg Gln
            20                  25                  30
Arg Tyr

<210> SEQ ID NO 39
<211> LENGTH: 16
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: AMIDATION

<400> SEQUENCE: 39

Tyr Ser Ala Leu Arg His Tyr Ile Asn Leu Ile Thr Arg Gln Arg Tyr
1               5                   10                  15

<210> SEQ ID NO 40
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: AMIDATION

<400> SEQUENCE: 40

Ala Leu Arg His Tyr Ile Asn Leu Ile Thr Arg Gln Arg Tyr
1               5                   10

<210> SEQ ID NO 41
<211> LENGTH: 14
<212> TYPE: PRT
<213> ORGANISM: Homo sapiens

<400> SEQUENCE: 41

Ala Leu Arg His Tyr Ile Asn Leu Ile Thr Arg Gln Arg Ala
1               5                   10

<210> SEQ ID NO 42
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: AMIDATION

<400> SEQUENCE: 42

Arg His Tyr Ile Asn Leu Ile Thr Arg Gln Arg Tyr
1               5                   10

<210> SEQ ID NO 43
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 43
```

```
Tyr Ile Asn Leu Ile Thr Arg Gln Arg Tyr
1               5                   10

<210> SEQ ID NO 44
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: ACETYLATION

<400> SEQUENCE: 44

Ile Thr Arg Gln Arg Tyr
1               5

<210> SEQ ID NO 45
<211> LENGTH: 36
<212> TYPE: PRT
<213> ORGANISM: Homo sapiens

<400> SEQUENCE: 45

Tyr Arg Gln Arg Thr Ile Leu Asn Ile Tyr His Arg Leu Ala Ser Tyr Tyr
1               5                   10                  15

Arg Ala Met Asp Glu Ala Pro Ala Asp Glu Gly Pro Asn Asp Pro Lys
            20                  25                  30

Ser Pro Tyr
        35
```